(12) United States Patent
Ziv et al.

(10) Patent No.: US 9,655,769 B2
(45) Date of Patent: May 23, 2017

(54) PESSARIES FOR PROLAPSE ALLEVIATION

(71) Applicant: ConTIPI Ltd., Caesarea (IL)

(72) Inventors: Elan Ziv, Ramat-Gan (IL); Amir Perle, Haifa (IL); Elisheva Fabrikant, Herzlia (IL)

(73) Assignee: ConTIPI Medical Ltd., Caesarea (IL)

( * ) Notice: Subject to any disclaimer, the term of this patent is extended or adjusted under 35 U.S.C. 154(b) by 370 days.

(21) Appl. No.: 14/181,676

(22) Filed: Feb. 16, 2014

(65) Prior Publication Data

US 2014/0158138 A1 Jun. 12, 2014

Related U.S. Application Data

(63) Continuation of application No. 12/417,011, filed on Apr. 2, 2009, now Pat. No. 8,651,109.

(60) Provisional application No. 61/071,344, filed on Apr. 23, 2008.

(51) Int. Cl.
| | |
|---|---|
| A61F 6/06 | (2006.01) |
| A61F 2/00 | (2006.01) |
| A61F 6/12 | (2006.01) |
| A61F 6/08 | (2006.01) |

(52) U.S. Cl.
CPC ............... *A61F 6/12* (2013.01); *A61F 2/005* (2013.01); *A61F 6/08* (2013.01); *A61F 2/0027* (2013.01); *A61F 2250/001* (2013.01); *A61F 2250/0003* (2013.01); *A61F 2250/009* (2013.01);
(Continued)

(58) Field of Classification Search
CPC ........................................................ A61F 6/12

USPC ............... 600/29–32, 37; 128/DIG. 25, 885, 128/830–841; 604/330–331; 623/1.23, 623/1.11, 1.12
See application file for complete search history.

(56) References Cited

U.S. PATENT DOCUMENTS

| | | |
|---|---|---|
| 2,141,040 A | 12/1938 | Holt |
| 2,146,574 A | 2/1939 | Hay |
| 2,432,768 A | 12/1947 | Kurkjian |
| | (Continued) | |

FOREIGN PATENT DOCUMENTS

| | | |
|---|---|---|
| CN | 1036900 | 11/1989 |
| CN | 101001584 | 7/2007 |
| | (Continued) | |

OTHER PUBLICATIONS

Applicant-Initiated Interview Summary Dated Jun. 30, 2014 From the US Patent and Trademark Office Re. U.S. Appl. No. 12/663,714.
(Continued)

*Primary Examiner* — Tarla Patel

(57) ABSTRACT

Disclosed are devices for supporting a prolapsed organ. An exemplary device comprises a ring-like body optionally having a naturally occurring substantially flat and substantially planar compact configuration, the ring-like body configured with a size suitable for insertion into a vagina and to be expanded by a support element such that in the expanded configuration an outer periphery of the ring-like body contacts a portion of the vagina and stretches at least a portion of a prolapsed vaginal wall, thereby substantially alleviating prolapse of at least one pelvic organ. The device optionally includes a support element comprising two moveably connected arms configured to support the ring in the expanded configuration.

19 Claims, 33 Drawing Sheets

(52) U.S. Cl.
CPC ............... *A61F 2250/0039* (2013.01); *A61F 2250/0065* (2013.01); *A61F 2250/0071* (2013.01)

(56) References Cited

U.S. PATENT DOCUMENTS

| | | | |
|---|---|---|---|
| 2,769,442 A | 11/1956 | Stubbs | |
| 2,856,920 A | 10/1958 | Indelicato | |
| 2,938,519 A | 5/1960 | Marco | |
| 3,138,159 A | 6/1964 | Schmidt | |
| 3,646,929 A | 3/1972 | Bonnar | |
| 3,658,057 A | 4/1972 | Cimber | |
| 3,683,906 A | 8/1972 | Robinson | |
| 3,789,828 A | 2/1974 | Schulte | |
| 3,797,478 A | 3/1974 | Walsh et al. | |
| 3,841,304 A | 10/1974 | Jones | |
| 4,019,498 A | 4/1977 | Hawtrey | |
| 4,019,499 A | 4/1977 | Fitzgerald | |
| 4,139,006 A | 2/1979 | Corey | |
| 4,142,649 A | 3/1979 | Forgey | |
| 4,212,301 A | 7/1980 | Johnson | |
| 4,307,716 A | 12/1981 | Davis | |
| 4,428,365 A | 1/1984 | Hakky | |
| 4,457,299 A | 7/1984 | Cornwell | |
| 4,553,533 A | 11/1985 | Leighton | |
| 4,726,805 A | 2/1988 | Sanders | |
| 4,823,814 A | 4/1989 | Drogendijk et al. | |
| 4,846,784 A | 7/1989 | Haber | |
| 4,850,963 A | 7/1989 | Sparks et al. | |
| 4,920,986 A | 5/1990 | Biswas | |
| 5,007,894 A | 4/1991 | Enhorning | |
| 5,014,722 A * | 5/1991 | Bauer | A61F 6/18 128/830 |
| 5,036,867 A | 8/1991 | Biswas | |
| 5,041,077 A | 8/1991 | Kulick | |
| 5,090,424 A | 2/1992 | Simon et al. | |
| 5,167,237 A | 12/1992 | Rabin et al. | |
| 5,224,493 A | 7/1993 | Sawan et al. | |
| 5,224,494 A | 7/1993 | Enhorning | |
| 5,336,208 A | 8/1994 | Rosenbluth et al. | |
| 5,352,182 A | 10/1994 | Kalb et al. | |
| 5,370,657 A | 12/1994 | Irie | |
| 5,386,836 A | 2/1995 | Biswas | |
| 5,417,226 A | 5/1995 | Juma | |
| 5,483,976 A | 1/1996 | McLaughlin et al. | |
| 5,603,685 A | 2/1997 | Tutrone, Jr. | |
| 5,609,586 A | 3/1997 | Zadini et al. | |
| 5,618,256 A | 4/1997 | Reimer | |
| 5,659,934 A | 8/1997 | Jessup et al. | |
| 5,671,755 A | 9/1997 | Simon et al. | |
| 5,724,994 A | 3/1998 | Simon et al. | |
| 5,755,906 A | 5/1998 | Achter et al. | |
| 5,771,899 A | 6/1998 | Martelly et al. | |
| 5,782,745 A * | 7/1998 | Benderev | A61F 2/0009 128/DIG. 25 |
| 5,785,640 A | 7/1998 | Kresch et al. | |
| 5,788,664 A | 8/1998 | Scalise | |
| 5,795,346 A | 8/1998 | Achter et al. | |
| 5,894,842 A | 4/1999 | Rabin et al. | |
| 6,013,023 A | 1/2000 | Klingenstein | |
| 6,090,038 A | 7/2000 | Zunker et al. | |
| 6,090,098 A | 7/2000 | Zunker et al. | |
| 6,142,928 A | 11/2000 | Zunker et al. | |
| 6,158,435 A | 12/2000 | Dorsey | |
| 6,189,535 B1 | 2/2001 | Enhorning | |
| 6,216,698 B1 | 4/2001 | Regula | |
| 6,251,122 B1 | 6/2001 | Tsukernik | |
| 6,413,206 B2 | 7/2002 | Biswas | |
| 6,415,484 B1 | 7/2002 | Moser | |
| 6,418,930 B1 | 7/2002 | Fowler | |
| 6,428,467 B1 | 8/2002 | Benderev | |
| 6,458,072 B1 | 10/2002 | Zunker | |
| 6,460,542 B1 | 10/2002 | James | |
| 6,461,215 B1 | 10/2002 | Kunz et al. | |
| 6,478,726 B1 | 11/2002 | Zunker | |
| 6,503,190 B1 | 1/2003 | Ulmsten et al. | |
| 6,558,370 B2 | 5/2003 | Moser | |
| 6,645,136 B1 | 11/2003 | Zunker et al. | |
| 6,676,594 B1 | 1/2004 | Zunker et al. | |
| 6,679,831 B1 | 1/2004 | Zunker et al. | |
| 6,739,340 B1 | 5/2004 | Jensen et al. | |
| 6,770,025 B2 | 8/2004 | Zunker | |
| 6,808,485 B2 | 10/2004 | Zunker | |
| 7,036,511 B2 | 5/2006 | Nissenkorn | |
| 7,717,892 B2 | 5/2010 | Bartning et al. | |
| 7,931,671 B2 | 4/2011 | Tenerz | |
| 8,435,168 B2 | 5/2013 | Ziv et al. | |
| 2002/0068023 A1 | 6/2002 | Davis | |
| 2002/0083949 A1 | 7/2002 | James | |
| 2002/0115906 A1 | 8/2002 | Miller | |
| 2002/0120243 A1 | 8/2002 | Kraemer et al. | |
| 2002/0138035 A1 | 9/2002 | Hull, Jr. | |
| 2002/0156341 A1 | 10/2002 | Zunker | |
| 2002/0156343 A1 | 10/2002 | Zunker | |
| 2002/0183711 A1 | 12/2002 | Moser | |
| 2003/0073880 A1 | 4/2003 | Polsky et al. | |
| 2003/0149334 A1 | 8/2003 | Ulmsten et al. | |
| 2003/0149392 A1 | 8/2003 | Arnould | |
| 2004/0054252 A1 | 3/2004 | Zunker | |
| 2004/0078013 A1 | 4/2004 | Zunker et al. | |
| 2004/0084054 A1 | 5/2004 | Kaseki et al. | |
| 2004/0122285 A1 | 6/2004 | Zunker | |
| 2004/0158122 A1 | 8/2004 | Guerquin | |
| 2004/0199100 A1 | 10/2004 | LeMay et al. | |
| 2005/0016545 A1 | 1/2005 | Nissenkorn | |
| 2006/0100475 A1 | 5/2006 | White et al. | |
| 2007/0088189 A1 | 4/2007 | Levy | |
| 2007/0203429 A1 | 8/2007 | Ziv | |
| 2007/0244352 A1 | 10/2007 | Ziv | |
| 2008/0149109 A1 | 6/2008 | Ziv | |
| 2008/0281149 A1 * | 11/2008 | Sinai | A61F 2/005 600/32 |
| 2009/0266367 A1 | 10/2009 | Ziv et al. | |
| 2009/0283099 A1 * | 11/2009 | Harmanli | A61F 2/005 128/834 |
| 2011/0065980 A1 | 3/2011 | Ziv et al. | |
| 2012/0271098 A1 | 10/2012 | Ziv et al. | |
| 2013/0165743 A1 | 6/2013 | Ziv et al. | |
| 2014/0039245 A1 | 2/2014 | Ziv | |
| 2014/0073846 A1 | 3/2014 | Sinai et al. | |
| 2016/0015500 A1 | 1/2016 | Ziv et al. | |

FOREIGN PATENT DOCUMENTS

| | | |
|---|---|---|
| DE | 271657 | 3/1914 |
| DE | 19816349 | 10/1999 |
| EP | 0264258 | 4/1988 |
| EP | 0274762 | 7/1988 |
| EP | 0933069 | 8/1988 |
| EP | 0700669 | 3/1996 |
| EP | 0921778 | 6/1999 |
| EP | 0955024 | 11/1999 |
| EP | 1139963 | 10/2001 |
| EP | 1139962 | 5/2005 |
| EP | 1727491 | 12/2006 |
| FR | 2843700 | 2/2004 |
| GB | 1115727 | 5/1968 |
| GB | 2352181 | 1/2001 |
| GB | 2384436 | 7/2003 |
| JP | 63-177852 | 7/1988 |
| JP | 03-500489 | 2/1991 |
| JP | 06-133996 | 5/1994 |
| JP | 06-503982 | 5/1994 |
| JP | 61-33996 | 5/1994 |
| JP | 09-501595 | 2/1997 |
| JP | 2001-502929 | 3/2001 |
| JP | 2002-532198 | 2/2002 |
| JP | 2002-5332199 | 10/2002 |
| WO | WO 88/10106 | 12/1988 |
| WO | WO 89/09582 | 10/1989 |
| WO | WO 95/05790 | 3/1995 |
| WO | WO 96/01084 | 1/1996 |
| WO | WO 97/34550 | 9/1997 |
| WO | WO 98/49980 | 11/1998 |

(56) References Cited

FOREIGN PATENT DOCUMENTS

| WO | WO 00/03659 | 1/2000 |
|---|---|---|
| WO | WO 00/36996 | 6/2000 |
| WO | WO 00/67662 | 11/2000 |
| WO | WO 02/26160 | 4/2002 |
| WO | WO 02/089704 | 11/2002 |
| WO | WO 03/047476 | 6/2003 |
| WO | WO 2004/000433 | 12/2003 |
| WO | WO 2004/103213 | 12/2004 |
| WO | WO 2005/087153 | 9/2005 |
| WO | WO 2005/087154 | 9/2005 |
| WO | WO 2006/097935 | 9/2006 |
| WO | WO 2008/010214 | 1/2008 |
| WO | WO 2008/079271 | 7/2008 |
| WO | WO 2008/152628 | 12/2008 |
| WO | WO 2009/044394 | 4/2009 |
| WO | WO 2009/130702 | 10/2009 |

OTHER PUBLICATIONS

Invitation Pursuant to Article 94(3) EPC Dated Jun. 17, 2014 From the European Patent Office Re. Application No. 08763544.7.
Advisory Action Before the Filing of an Appeal Brief Dated Jun. 12, 2015 From the US Patent and Trademark Office Re. U.S. Appl. No. 12/663,714.
Requisition by the Examiner Dated May 21, 2015 From the Canadian Intellectual Property Office Re. Application No. 2,722,234.
Office Action Dated May 14, 2014 From the State Intellectual Property Office of the People's Republic of China Re. Application No. 200980123856.5 and Its Translation Into English.
Communication Pursuant to Article 94(3) EPC Dated Feb. 23, 2015 From the European Patent Office Re. Application No. 08763544.7.
European Search Report Dated Mar. 11, 2015 From the European Patent Office Re. Application No. 14192972.9.
Official Action Dated Mar. 13, 2015 From the US Patent and Trademark Office Re. U.S. Appl. No. 12/663,714.
Advisory Action Before the Filing of an Appeal Brief Dated Jul. 20, 2014 From the US Patent and Trademark Office Re. U.S. Appl. No. 12/663,714.
Applicant-Initiated Interview Summary Dated Aug. 9, 2013 From the US Patent and Trademark Office Re. U.S. Appl. No. 12/680,575.
Applicant-Initiated Interview Summary Dated Jan. 16, 2014 From the US Patent and Trademark Office Re. U.S. Appl. No. 13/772,410.
Applicant-Initiated Interview Summary Dated Jun. 28, 2013 From the US Patent and Trademark Office Re. U.S. Appl. No. 12/680,575.
Communication Pursuant to Article 94(3) EPC Dated Nov. 3, 2011 From the European Patent Office Re. Application No. 07789949.0.
Communication Pursuant to Article 94(3) EPC Dated Feb. 4, 2011 From the European Patent Office Re. Application No. 04734069.0.
Communication Pursuant to Article 94(3) EPC Dated Apr. 16, 2009 From the European Patent Office Re.: Application No. 05718876.5.
Communication Pursuant to Article 94(3) EPC Dated Mar. 23, 2010 From the European Patent Office Re.: Application No. 05718876.5.
Communication Pursuant to Article 94(3) EPC Dated Nov. 29, 2013 From the European Patent Office Re. Application No. 08808093.2.
Communication Pursuant to Article 94(3) EPC Dated Jan. 31, 2014 From the European Patent Office Re. Application No. 08763544.7.
Communication Pursuant to Rules 70(2) and 70a(2) EPC and Reference to Rule 39(1) EPC Dated Jan. 2, 2014 From the European Patent Office Re. Application No. 11188150.4.
Communication Pursuant to Rules 70(2) and 70a(2) EPC Dated Nov. 8, 2013 From the European Patent Office Re. Application No. 06711327.4.
Communication Relating to the Results of the Partial International Search Dated Mar. 3, 2011 From the International Searching Authority Re. Application No. PCT/IL2010/000985.
Communication Relating to the Results of the Partial International Search Dated Dec. 7, 2007 From the International Searching Authority Re.: Application No. PCT/IL2007/000893.

Communication Relating to the Results of the Partial International Search Dated Jan. 12, 2009 From the International Searching Authority Re.: Application No. PCT/IL2007/000893.
Communication Relating to the Results of the Partial International Search Dated Jan. 12, 2009 From the International Searching Authority Re.: Application No. PCT/IL2008/001292.
Communication Relating to the Results of the Partial International Search Dated Aug. 18, 2009 From the International Searching Authority Re.: Application No. PCT/IL2009/000443.
Communication Under Rule 112 EPC Dated Oct. 22, 2007 From the European Patent Office Re.: Application No. 05718876.5.
Communication Under Rule 71(3) EPC Dated May 27, 2011 From the European Patent Office Re. Application No. 09735573.9.
Communication Pursuant to Article 94(3) EPC Dated Jul. 2, 2010 From the European Patent Office Re.: Application No. 05718877.3.
Communication Pursuant to Article 94(3) EPC Dated Apr. 16, 2009 From the European Patent Office Re.: Application No. 05718877.3.
Decision to Refuse a European Patent Application Dated Feb. 25, 2013 From the European Patent Office Re. Application No. 04734069.0.
European Search Report and the European Search Opinion Dated Nov. 14, 2013 From the European Patent Office Re. Application No. 11188150.4.
European Search Report Under Rule 112 EPC Dated Dec. 27, 2007 From the European Patent Office Re.: Application No. 05718876.5.
Examination Report Dated Oct. 13, 2010 From the Instituto Mexicano de la Propiedad Industrial Re. Application No. MX/a/2007/011339 and Its Summary in English.
Examination Report Dated Oct. 13, 2011 From the Instituto Mexicano de la Propiedad Industrial Re. Application No. MX/a/2007/011339 and Its translation Into English.
Examination Report Dated Feb. 16, 2012 From the Government of India, Patent Office, Intellectual Property Building Re. Application No. 3837/CHENP/2006.
Examination Report Dated Jan. 16, 2012 From the Instituto Mexicano de la Propriedad Industrial Re. Application No. PA/a/2006/010653 and Its Summary in English.
Examination Report Dated May 30, 2012 From the Instituto Mexicano de la Propiedad Industrial Re. Application No. MX/a/2007/011339 and Its Translation Into English.
Examination Report Dated Mar. 31, 2011 From the Instituto Mexicano de la Propiedad Industrial Re. Application No. MX/a/2007/011339.
Examiner-Initiated Interview Summary Dated Oct. 10, 2012 From the US Patent and Trademark Office Re. U.S. Appl. No. 12/680,575.
Examiner's Report Dated Dec. 9, 2009 From the Australian Government, IP Australia Re.: Application No. 2005221424.
Examiner's Report Dated Dec. 15, 2010 From the Australian Government, IP Australia Re.: Application No. 2005221424.
Examiner's Report Dated Nov. 29, 2010 From the Australian Government, IP Australia Re. Application No. 2006224158.
International Preliminary Report on Patentability Dated Jul. 6, 2006 From the International Preliminary Examining Authority Re.: Application No. PCT/IL2005/000304.
International Preliminary Report on Patentability Dated Jun. 7, 2012 From the International Bureau of WIPO Re. Application No. PCT/IL2010/000985.
International Preliminary Report on Patentability Dated Dec. 8, 2009 From the International Preliminary Examining Authority Re.: Application No. PCT/IL2008/001292.
International Preliminary Report on Patentability Dated Oct. 14, 2008 From the International Preliminary Examining Authority Re.: Application No. PCT/IL06/00346.
International Preliminary Report on Patentability Dated Jul. 15, 2010 From the International Preliminary Examining Authority Re.: Application No. PCT/IL2009/000443.
International Preliminary Report on Patentability Dated Dec. 23, 2009 From the International Bureau of WIPO Re.: Application No. PCT/IL2008/000786.
International Preliminary Report on Patentability Dated Jul. 24, 2006 From the International Preliminary Examining Authority Re.: Application No. PCT/IL2005/000303.

(56) References Cited

OTHER PUBLICATIONS

International Preliminary Report on Patentability Dated Jan. 29, 2009 From the International Bureau of WIPO Re.: Application No. PCT/IL2007/000893.
International Search Report and the Written Opinion Dated May 9, 2011 From the International Searching Authority Re. Application No. PCT/IL2010/000985.
International Search Report and the Written Opinion Dated Oct. 26, 2005 From the International Searching Authority Re.: Application No. PCT/IL2005/000303.
International Search Report and the Written Opinion Dated Oct. 28, 2009 From the International Searching Authority Re.: Application No. PCT/IL2009/000443.
International Search Report Dated Dec. 11, 2006 From the International Searching Authority Re.: Application No. PCT/IL06/00346.
International Search Report Dated Apr. 14, 2008 From the International Searching Authority Re.: Application No. PCT/IL2007/000893.
International Search Report Dated Sep. 23, 2005 From the International Searching Authority Re.: Application No. PCT/IL2005/000304.
International Search Report Dated Oct. 24, 2008 From the International Searching Authority Re.: Application No. PCT/IL2008/000786.
International Search Report Dated Mar. 25, 2009 From the International Searching Authority Re.: Application No. PCT/IL2008/001292.
Interview Summary Dated Feb. 9, 2011 From the US Patent and Trademark Office Re.: U.S. Appl. No. 10/593,367.
Invitation Pursuant to Rule 62a(1) EPC Dated Aug. 8, 2013 From the European Patent Office Re. Application No. 06711327.4.
Letter After Telephone Conference Dated Jul. 5, 2010 From the International Searching Authority Re. Application No. PCT/IL2009/000443.
Notice of Acceptance Dated Feb. 2, 2011 From the Australian Government, IP Australia Re.: Application No. 2005221424.
Notice of Allowance Dated Oct. 2, 2013 From the US Patent and Trademark Office Re. U.S. Appl. No. 12/417,011.
Notice of Allowance Dated Aug. 6, 2013 From the US Patent and Trademark Office Re. U.S. Appl. No. 11/886,248.
Notice of Allowance Dated Jan. 7, 2013 From the US Patent and Trademark Office Re. U.S. Appl. No. 12/373,937.
Notice of Allowance Dated Jan. 8, 2014 From the US Patent and Trademark Office Re. U.S. Appl. No. 10/598,872.
Notice of Allowance Dated Nov. 14, 2011 From the US Patent and Trademark Office Re.: U.S. Appl. No. 10/593,367.
Notice of Allowance Dated Mar. 31, 2010 From the US Patent and Trademark Office Re.: U.S. Appl. No. 10/557,865.
Notification Dated Dec. 17, 2008 From the Patent Office of the Russian Federation Re.: Application No. 2006136791 and Its Translation Into English.
Notification of Reasons for Rejection Dated Oct. 4, 2013 From the Japanese Patent Office Re. Application No. 2011-223943 and Its Translation Into English.
Notification of Reasons for Rejection Dated Feb. 18, 2011 From the Japanese Patent Office Re. Application No. 2007-503494 and Its Translation into English.
Office Action Dated Sep. 1, 2008 From the Israeli Patent Office Re.: Application No. 156070 and Its Translation Into English.
Office Action Dated Sep. 1, 2008 From the Israeli Patent Office Re.: Application No. 157117 and Its Translation Into English.
Office Action Dated Apr. 5, 2011 From the Israel Patent Office Re.: Application No. 156070 and Its Translation Into English.
Office Action Dated Dec. 5, 2012 From the Israel Patent Office Re. Application No. 176883 and Its Translation Into English.
Office Action Dated Jan. 9, 2009 From the State Intellectual Property Office of the People's Republic of China Re.: Application No. 200580016245.2 and Its Translation Into English.
Office Action Dated Nov. 12, 2013 From the State Intellectual Property Office of the People's Republic of China Re. Application No. 200980123856.5 and Its Translation Into English.
Office Action Dated Jan. 18, 2010 From the Israel Patent Office Re.: Application No. 156070 and Its Translation into English.
Office Action Dated Dec. 19, 2013 From the Israel Patent Office Re. Application No. 219989 and Its Translation Into English.
Office Action Dated Jul. 24, 2011 From the Israel Patent Office Re. Application No. 176883 and Its Translation Into English.
Office Action Dated Dec. 31, 2013 From the Israel Patent Office Re. Application No. 219988 and Its Translation Into English.
Office Action Dated Dec. 31, 2013 From the Israel Patent Office Re. Application No. 222951 and Its Translation Into English.
Official Action Dated Jul. 1, 2013 From the US Patent and Trademark Office Re. U.S. Appl. No. 12/663,714.
Official Action Dated Aug. 4, 2010 From the US Patent and Trademark Office Re.: U.S. Appl. No. 10/598,872.
Official Action Dated Sep. 5, 2008 From the US Patent and Trademark Office Re.: U.S. Appl. No. 10/557,865.
Official Action Dated Mar. 6, 2009 From the US Patent and Trademark Office Re.: U.S. Appl. No. 10/557,865.
Official Action Dated Mar. 6, 2014 From the US Patent and Trademark Office Re. U.S. Appl. No. 12/663,714.
Official Action Dated May 6, 2013 From the US Patent and Trademark Office Re. U.S. Appl. No. 11/886,248.
Official Action Dated Apr. 9, 2012 From the US Patent and Trademark Office Re. U.S. Appl. No. 12/417,011.
Official Action Dated Mar. 12, 2013 From the US Patent and Trademark Office Re. U.S. Appl. No. 12/680,575.
Official Action Dated Oct. 12, 2010 From the US Patent and Trademark Office Re. U.S. Appl. No. 10/598,872.
Official Action Dated Feb. 14, 2011 From the US Patent and Trademark Office Re.: U.S. Appl. No. 10/598,872.
Official Action Dated Oct. 14, 2011 From the US Patent and Trademark Office Re. U.S. Appl. No. 12/417,011.
Official Action Dated Feb. 15, 2012 From the US Patent and Trademark Office Re. U.S. Appl. No. 12/373,937.
Official Action Dated Oct. 15, 2009 From the US Patent and Trademark Office Re.: U.S. Appl. No. 10/557,865.
Official Action Dated Apr. 17, 2009 From the Patent Office of the Russian Federation Re.: Application No. 2006136791 and Its Translation Into English.
Official Action Dated Feb. 19, 2010 From the US Patent and Trademark Office Re.: U.S. Appl. No. 10/593,367.
Official Action Dated Jun. 21, 2011 From the US Patent and Trademark Office Re.: U.S. Appl. No. 10/593,367.
Official Action Dated Jul. 23, 2012 From the US Patent and Trademark Office Re. U.S. Appl. No. 12/373,937.
Official Action Dated Jul. 23, 2013 From the US Patent and Trademark Office Re. U.S. Appl. No. 10/598,872.
Official Action Dated Jun. 23, 2010 From the US Patent and Trademark Office Re.: U.S. Appl. No. 10/593,367.
Official Action Dated Aug. 24, 2012 From the US Patent and Trademark Office Re. U.S. Appl. No. 11/886,248.
Official Action Dated Sep. 24, 2013 From the US Patent and Trademark Office Re. U.S. Appl. No. 13/772,410.
Official Action Dated Jan. 27, 2014 From the US Patent and Trademark Office Re. U.S. Appl. No. 12/680,575.
Official Action Dated Oct. 27, 2009 From the Federal Institute of Industrial and Intellectual Property, Patents and Trademarks, ROSPATENT, of the Russian Federation Re.: Application No. 2007138489 and Its Translation Into English.
Official Action Dated Dec. 28, 2010 From the US Patent and Trademark Office Re.: U.S. Appl. No. 10/593,367.
Official Action Dated Apr. 29, 2010 From the US Patent and Trademark Office Re.: U.S. Appl. No. 10/598,872.
Official Action Dated May 31, 2011 From the US Patent and Trademark Office Re. U.S. Appl. No. 12/417,011.
Patent Examination Report Dated Aug. 9, 2012 From the Australian Government, IP Australia Re. Application No. 2007274574.
Request for Examination Dated Apr. 4, 2013 From the Federal Service for Intellectual Property, Federal State Budgetary Institu-

(56) References Cited

OTHER PUBLICATIONS tion, Federal Institute of Industrial Property of the Russian Federation Re. Application No. 2010146714 and Its Summary in English.
Request for Examination Dated Jun. 11, 2010 From the Federal Institute of Industrial and Intellectual Property, Patents and Trademarks, ROSPATENT, of the Russian Federation Re.: Application No. 2010100368 and Its Summary in English.
Request for Examination Dated Mar. 29, 2012 From the Federal Institute of Industrial and Intellectual Property, Patents and Trademarks, ROSPATENT, of the Russian Federation Re.: Application No. 2010100368 and Its Summary in English.
Request for Formal Examination Dated Feb. 24, 2011 From the ROSPATENT, Federal Government Institution, Federal Institute of Industrial Property of the Federal Service for Intellectual Property, Patents and Trademarks of the Russian Federation Re. Application No. 2010146714.
Requisition by the Examiner Dated Feb. 19, 2013 From the Canadian Intellectual Property Office Re. Application No. 2,560,877.
Requisition by the Examiner Dated Aug. 22, 2012 From the Canadian Intellectual Property Office Re. Application No. 2,600,988.
Requisition by the Examiner Dated May 22, 2012 From the Canadian Intellectual Property Office Re. Application No. 2,560,877.
Requisition by the Examiner Dated May 28, 2013 From the Canadian Intellectual Property Office Re. Application No. 2,600,988.
Requisition by the Examiner Dated Aug. 29, 2011 From the Canadian Intellectual Property Office Re. Application No. 2,560,877.
Restriction Official Action Dated Nov. 1, 2012 From the US Patent and Trademark Office Re. U.S. Appl. No. 12/680,575.
Restriction Official Action Dated Feb. 6, 2013 From the US Patent and Trademark Office Re. U.S. Appl. No. 12/663,714.
Restriction Official Action Dated Feb. 28, 2012 From the US Patent and Trademark Office Re. U.S. Appl. No. 11/886,248.
Second Supplemental Notice of Allowability Dated Jun. 3, 2010 From the US Patent and Trademark Office Re.: U.S. Appl. No. 10/557,865.
Supplemental Notice of Allowability Dated Apr. 2, 2013 From the US Patent and Trademark Office Re. U.S. Appl. No. 12/373,937.
Supplemental Notice of Allowability Dated Mar. 5, 2014 From the US Patent and Trademark Office Re. U.S. Appl. No. 10/598,872.
Supplemental Notice of Allowability Dated Sep. 24, 2013 From the US Patent and Trademark Office Re. U.S. Appl. No. 11/886,248.
Supplemental Notice of Allowability Dated Apr. 27, 2010 From the US Patent and Trademark Office Re.: U.S. Appl. No. 10/557,865.
Supplementary European Search Report and the European Search Opinion Dated Oct. 21, 2013 From the European Patent Office Re. Application No. 06711327.4.
Translation of Decision for Rejection Dated Jun. 9, 2011 From the Japanese Patent Office Re. Application No. 2007-503495.
Translation of Notification of Reasons for Rejection Dated Jun. 1, 2010 From the Japanese Patent Office Re. Application No. 2006-531002.
Translation of Notification of Reasons for Rejection Dated Mar. 18, 2011 From the Japanese Patent Office Re. Application No. 2006-531002.
Translation of Notification of Reasons for Rejection Dated Dec. 24, 2010 From the Japanese Patent Office Re. Application No. 2007-503495.
Translation of Notification of Reasons of Rejection Dated Apr. 8, 2010 From the Japanese Patent Office Re.: Application No. 2007-503494.
Translation of Office Action Dated Mar. 5, 2013 From the State Intellectual Property Office of the People's Republic of China Re. Application No. 200980123856.5.
Translation of Office Action Dated May 6, 2013 From the State Intellectual Property Office of the People's Republic of China Re. Application No. 200780033622.2.
Translation of Office Action Dated Sep. 17, 2010 From the State Intellectual Property Office of the People's Republic of China Re.: Application No. 200680017262.2.
Translation of Office Action Dated Dec. 21, 2010 From the State Intellectual Property Office of the People's Republic of China Re. Application No. 200780033622.2.
Translation of Office Action Dated Aug. 22, 2013 From the State Intellectual Property Office of the People's Republic of China Re. Application No. 200780033622.2.
Translation of Office Action Dated Feb. 22, 2012 From the State Intellectual Property Office of the People's Republic of China Re. Application No. 200780033622.2.
Translation of Office Action Dated Nov. 22, 2012 From the State Intellectual Property Office of the People's Republic of China Re. Application No. 200780033622.2.
Translation of Office Action Dated Apr. 29, 2011 From the State Intellectual Property Office of the People's Republic of China Re.: Application No. 200680017262.2.
Translation of Office Action Dated Jan. 29, 2010 From the State Intellectual Property Office of the People's Republic of China Re.: Application No. 200680017262.2.
Translation of Reasons for Rejection Dated Mar. 18, 2013 From the Japanese Patent Office Re. Application No. 2011-223943.
Translation of Search Report Dated Nov. 22, 2012 From the State Intellectual Property Office of the People's Republic of China Re. Application No. 200780033622.2.
Written Opinion Dated Dec. 11, 2006 From the International Searching Authority Re.: Application No. PCT/IL06/00346.
Written Opinion Dated Apr. 14, 2008 From the International Searching Authority Re.: Application No. PCT/IL2007/000893.
Written Opinion Dated Nov. 22, 2005 From the International Searching Authority Re.: Application No. PCT/IL2004/000433.
Written Opinion Dated May 23, 2006 From the International Preliminary Examining Authority Re.: Application No. PCT/IL2005/000303.
Written Opinion Dated Sep. 23, 2005 From the International Searching Authority Re.: Application No. PCT/IL2005/000304.
Written Opinion Dated Oct. 24, 2008 From the International Searching Authority Re.: Application No. PCT/IL2008/000786.
Written Opinion Dated Mar. 25, 2009 From the International Searching Authority Re.: Application No. PCT/IL2008/001292.
Official Action Dated Nov. 25, 2014 From the US Patent and Trademark Office Re. U.S. Appl. No. 12/663,714.
Communication Pursuant to Articles 94(3) EPC Dated Feb. 8, 2016 From the European Patent Office Re. Application No. 14192972.9.
Communication Pursuant to Article 94(3) EPC Dated Jul. 29, 2015 From the European Patent Office Re. Application No. 11188150.4.
Office Action and Search Report Dated Apr. 5, 2016 From the State Intellectual Property Office of the People's Republic of China Re. Application No. 201510063512.7 and Its Translation Into English.
Office Action Dated Nov. 25, 2016 From the State Intellectual Property Office of the People's Republic of China Re. Application No. 201510063512.7 and Its Translation Into English. (16 Pages).

\* cited by examiner

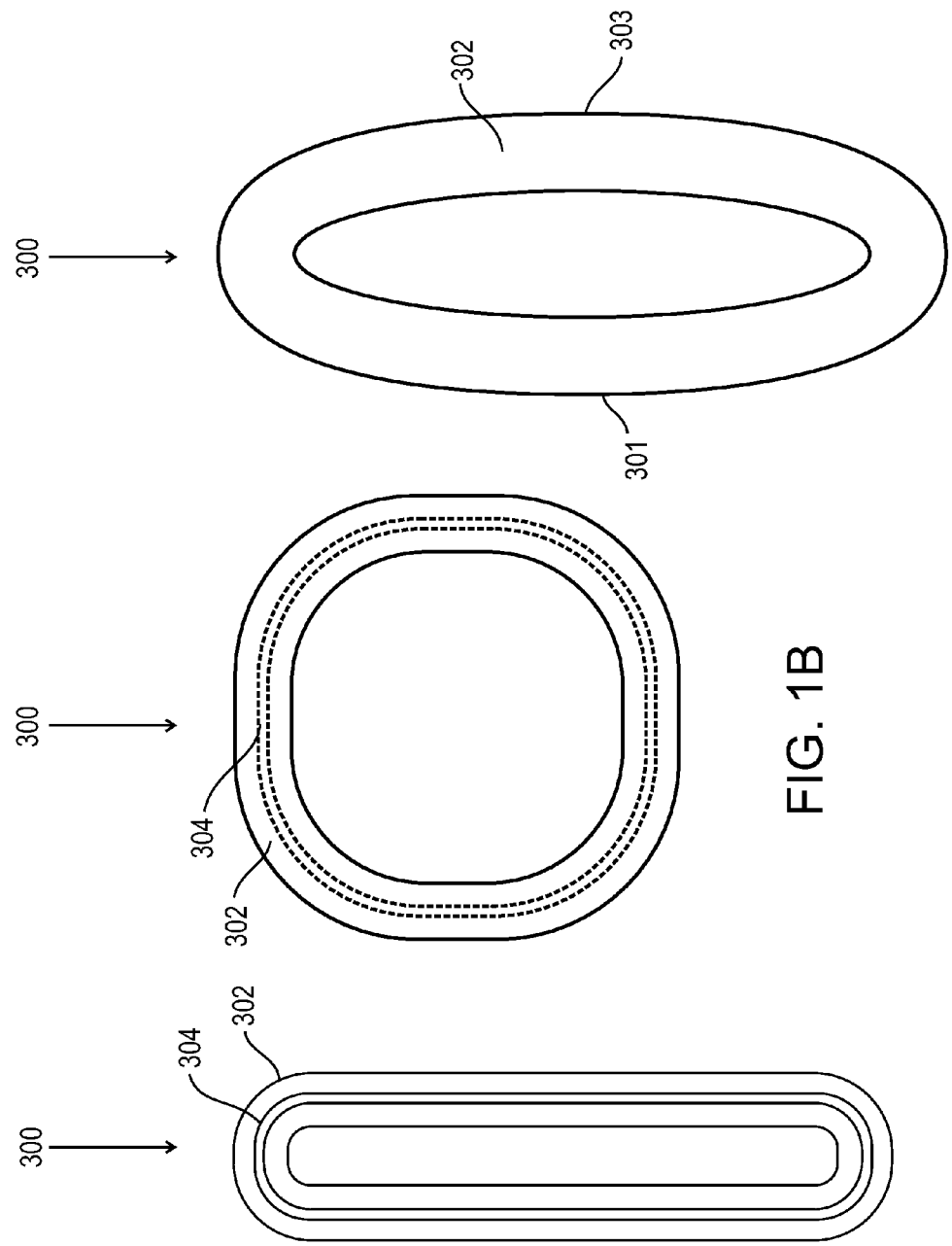

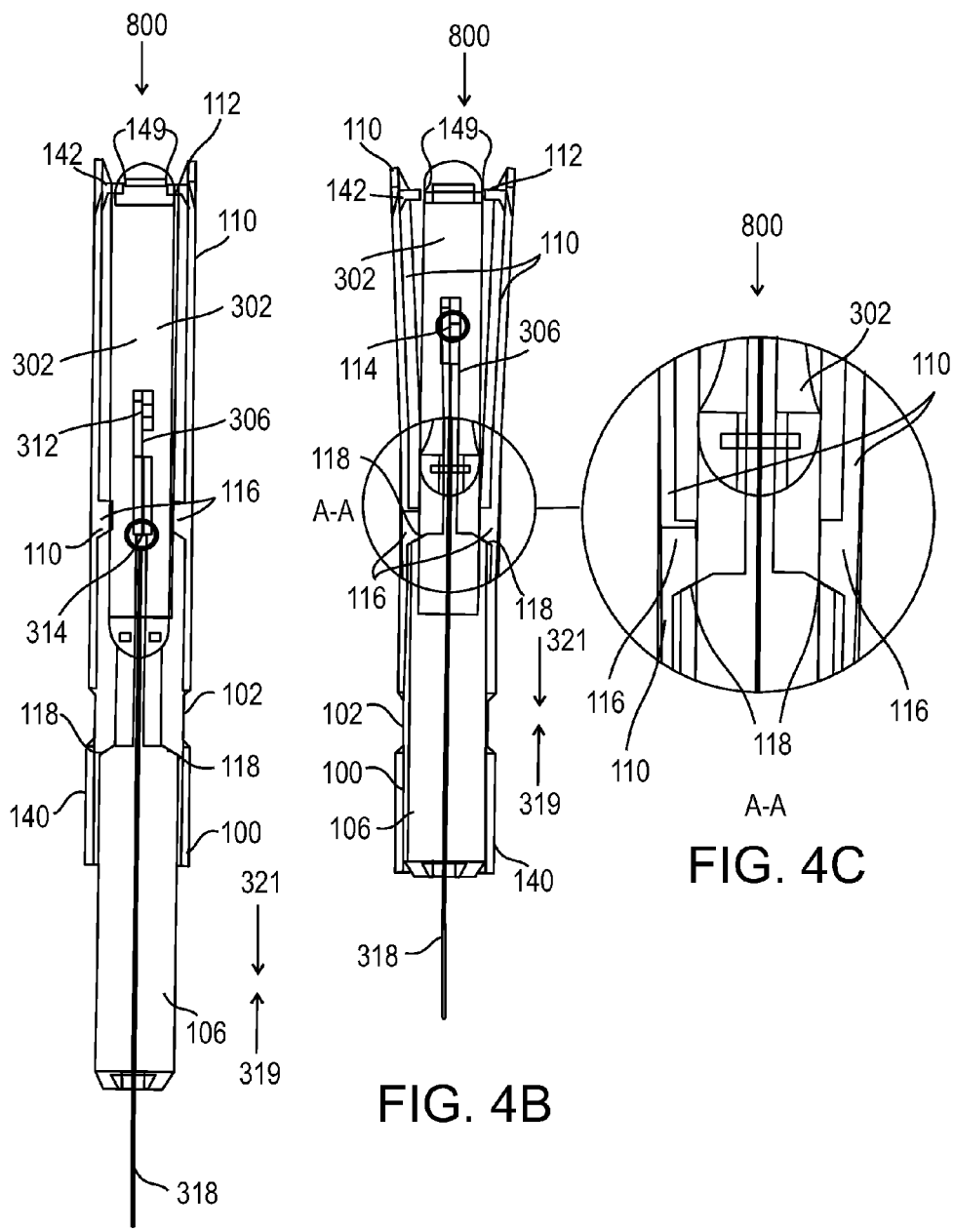

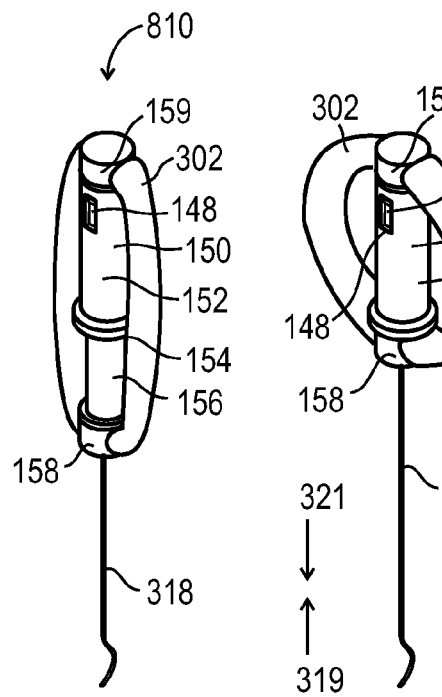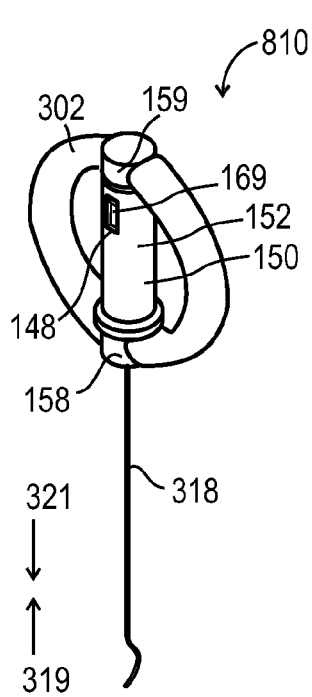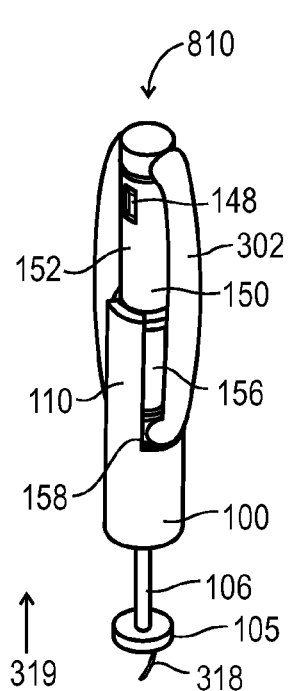
FIG. 5A    FIG. 5B    FIG. 5C
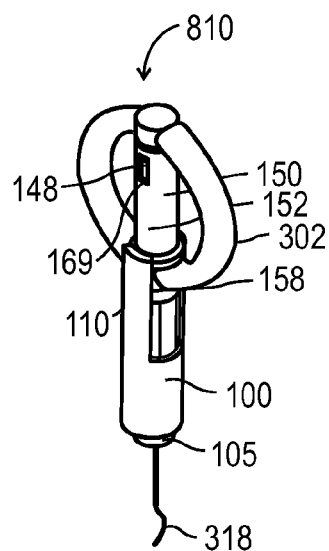
FIG. 5D

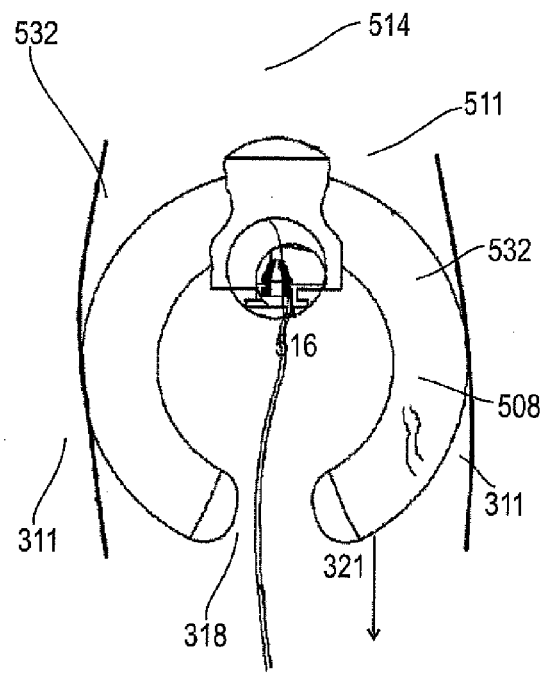
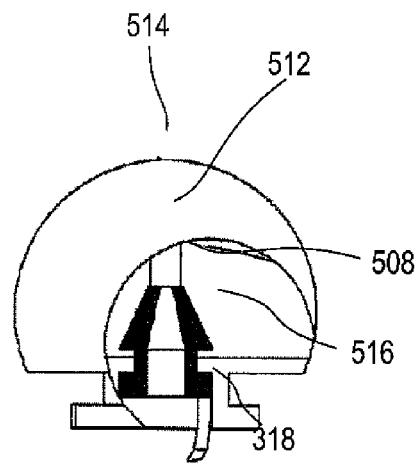
FIG. 17A　　　　FIG. 17B
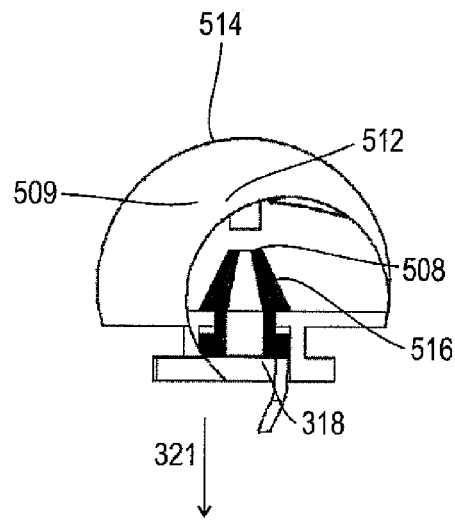
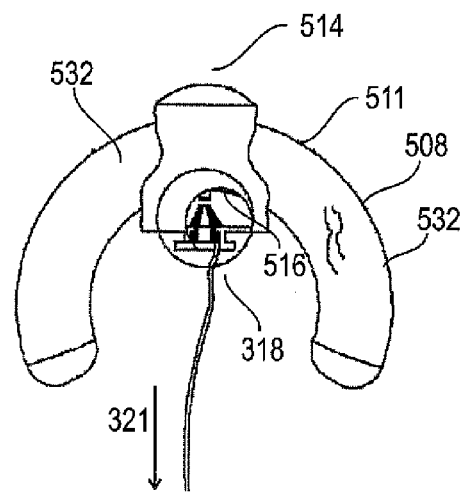
FIG. 18A　　　　FIG. 18B

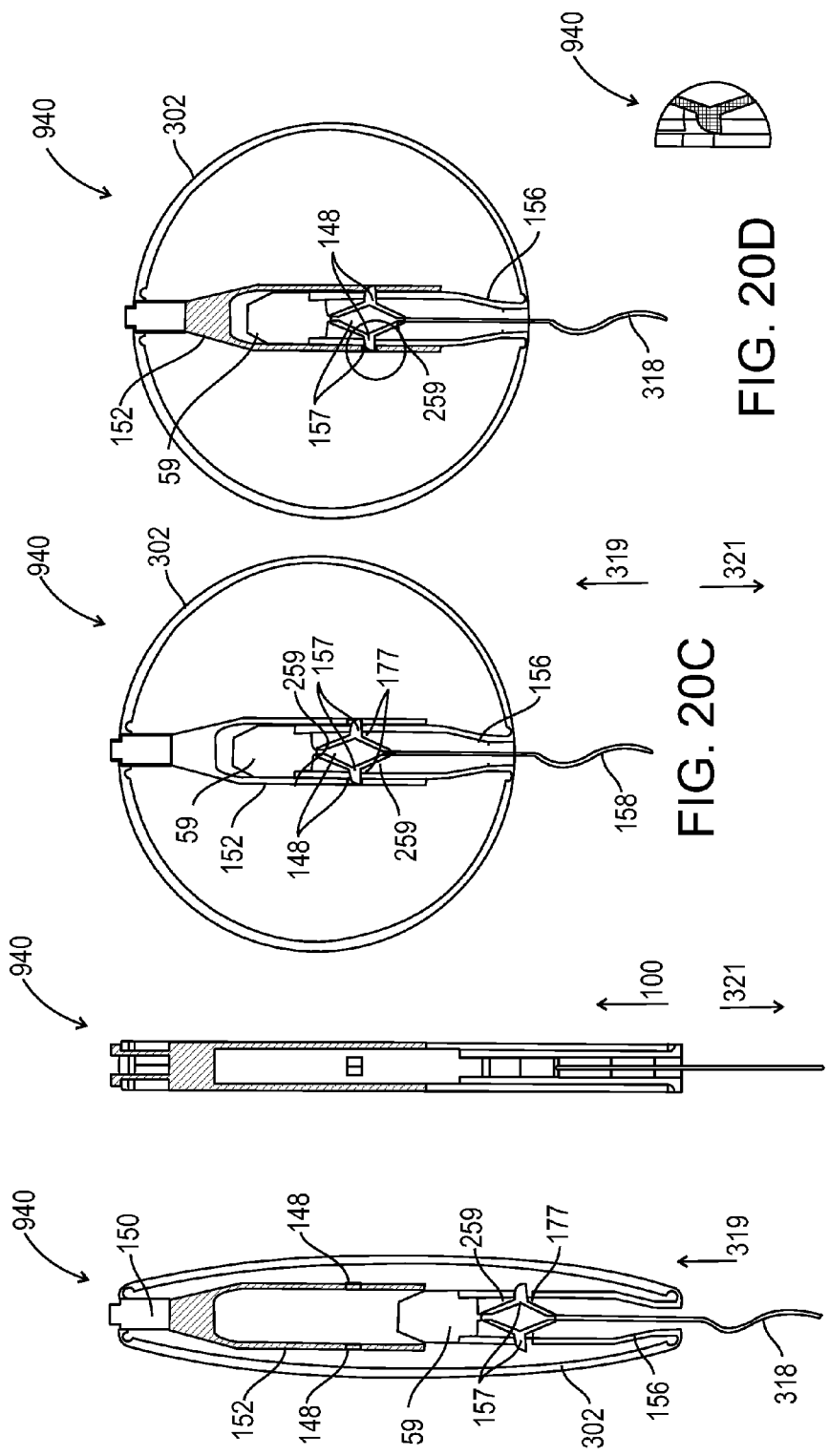

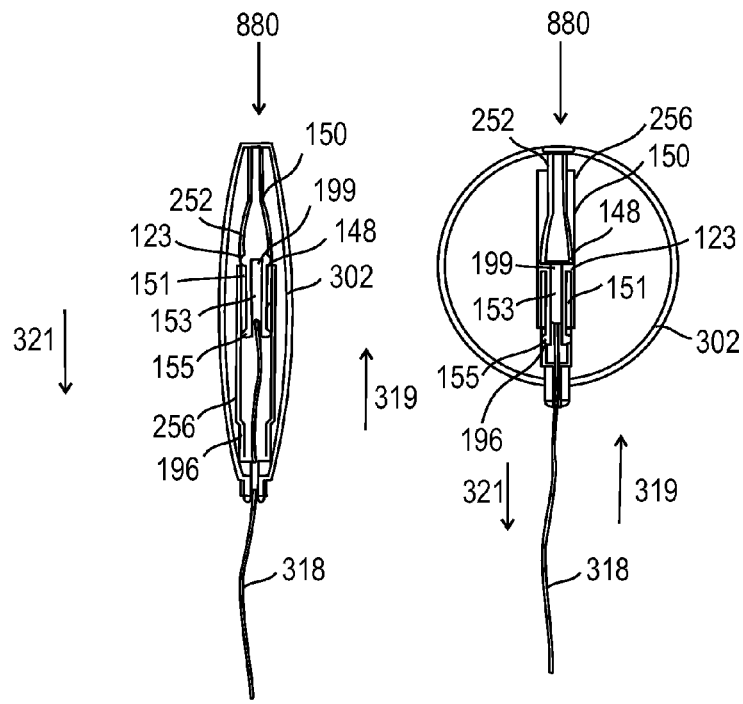
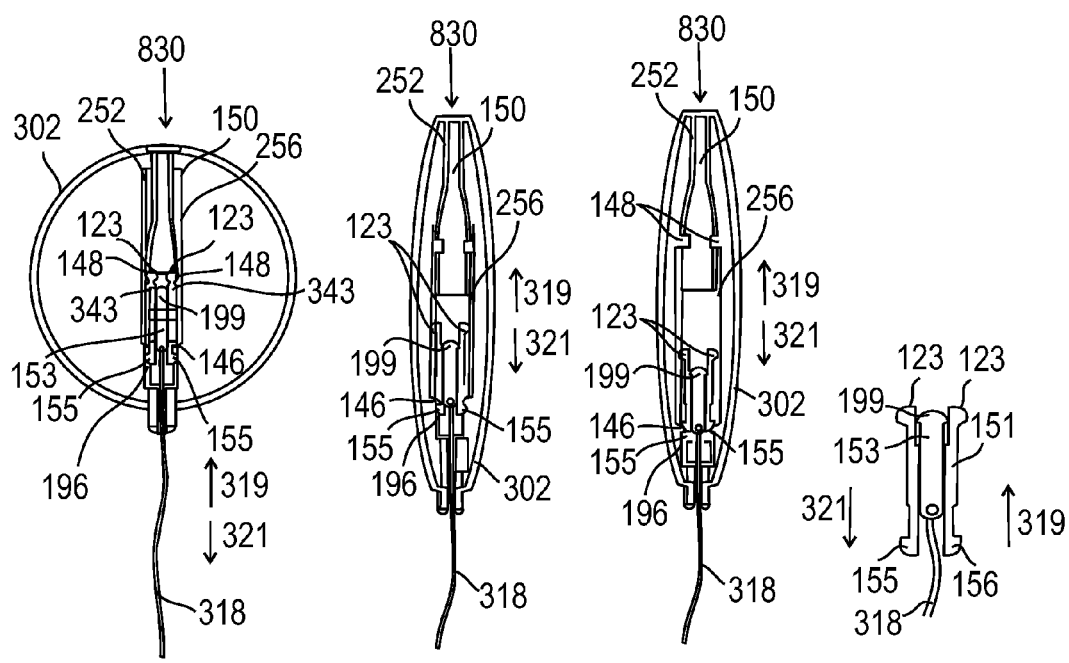
FIG. 21A  FIG. 21B
FIG. 21C  FIG. 21D  FIG. 21E  FIG. 21F

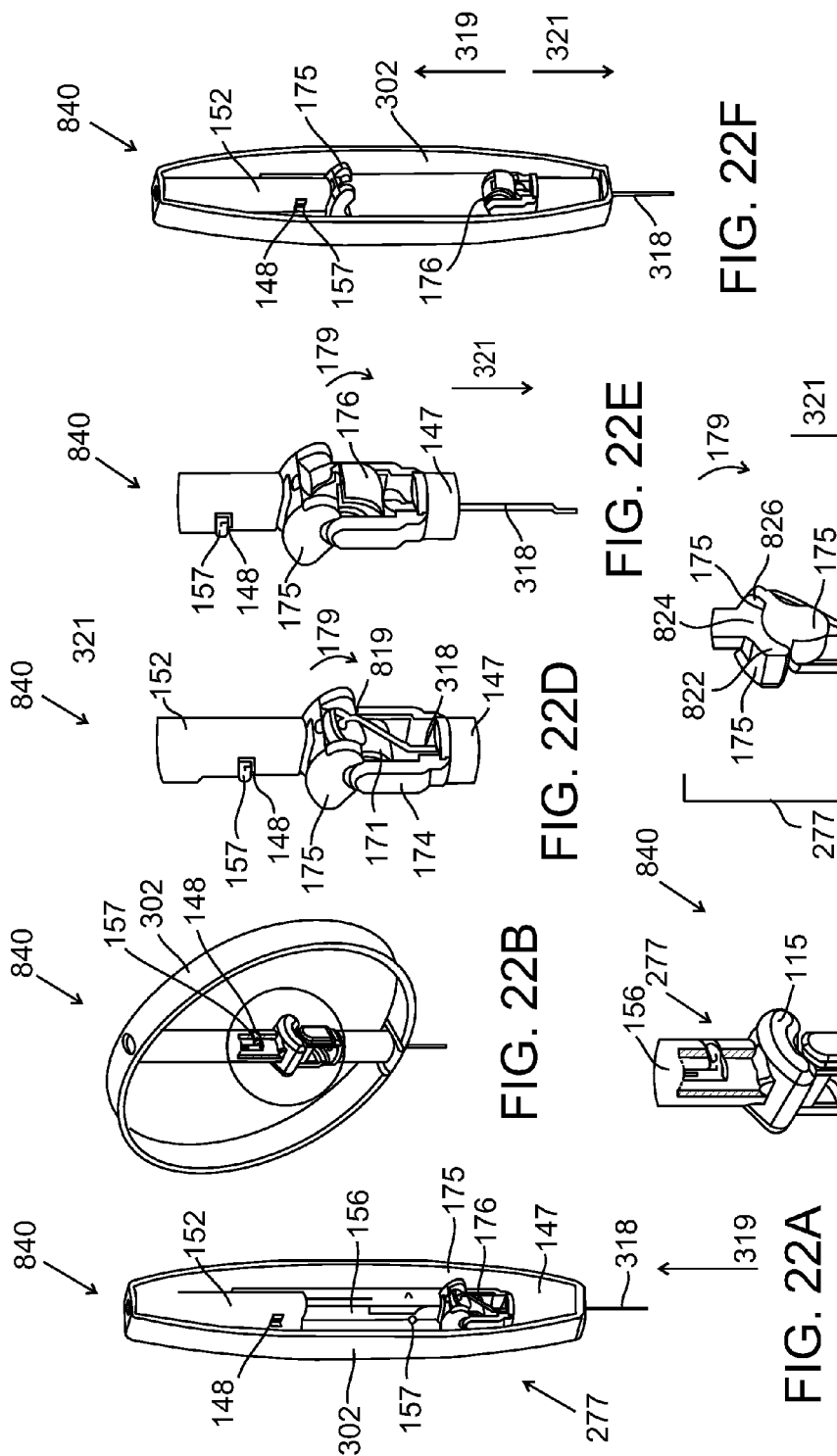

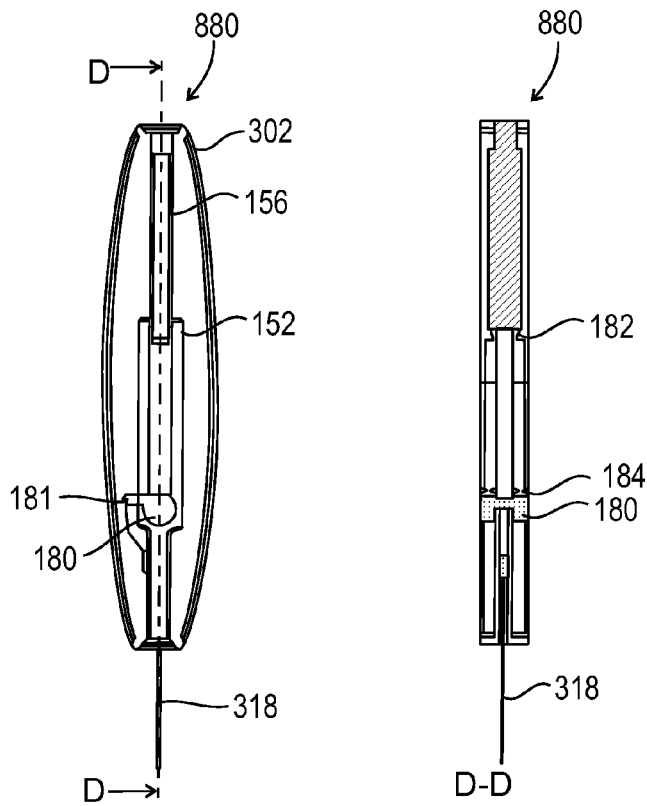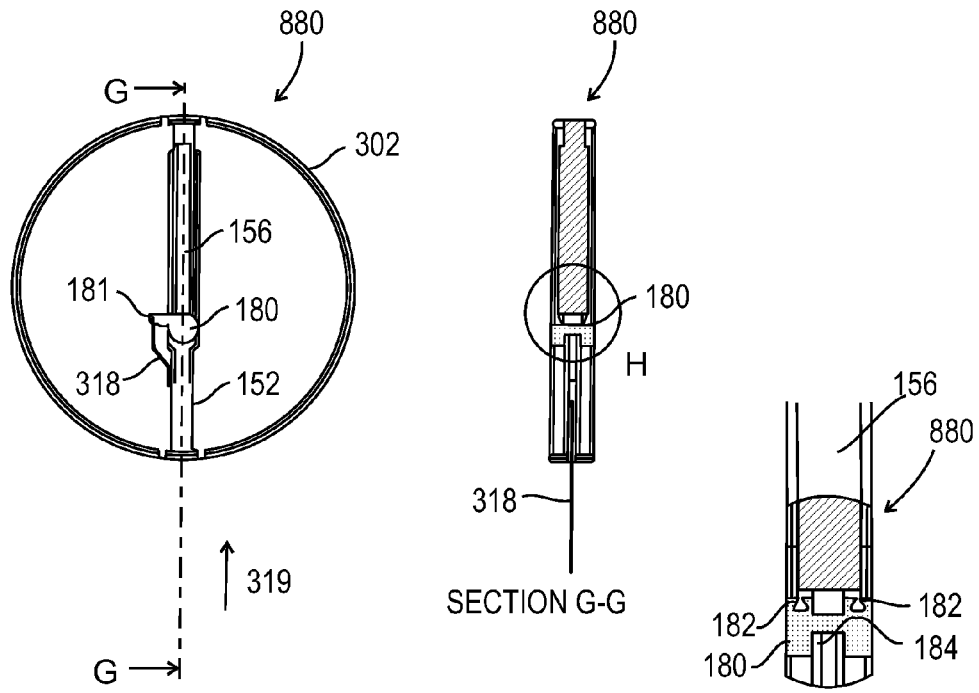
FIG. 23A  FIG. 23B  FIG. 23C  FIG. 23D  FIG. 23E

PESSARIES FOR PROLAPSE ALLEVIATION

RELATED APPLICATIONS

This application is a continuation of U.S. patent application Ser. No. 12/417,011 filed on Apr. 2, 2009, which claims the benefit of priority of U.S. Provisional Patent Application No. 61/071,344 filed on Apr. 23, 2008. The contents of the above applications are all incorporated by reference as if fully set forth herein in their entirety.

This application incorporates the contents of the following documents by reference as if fully set forth herein: PCT Patent Application No. PCT/IL2005/000303 filed on Mar. 17, 2005, which claims the benefit of priority of U.S. Provisional Patent Application No. 60/553,966 filed on Mar. 18, 2004.

FIELD AND BACKGROUND OF THE INVENTION

The present invention, in some embodiments thereof, relates to devices and methods for treating pelvic organ prolapse and, more particularly but not exclusively, to vaginal support devices and methods that aid in inserting vaginal support devices within the vagina.

Pelvic organ prolapse occurs when the network of muscles, ligaments, and tissues that hold the pelvic organs in place is weakened and one or more pelvic organs move into the vaginal cavity. Pelvic organ prolapse occurs as a result of normal aging, childbirth, pelvic surgery or trauma, and may include one or more of the following conditions:

i) Cystocele, the leading form of pelvic organ prolapse, wherein the bladder drops into the vagina and may be associated with urination problems;

ii) Rectocele, wherein the rectum herniates into the vagina and may result in difficulty and/or pain with defecation;

iii) Enterocele, wherein the small intestine prolapses into the vagina;

iv) Uterine prolapse wherein the uterus drops downward into the vagina and is often associated with complications related to childbirth; and v) Vaginal vault prolapse, wherein the top portion of the vagina, the apex, loses its natural shape and drops down into the lower vaginal canal, and may occur in women who had a hysterectomy.

To avoid surgical procedures to treat pelvic organ prolapse, a number of non-surgical vaginal devices, pessaries, have been designed to be inserted into the vagina by a surgeon, medical assistant or user.

Background art includes the following patents, the contents of all of which are incorporated by reference as if fully set forth herein:

WO 9601084: Inflatable Vaginal Pessary;
GB 235218: Inflatable Pessary;
FR 2843700: Rehabilitation Device for Urinary and Faecal Continence;
WO 03047476: Vaginal Pessary;
GB 1115727: Apparatus Controlling Incontinence in the Female;
U.S. Pat. No. 5,224,494: Vaginal Pessary;
U.S. Pat. No. 6,158,435: Pessary;
US 2003149334: Vaginal Pessary;
JP 6133996: Pessary for Treating Prolapse of Uterus;
U.S. Pat. No. 4,823,814: Pessary;
U.S. Pat. No. 5,771,899: Pessary;
U.S. Pat. No. 5,894,842: Pessary for Treating Vaginal Prolapse;
U.S. Pat. No. 6,158,435: Pessary;
U.S. Pat. No. 6,216,698: Flexible Pessary;
U.S. Pat. No. 6,503,190: Vaginal Pessary;
U.S. Pat. No. 6,808,485: Compressible Resilient Vaginal Incontinence Insert; and
U.S. Pat. No. 7,036,511: Vaginal Pessary.

SUMMARY OF THE INVENTION

According to one aspect of an embodiment of the present invention there is provided a device for supporting a prolapsed organ, the device including a ring-like body having a naturally occurring substantially flat and substantially planar compact configuration, the ring-like body configured with a size suitable for insertion into a vagina and to be expanded by a support element such that in the expanded configuration an outer periphery of the ring-like body contacts a portion of the vagina and stretches at least a portion of a prolapsed vaginal wall thereby substantially alleviating prolapse of at least one pelvic organ. The device optionally includes a support element including two moveably connected arms configured to support the ring in the expanded configuration.

In some embodiments of the invention, the support element is separate from the ring-like body.

In some embodiments of the invention, the two moveably connected arms are planar with the radial plane of the ring-like body in the substantially flat and planar compact configuration.

In some embodiments of the invention, in the expanded configuration the ring-like body is substantially flat and planar.

In some embodiments of the invention, the two moveably connected arms are planar with the radial plane of the ring-like body in the expanded configuration.

In some embodiments of the invention, the support element is substantially contained within the outer periphery when the ring-like body is in the naturally occurring substantially flat and planar compact configuration.

In some embodiments of the invention, the support element is substantially contained within the outer periphery when the ring-like body is in the expanded configuration.

In some embodiments of the invention, the two moveably connected arms are rotatably connected.

In some embodiments of the invention, when the ring-like body is in the expanded configuration the rotatable connection lies substantially along the radial plane of the ring-like body.

In some embodiments of the invention, the separate support element is configured to aid in expanding the ring-like body.

In some embodiments of the invention, each of the two rotatably connected arms is rotatably connected to the ring-like body with at least two rotatable connections.

In some embodiments of the invention, at least one of the at least two rotatable connections includes a projection that limits movement of the arms when the ring-like body is in the expanded configuration.

In some embodiments of the invention, the two moveably connected arms are elongate and aligned along a longitudinal axis when the ring-like body is in the naturally occurring substantially flat and planar compact configuration.

In some embodiments of the invention, the two moveably connected arms are longitudinally slideably connected.

In some embodiments of the invention, the two moveably connected arms align along a longitudinal axis when the ring-like body is in the expanded configuration.

In some embodiments of the invention, the device includes a lock that locks the position of the two moveably connected arms with respect to each other.

In some embodiments of the invention, the device includes a lock that maintains the two moveably connected arms in position when the ring-like body is in the expanded configuration.

In some embodiments of the invention, the lock includes a spring element having at least one laterally facing prong that engages at least one receptacle.

In some embodiments of the invention, the at least one laterally facing prong engages the at least one receptacle to lock the two moveably connected arms in position.

In some embodiments of the invention, the at least one laterally facing prong includes at least two laterally facing prongs.

In some embodiments of the invention, the at least one receptacle includes at least two receptacles.

In some embodiments of the invention, the spring element includes a U shape.

In some embodiments of the invention, the spring element includes a deformable rectangle.

In some embodiments of the invention, the at least one laterally facing prong includes at least four laterally facing prongs.

In some embodiments of the invention, the at least one receptacle includes at least four receptacles.

In some embodiments of the invention, the support element includes a trough-shaped connector having wide and narrow transverse portions and includes a separate clasp configured to be engaged by the narrow transverse portion when the ring-like body is in the expanded configuration.

In some embodiments of the invention, the trough-shaped connector is configured to move so that the wide transverse portion is substantially aligned with the clasp and release the clasp.

In some embodiments of the invention, the device includes a lever arm connected to the trough-shaped connector and configured to cause the trough-shaped connector to move.

In some embodiments of the invention, the support element includes a trough-shaped connector having a wide transverse portion that includes a separate clasp, the trough configured to move so that the wide transverse portion is substantially aligned with the clasp and releases the clasp.

In some embodiments of the invention, upon releasing the clasp, the two moveably connected arms remain locked with respect to each other.

In some embodiments of the invention, the separate support element includes a ratchet mechanism including an elongate element including at least two ratchets and includes a ratchet clasp configured to engage the at least two ratchets.

In some embodiments of the invention, the ratchet clasp is configured to engage the at least two ratchets to maintain the ring-like body in an expanded configuration.

In some embodiments of the invention, the ratchet clasp is configured to disengage from the at least two ratchets to allow the ring-like body to return to the naturally occurring substantially flat and planar compact configuration.

In some embodiments of the invention, the elongate element includes a collapsible hollow chamber containing a slidable support piece and the collapsible hollow chamber is configured to collapse upon removing the slidable support piece from the hollow chamber allowing the disengagement.

In some embodiments of the invention, upon the collapse of the collapsible hollow chamber, the ratchet clasp is configured to disengage from the at least two ratchets.

In some embodiments of the invention, the device includes a string connected to the support element, the string configured to be pulled to remove the support by the support element.

In some embodiments of the invention, the device includes an applicator configured to removably connect to the ring-like body when the ring-like body is in the naturally occurring substantially flat and planar compact configuration.

In some embodiments of the invention, the applicator is configured to release the ring-like body when the ring-like body is in the expanded configuration.

In some embodiments of the invention, the applicator is additionally configured to aid in expanding the ring-like body from the compact configuration to the expanded configuration.

In some embodiments of the invention, in the expanded configuration the ring-like body includes an inner periphery defining a space having a size sufficient to allow passage of vaginal fluids.

In some embodiments of the invention, in the substantially flat and planar compact configuration, the outer periphery of the ring-like body has a shape of at least one of an oval, a triangle, and a rhomboid.

In some embodiments of the invention, in the expanded configuration, the outer periphery of the ring-like body assumes a shape of at least one of a circle, a square, an oval, and a rhomboid.

In some embodiments of the invention, the prolapsed organ includes at least one of a vaginal vault, a bladder, a rectum, a small intestine, and a uterus.

According to another aspect of an embodiment of the present invention there is provided device for supporting a prolapsed organ, the device including at least two operatively associated elongate elements having at least two configurations, a collapsed configuration having a cumulative size suitable for insertion into a vagina, and an expanded configuration wherein each of the at least two operatively associated elongate elements extend laterally to press two opposite walls of the vagina and stretch at least a portion of a prolapsed vaginal wall thereby substantially alleviating prolapse of at least one pelvic organ, and a support element configured to maintain a distance between the at least two operatively associated elongate elements in the expanded configuration.

In some embodiments of the invention, the at least two operatively associated elongate elements are planar in the expanded configuration.

In some embodiments of the invention, the support element is planar with the at least two operatively associated elongate elements in the expanded configuration.

In some embodiments of the invention, the at least two operatively associated elongate elements are planar in the collapsed configuration.

In some embodiments of the invention, the support element is planar with at least two operatively associated elongate elements in the collapsed configuration.

According to an additional aspect of an embodiment of the present invention there is provided a device for supporting a prolapsed organ, the device including an inflatable body including at least two arms having at least two configurations, an uninflated configuration having a size suitable for insertion into a vagina and an inflated configuration in which at least a portion of the inflatable body contacts at least a portion of the vagina and stretches at least a portion of a prolapsed vaginal wall thereby substantially alleviating prolapse of at least one pelvic organ, and a housing connected to the inflatable body and configured to substantially contain the at least two arms in the uninflated configuration.

In some embodiments of the invention, the device includes a one-way inflation valve operatively associated with the housing.

In some embodiments of the invention, the one-way inflation remains operatively associated with the housing in the vagina.

In some embodiments of the invention, the device includes an inflator removably connected to the one-way inflation valve, the inflator configured to inflate the inflatable body.

In some embodiments of the invention, the inflator includes a substantially rigid body configured to aid in inserting the inflatable body into the vagina.

In some embodiments of the invention, the inflator is configured to disconnect from the inflatable body following inflation of the inflatable body.

In some embodiments of the invention, the inflator additionally is configured to aid in inserting the inflatable body into the vagina.

According to still another aspect of an embodiment of the present invention there is provided a device for supporting a prolapsed organ, the device including a ring-like body having a naturally occurring substantially flat and planar compact shape, the ring-like body configured with a size suitable for insertion into a vagina and to be expanded such that in the expanded configuration an outer periphery of the ring-like body contacts a portion of the vagina and supports at least a portion of a prolapsed organ, and at least one support element substantially integral to the ring-like body in the naturally occurring substantially flat and planar compact shape the at least one support element configured to support the ring-like body in the expanded configuration.

In some embodiments of the invention, the support element is substantially integral to the ring-like body when the ring-like body is in the expanded configuration.

According to a still additional aspect of an embodiment of the present invention there is provided a method for supporting a pelvic organ, the method including placing a ring-like body having a flat and planar compact shape in a vagina, expanding the ring-like body to stretch at least a portion of a prolapsed vaginal wall thereby substantially alleviating prolapse of at least one pelvic organ, and supporting the expanded ring-like body with a support element including two arms.

In some embodiments of the invention, the method includes pulling a string connected to the support element to collapse the support element.

In some embodiments of the invention, the method includes returning the ring-like body to the flat and planar compact shape.

In some embodiments of the invention, the arms are rotatably connected.

In some embodiments of the invention, the arms are slidingly connected.

In some embodiments of the invention, the support element is separate from the ring-like body.

There is provided in accordance with an exemplary embodiment of the invention, a vaginal pessary sized and shaped for alleviating organ prolapse, comprising:
(a) a body including at least two rib sections adapted to, at least in one state, extend along a vaginal axis and apply force to facing vaginal walls along axial extents thereof, wherein said body is adapted to be in at least two states:
(i) a compressed state in which said body is sized for insertion into said vagina; and
(ii) an expanded state in which said body is sized and stiff enough for providing organ prolapse alleviation and in which state said ribs extend along a vaginal axis and apply force to facing vaginal walls; and
(b) a state changing mechanism integral to said pessary and configured to change a configuration of said body from one state to the other state, which mechanism does not use fluid flow to cause state change,
wherein said pessary is stable in shape and size in both states.

In an exemplary embodiment of the invention, said ribs are adapted to contact said walls for a length of at least 30% of a length of said body along said vaginal axis.

Optionally or alternatively, said ribs are supported at either end thereof by said body. Optionally or alternatively, said ribs state change mechanism spaces apart said ribs during a change from said compressed state to said expanded state.

Optionally or alternatively, said body in said expanded state alleviates organ prolapse by stretching the vagina in a direction orthogonal to an organ prolapse direction. Optionally or alternatively, said body in said expanded state alleviates organ prolapse by directly supporting a prolapsed organ.

In an exemplary embodiment of the invention, said body is substantially rigid in said expanded state. Optionally or alternatively, said body includes at least one flexible section at at least one of said states.

In an exemplary embodiment of the invention, said state changing mechanism stabilizes said pessary in said two states.

In an exemplary embodiment of the invention, said state changing mechanism locks said pessary in at least one of said two states. Optionally, said locked state comprises said expanded state. Optionally or alternatively, said state changing mechanism locks said pessary in both of said states.

In an exemplary embodiment of the invention, said pessary has at least three different stable shapes with different geometries of said body.

In an exemplary embodiment of the invention, the pessary comprises at least one elastic element which urges said pessary towards at least one of said states. Optionally, said elastic element urges said pessary towards a selected one of said states, based on a starting configuration of said pessary.

In an exemplary embodiment of the invention, said state changing mechanism is configured to become dysfunctional after a number of state changes. Optionally or alternatively, said body is a space filling body extending in at least two orthogonal directions not along the vaginal axis. Optionally, said body comprises a plurality of orthogonal planar shapes. Optionally, said plurality of shapes change state together by means of a single state changing mechanism.

In an exemplary embodiment of the invention, said body is substantially planar. Optionally, said body is horse-shoe like. Alternatively, said body comprises two spaced apart substantially parallel rib sections.

In an exemplary embodiment of the invention, said body is a closed shape including said two rib sections.

In an exemplary embodiment of the invention, said body is ring-like. Optionally, said body comprises at least two arc sections connected by joints.

In an exemplary embodiment of the invention, said body defines a border and comprising at least one membrane stretched on at least part of said border.

In an exemplary embodiment of the invention, at least one of said rib sections is arranged so that in said expanded state it extends at an angle to said vaginal axis.

In an exemplary embodiment of the invention, said body includes at least one lockable joint enclosed thereby.

In an exemplary embodiment of the invention, said state changing mechanism is at least mostly enclosed by said body.

In an exemplary embodiment of the invention, said state changing mechanism is at least mostly unenclosed by said body. Optionally, said state changing mechanism is parallel to said vaginal axis. Optionally or alternatively, said state changing mechanism is perpendicular to said vaginal axis.

In an exemplary embodiment of the invention, said state changing mechanism resists a shape change of said body.

In an exemplary embodiment of the invention, said state changing mechanism comprises a ratchet mechanism.

In an exemplary embodiment of the invention, said state changing mechanism comprises a locking element and an elastic element pre-configured to move said locking element to a locking condition.

In an exemplary embodiment of the invention, said state changing mechanism comprises a gear.

In an exemplary embodiment of the invention, said state changing mechanism comprises a rotating locking element.

In an exemplary embodiment of the invention, said state changing mechanism comprises an interference locking element.

In an exemplary embodiment of the invention, the pessary comprises a control coupled to said state-changing element and configured to activate a state change when said control is pulled when inside a body.

In an exemplary embodiment of the invention, said pessary is functionally rotationally symmetric around said vaginal axis.

In an exemplary embodiment of the invention, said body consists essentially of one or more rods.

In an exemplary embodiment of the invention, said body allows flow of vaginal secretions therepast.

In an exemplary embodiment of the invention, said pessary is mounted on an applicator.

There is also provided in accordance with an exemplary embodiment of the invention, a pessary system comprising:
 (a) a shape changing pessary adapted to alleviate organ prolapse when deployed in a vagina; and
 (b) an applicator adapted for holding said pessary while in a form suitable for insertion into a vagina.

In an exemplary embodiment of the invention, said applicator is configured to actively change a shape of said pessary after insertion thereof into a vagina.

There is also provided in accordance with an exemplary embodiment of the invention, a vaginal pessary sized and shaped for alleviating organ prolapse, comprising:
 (a) a body comprising a frame formed of at least one elongate thin element and adapted to, at least in one state, extend along a vaginal axis and apply force to facing vaginal walls along axial extents thereof, wherein said body is adapted to be in at least two states:
  (i) a compressed state in which said body is sized for insertion into said vagina; and
  (ii) an expanded state in which said body is sized and stiff enough for providing organ prolapse alleviation and in which state said frame extends along a vaginal axis and applies force to facing vaginal walls; and
 (b) a state changing mechanism integral to said pessary and configured to change a configuration of said body from one state to the other state. Optionally, said state changing mechanism is fluid-based.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1C and 2A-2E show portions and operation of a pessary including a body having a naturally occurring unexpanded shape, according to some embodiments of the present invention;

FIGS. 3A-3E, 4A-4C, 5A-5D, 6A-6B, 7A-7B, 8A-8B, 9A-9C, 10A-10C, 11A-11C, 12A-12H, 13A-13G, 14A-14D, 15A-15D, 20A-20E, 21A-21F, 22A-22G, and 23A-23H show alternative configurations and operation of the pessary of FIGS. 1A-1C and 2A-2E, according to some embodiments of the present invention;

FIGS. 16A-16B, 17A-17B, and 18A-18B show portions and operation of a pessary including an inflatable body, according to some embodiments of the present invention;

DESCRIPTION OF SPECIFIC EMBODIMENTS OF THE INVENTION

Figure 2A:
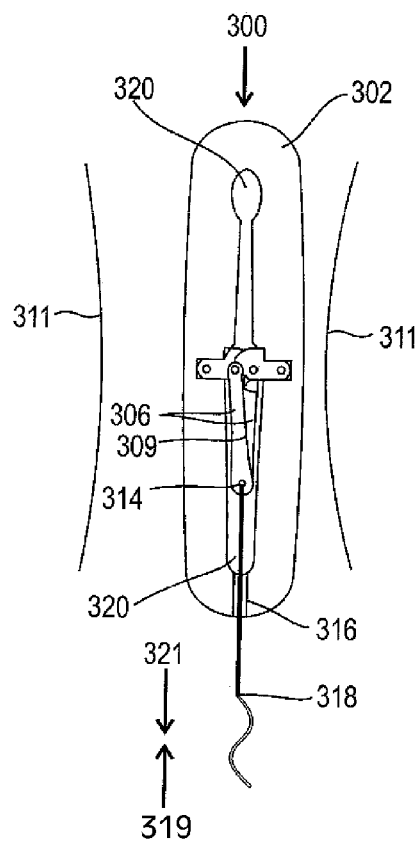

The present invention, in some embodiments thereof, relates to devices and methods for treating pelvic organ prolapse and, more particularly but not exclusively, to vaginal support devices, and methods that aid in inserting the support devices into the vagina.

In an exemplary embodiment of the invention, the pessary includes two or more rib sections that push apart facing vaginal walls. As shown below, in many embodiments, the ribs are simply parts of a ring, which contact a vaginal wall. In an exemplary embodiment of the invention, the pessary has two stable states: a compressed state suitable for insertion and/or removal and an expanded state where the ribs press against the walls. Optionally, the pessary includes an integrate state changing mechanism which changes the pessary from one state to another and/or locks the pessary in one or both states. Separate locks and state changing mechanism may be provided. Optionally or alternatively, one or more elastic elements are provided to maintain the stability of the pessary and/or to urge the pessary to a stable state.

Optionally, multiple deployed states are provided, for example, for adjustment of size and/or prolapse alleviation, as needed.

In an exemplary embodiment of the invention, the ribs are stiffened by the state changing mechanism.

Optionally, one or more parts of the pessary, for example, the state changing mechanism are configured to become dysfunctional after one or more uses, for example, including included sections that support only one direction of relative motion, or including one or more pins that break during state change.

Optionally, the ribs are contained within a shape, for example, a ring. In an exemplary embodiment of the invention, the ribs contact and apply substantial force to the vaginal walls for a length that is at least 20%, 30%, 40%, 50%, 60%, 70% or more of the total axial length of the device, or its non-pliable portions (e.g., not including a string or control cable or rod). Optionally, the length of force application of each rib is at least 10 mm, 20 mm, 30 mm, 40 mm, 50 mm or shorter, intermediate or longer distances.

In an exemplary embodiment of the invention, the ribs are substantially rigid in form and location when in a deployed state. Optionally or alternatively, some part of the pessary, for example, the rings or a section supporting or otherwise coupled to the ribs, can flex.

In some embodiments of the invention, prolapse alleviation is provided by a membrane or other element (e.g., state change mechanism) which extends between the ribs and prevents motion past it of a vaginal wall section. The ribs optionally act as anchors and/or to stretch the vaginal wall.

In some embodiments of the invention, the pessary is planar. In other embodiments, the pessary is non-planar and fills a volume within the vagina, for example, a volume of 2, 3, 4, 5, or more cm in height (e.g., along a general left-right symmetry plane of the body, and perpendicular to the vaginal axis). Optionally, such a pessary is formed by using one or more state change mechanisms, as applied to two or more planar elements. Optionally or alternatively, such a structure is of an inflated element.

In an exemplary embodiment of the invention, a planar and/or a volumetric pessary are made rotationally symmetric, for example, by rotation of 180 or 90 or 60 or 45 degrees a substantially same functional effect is achieved. This may assist in placement.

In an exemplary embodiment of the invention, the pessary is not space filling, rather it is formed mainly of one or more rods or other elongated forms which provide the final geometry. The spaces between the elongate forms are optionally open and/or otherwise allow passage of vaginal secretions past the pessary. For example, the pessary may fill less than 40% 30%, 20%, 10% of a volumetric shape defined thereby. In an exemplary embodiment of the invention, the pessary is formed so that the vaginal walls tent on the pessary. Optionally, no cover is provided. Alternatively, a cover is provided.

In an exemplary embodiment of the invention, the pessary is inserted using an applicator. Optionally, the applicator changes the state of the pessary. Optionally or alternatively, the pessary is stored in the applicator in a tension reduced state. Optionally, the applicator is used to change the state of the pessary after insertion. Such an applicator may also be used for pessaries without a state changing mechanism as described herein, and provide a potential advantage with respect to ease of use and/or self insertion. Optionally or alternatively, an applicator and/or the state changing mechanism and/or a tearing mechanism (e.g., which causes mechanical failure of the pessary by reduction of hydraulic pressure or mechanical disconnection or weakening), is used to provide ease of removal, for example, for self removal.

There is provided a variety of embodiments of a pessary for supporting a prolapsed pelvic organ. In an exemplary embodiment of the invention, the pessary includes a ring having a naturally occurring (in a rest state) substantially flat and planar compact shape and size that is suitable for insertion into a vagina. Optionally, the ring is not-ring like in its resting shape, for example, being ovoid, for example, having a width to length ration of smaller than 1:2, 1:3, 1:5, 1:6, 1:10. In some embodiments of the invention, the use of a flat compact shape assists in insertion to the body. Optionally, the use of a natural compact shape allows the insertion to be provided without apply shape-maintaining forces on the device. In some embodiments of the invention, the pessary is elastic or pliable enough so it may be further manually compacted or distorted to assist in insertion.

In some embodiments of the invention, when deployed, the pessary extends out of a single plane, by, for example, 10%, 20%, 30% or intermediate or smaller amounts of an average or maximal thickness of the pessary. Optionally, the ratio of thickness (in the plane) to diameter is smaller than for example, 1:3 (thickness to diameter), 1:4, 1:5, 1:6, 1:8, 1:10 or intermediate or smaller ratios.

In an exemplary embodiment of the invention, the ring is configured to be maintained by a support element in a laterally expanded configuration. In the laterally expanded configuration, the ring assumes a predefined shape and size (such as a ring shape or generally polygonal annular shape), and exerts outward pressure on at least two opposite vaginal walls, optionally creating linear stretching, while creating a new shape of the intra-vaginal hollow, for example a rectangular shape. The pressure from the ring causes the vaginal walls and apex to stiffen, thereby substantially supporting the prolapsed pelvic organ and relieving the discomfort caused by the prolapsed organ.

Optionally, the ring gives (e.g., the diameter lessens and/or ring bends out of a more planer shape) only a small amount or not at all when in an expanded shape, for example, less than 5 mm, less than 3 mm, less than 1 mm. Alternatively, the ring is elastically maintained in its expanded shape and can give a greater amount, for example, 6 mm, 7 mm, 8 mm, 9 mm or more.

In some embodiments of the invention, the support element is encapsulated within the ring. Optionally or alternatively, the support element is outside of the body of the ring, for example, forming a chord.

In an exemplary embodiment of the invention, at least 50%, 70%, 85% or intermediate percentages by volume of the support element are contained within the outer periphery of the ring-like body.

In an exemplary embodiment of the invention, at least 30%, 50%, 70%, 80% or intermediate percentages or more of the volume enclosed by the pessary when in an expanded shape, is a void, optionally a void accessible form outside the pessary, optionally void that connects two opposing faces of the pessary.

In some embodiments of the invention, the ring includes a resilient material that naturally maintains the compact configuration.

In some embodiments of the invention, the ring's naturally occurring compact shape comprises an oval, a triangle, or a rhomboid.

In some embodiments of the invention, in the expanded configuration, the ring includes an aperture of sufficient size to allow passage of vaginal fluids thereby increasing user comfort and preventing fluid buildup that can result in malodors or infections.

In some embodiments of the invention, in the expanded configuration, the outer periphery of the ring assumes a circular, an ovoid or a rhomboid shape.

In some embodiments of the invention, the support element includes dual bars that are centrally connected at their first ends, and rotatably connected at their second ends to the ring. With the ring in the collapsed position, the bars are in a folded position. The compact ring has a long axis which, when pressed, causes the ring to expand as the bars extend.

Optionally, the bars include locking mechanisms, for example extensions in the rotatable connections at the second ends of the bars, which maintain the bars in the extended position, thereby maintaining the ring in the expanded configuration.

In some embodiments of the invention, the pessary includes a string connected to the central rotatable connection of the dual bars. The string extends from the vagina, such that pulling the string by the user causes the bars to unlock. With the bars unlocked, the resilience of the ring causes the bars to fold, and the ring assumes the naturally occurring substantially flat and planar compact shape, alternatively referred to herein as an unexpanded shape; a configuration that is easily removed from the vagina.

There are presented multiple alternative embodiments in which the support element includes telescoping tubes (or side by side bypassing tubes) which, when the ring is in the compact configuration, are in a non-telescoped and extended position. With the ring in the expanded configuration, the tubes telescope, one within the other (or side by side), and locks between the tubes maintain the telescoped position so that the pessary is maintained in the expanded configuration.

Unlocking the locks allows the ring to return to the compact configuration while the tubes extend with respect to each other to the non-telescoped configuration.

In an exemplary embodiment of the invention, the support elements is configured to be unlocked by application of minimal force, with some unlocking being provided by the resilience and natural shape of the ring. Alternatively, unlocking of the support element requires application of force for a significant change in shape of the support element, for example, a movement of at least one part of the support element relative to other parts, of at least 5 mm, 10 mm, 20 mm or more.

There are a variety of support element lock embodiments presented that lock the telescoping tubes in the telescoped configuration and maintain the ring in the expanded configuration.

In some support element lock embodiments, the support element lock comprises a "U" shape element having prongs that engage receptacles to lock the tubes in the telescoped position. Pulling a string connected to the U shape element causes the prongs to disengage from the receptacles so that the ring returns to a naturally occurring compact configuration.

In some support element lock embodiments, interconnected prongs extend laterally from lateral aspects of a diamond-shaped spring. Pulling a string connected to the diamond causes the diamond shape to narrow, disengaging the prongs from the receptacles, allowing the ring to return to the compact configuration.

In some support element lock embodiments, prongs extend laterally from upper and lower ends of a spring that is shaped like an "H". A slide bar between the arms of the "H" presses the prongs into receptacles, thereby locking the ring in the expanded configuration.

Pulling a string connected to the slide bar causes disengagement of the upper prongs of the H spring from the upper receptacles, unlocking and allowing movement of the inner tube with respect to the outer tube and the ring returns to the compact configuration.

In some support element lock embodiments, the lock includes a wheel connected to a lower portion of the ring. The wheel includes a rim that is engaged by edges of a semi-circular piece attached to an upper portion of the ring.

The edges of the semi-circular piece include a narrow transverse dimension that engages the wheel rim. These edges optionally include a release portion having a wide transverse dimension that releases the wheel rim, when so disposed, to allow the ring to return to the compact configuration.

To compact the ring, the semi-circular pieces are rotated so that the release portion of the semi-circular piece is aligned with the wheel rim and the wheel is released. The wheel disengages from the semi-circular piece, and the telescoped inner and outer tubes, along with the semi-circular piece, retract upward. The wheel retracts downward and remains connected to the lower part of the ring which returns to the compact configuration.

In additional support element lock embodiments, the lock comprises a wheel having a lever-like extension, and wide and narrow transverse dimensions. The wheel is rotatably attached to the large diameter tube. The small diameter narrow tube includes engagement rails which engage the narrow wheel dimension to maintain the tubes in the telescoped configuration.

To compact the ring, the lever is pulled to rotate the wheel so that the wide release portion aligns with the engagement rail, releases the engagement rail, and allows the ring to return to the compact configuration.

In some embodiments of the invention, the support element lock comprises a one-way valve that causes a vacuum to form within the tubes. In the telescoped configuration, the vacuum locks the tubes and maintains the expanded shape of the ring. Releasing the one-way valve allows the ring to assume the compact position with the telescoped tubes extended.

In some embodiments of the invention, the support element lock comprises a collapsible elongate ratchet that extends from an upper ring portion that interfaces with a ratchet lock extending from a lower ring portion. The collapsible elongate ratchet includes a collapsible tubular chamber that slidably surrounds a rod. With the rod in the tubular chamber, the chamber and the ratchets are maintained in a laterally expanded position.

During expansion, the ratchet lock ratchets along the ratchets until the ring is fully expanded and the ratchet lock is locked in place by the ratchets.

To compact the ring, the rod is pulled out of the tubular chamber so the ratchets collapse inward and no longer interface with the ratchet lock. The ring returns to the compact configuration while the prongs slide past the collapsed ratchets.

According to some embodiments of the invention, there is provided a dual arm pessary for supporting a prolapsed organ.

The dual arm pessary includes two operatively associated elongate elements having at least two configurations: a collapsed configuration having a cumulative size suitable for insertion into a vagina, and an expanded configuration wherein each of the two elements are separated by a distance, and contact at least a portion of the vagina to support at least a portion of a prolapsed organ.

Additionally, the dual arm pessary includes a support element configured to maintain the distance between the two elements in the expanded configuration. Pulling the support element causes the arms to return to the compact configuration.

In some embodiments, the pessary is in the form of a coil (e.g., coaxial with the vagina), or includes ribs which lie along such a coil, and optionally supported from within.

In some embodiments of the invention, the pessary embodiments presented above include an applicator configured to press the ring into an expanded shape and release the deployed pessary within the vagina. With the ring locked in the expanded configuration with one of the locking embodiments explained above, the applicator is released from the pessary, allowing removal from the pessary embodiment so that the applicator may be pulled out of the vagina.

In some embodiments of the invention, the pessary applicator may be operated without the user touching the vagina or the surrounding skin.

According to additional embodiments of the invention, there is provided an inflatable pessary for supporting a prolapsed organ. The inflatable pessary includes an inflatable chamber having at least two inflatable arms, the inflatable chamber having at least two configurations: an uninflated configuration having a size suitable for insertion into a vagina; and an inflated configuration in which at least a portion of the inflatable chamber contacts a portion of the vagina, and supports at least a portion of a prolapsed organ.

Additionally, the inflatable pessary includes an inflatable chamber having a one-way valve that connects to an inflator, the one-way valve remaining with the inflated inflatable chamber in the vagina. The one-way valve, connected to a string, maintains the inflatable chamber in the inflated configuration. Pulling the string opens the valve, causes release of inflation fluid contained within the inflatable chamber, whereby the inflation chamber becomes uninflated.

In some embodiments of the invention, the inflatable chamber comprises two arms extending from the inflator that assume a "U" shape in the inflated configuration. In other embodiments, the inflatable chamber comprises two arms that extend in a circular configuration from the inflator, forming a substantially complete circle in the inflated configuration.

In some embodiments of the present invention, the pessary embodiments presented are disposable, while in other embodiments, the pessary embodiments are suitable for reuse. The pessary embodiments are optionally inserted for a relatively short period of time, for example during the day, which may reduce chances of infection and pressure ulcers associated with existing art devices.

According to some embodiments of the invention, there is provided a method for supporting a pelvic organ, the method including placing a device having a planar compact shape in a vagina, expanding the ring to support at least one prolapsed organ, and supporting the expanded device with a support structure.

Before explaining at least one embodiment of the invention in detail, it is to be understood that the invention is not necessarily limited in its application to the details of construction, nor to the arrangement of the components and/or methods set forth in the following description and/or illustrated in the drawings and/or the Examples. The invention is capable of other embodiments or of being practiced or carried out in various ways. In particular, it should be noted that the various locking, unlocking, applicator, state changing, removing and/or hinge mechanisms may be combined between pessaries and/or used for different pessary designs and/or materials.

Pessary Ring

Referring now to the drawings:

FIG. 1A shows a portion of an embodiment of the present invention of a pessary 300 comprising a ring 302 having a rhomboid compact configuration for insertion into the vagina. As shown in FIG. 1B, ring 302 expands to press the vaginal walls and thereby substantially alleviates pelvic organ prolapse.

Figure 2B:
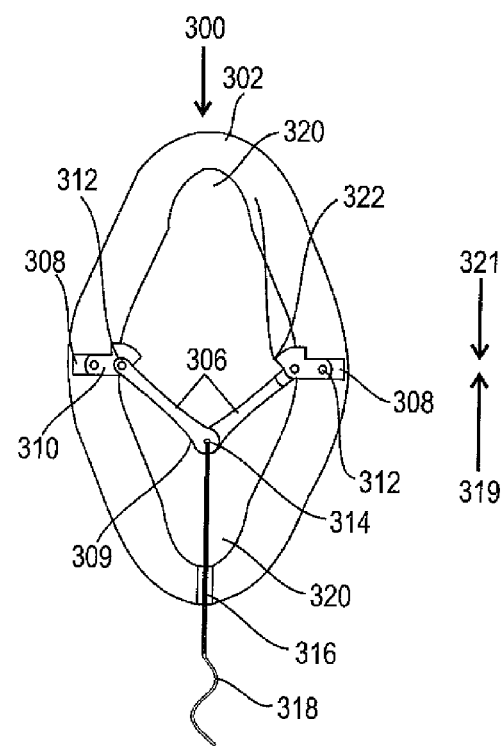
Figure 2C:
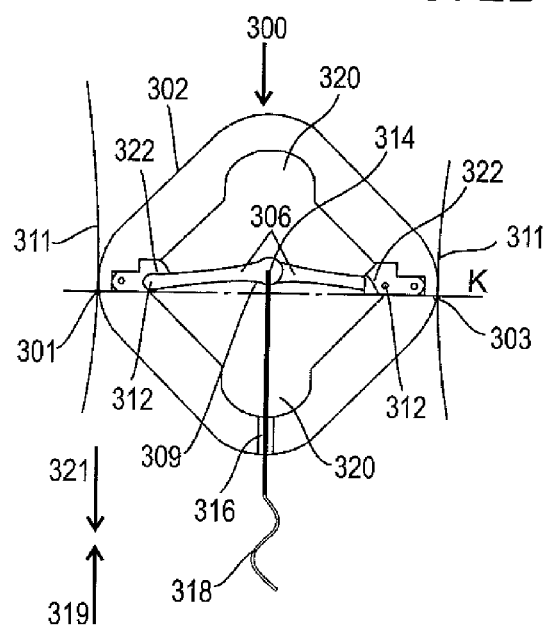
Figure 2D:
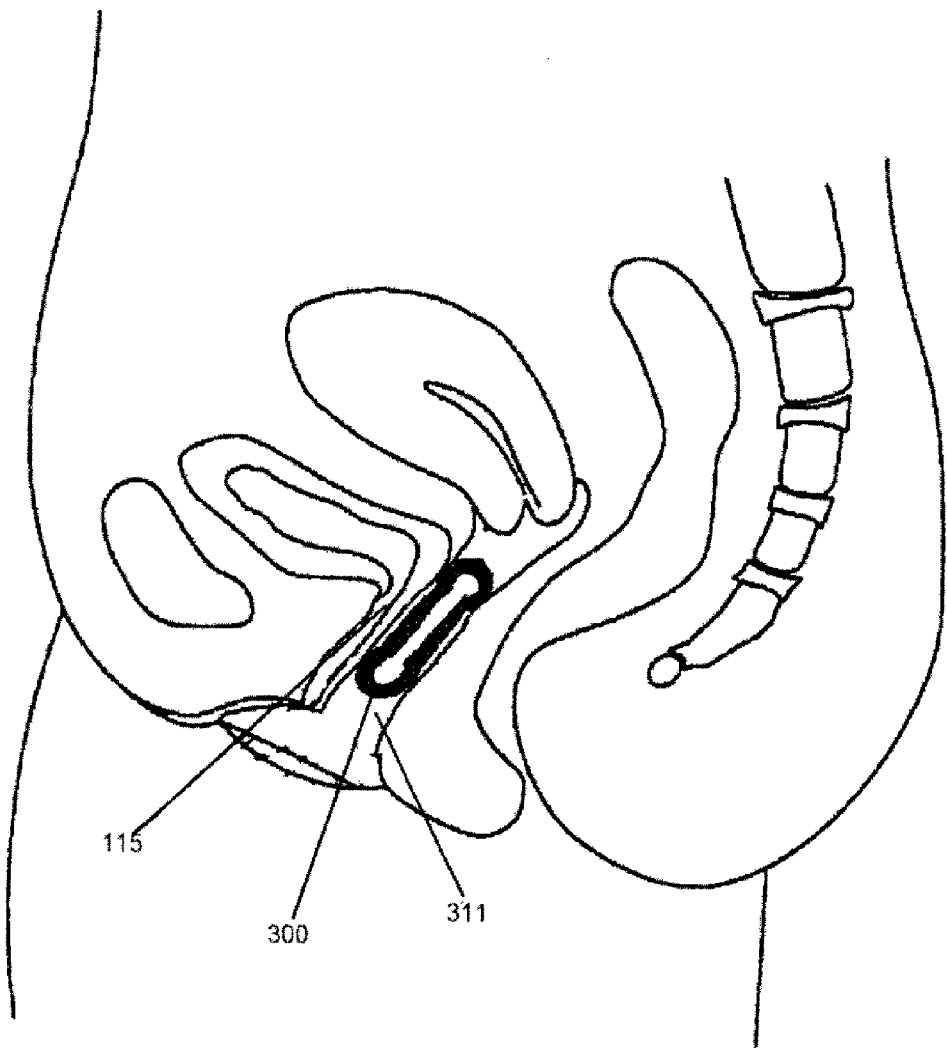
Figure 2E:
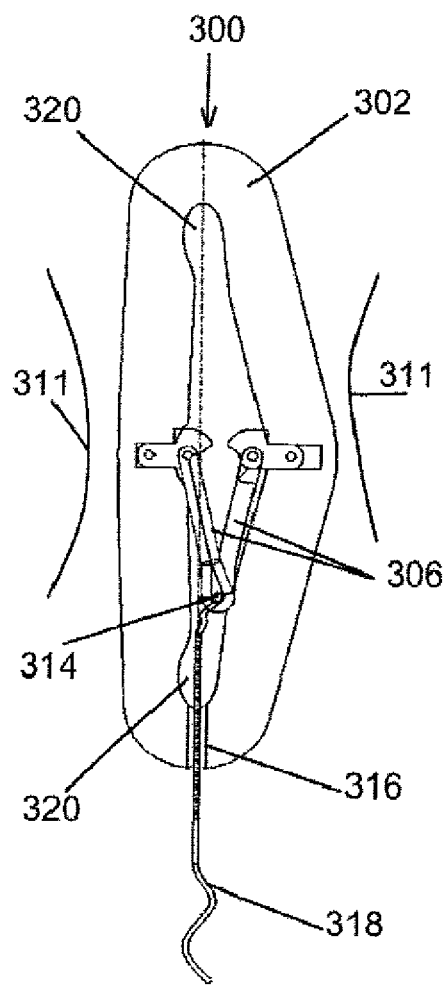

In some embodiments of the invention, in the compact configuration, pessary 300 may have an oval shape (FIG. 1C) or even a triangular shape (FIG. 2E). The various shapes for pessary 300 in the compact configuration are determined by, for example, ease of insertion and/or the desired shape of pessary 300 in the expanded configuration.

In some embodiments of the invention, pessary 300 includes a support mechanism that spans and supports ring 302 in the expanded configuration; some sample embodiments of the many possible configurations for the support mechanism being shown in FIGS. 2A-D.

Exemplary Support Mechanism

In some embodiments of the invention, a support mechanism 309, alternatively referred to as locking mechanism 309, comprises two arms 306 that are rotatably connected at hinge 314, alternately referred to as rotation axis 314. Optionally a string 318 is attached to the rotatable connection that serves to unlock arms 306, as will be explained below. Arms 306 are attached to limiters 310 along ring 302 with peripheral hinges 312.

Initially, ring 302, in the compact configuration, is inserted into a vagina 311 with arms 306 folded. During deployment, hinge 314 is pressed in a direction 319 to cause ring 302 to expand while arms 306 unfold (FIG. 2B). Ring 302 achieves a maximally expanded configuration (FIG. 2C) in which support curves 301 and 303 press laterally against the tissue of opposite and lateral aspects of vagina 311.

In the expanded configuration, limiter edges 322 press against arms 306, and lock arms 306 to maintain support mechanism 302 as a span across ring 302 while forming an angle having an apex above a transverse line k-k.

Exemplary Prolapse Alleviation

Without necessarily precluding other methods of use, the following exemplary method is provided, which may affect size, resilience and/or exact shape of the device. While laterally pressing the tissue of vagina 311, noted above, support curves 301 and 303 cause the tissue of vagina 311 to stiffen. The lateral pressure from support curves 301 and 303 causes flattening and stretching of anterior and posterior walls of vagina 311, so that a prolapsed apex of vagina 311 is stretched upward.

Additionally or alternatively, flattening and stretching of anterior and posterior walls of vagina 311 reduces prolapse associated with one or more external organs comprising the bladder, rectum, small intestine, and/or uterus.

Alternatively or additionally, the pessary optionally includes a membrane or cross-element which directly supports organs.

Alternatively or additionally, the pessary is optionally volumetric and fills a space in the vagina. Optionally, such space filling still includes passages for vaginal secretions therepast (including possibly therethrough).

Pessary 300, in some embodiments thereof, not only can be used to treat prolapse of vagina 311, but also to assess the need for surgical treatment in treating the prolapse. A positive result with pessary 300 in place may allow the user to forgo surgery that often presents a risk of untoward sequella.

Devices having walls that press against large areas of the entire tissue of vagina 311, taught by some of the above-noted patent art, may prevent fluid movement within vagina 311, resulting in fluid buildup and associated foul odors or infections.

In distinct contrast, the inventors have discovered that configuring support curves 301 and 303 to enclose a large aperture can allow fluid to exit vagina 311, thereby possibly substantially preventing associated foul odors or infections.

Exemplary Pessary Removal

Pulling application string 318 in a direction 321 causes hinge 314 to move in direction 321 so that arms 306 unlock by disengaging from limiter edges 322. Unlocked arms initially form an angle having an apex below line k-k as seen in FIG. 2B. Due to the friction between ring 302 and the walls of vagina 311, pulling string 318 to unlock arms 306 will not substantially move ring 302 with respect to the walls of vagina 311.

Once arms 306 are unlocked, the resilient flexible material of ring 302 returns to its original, natural and compact configuration shown in FIG. 2A, folding arms 306 so that compacted pessary 300 can be removed from vagina 311 by pulling string 318 further in direction 321.

Hinges 312 optionally connect arms 306 to limiters 310 in a manner that allow arms 306 to move only in directions 319 and 321, while being substantially limited in moving along a cross sectional plane through the upper surfaces of support curves 301 and 303; a substantially planar movement.

Limiters 310 are optionally attached to ring 302 in optional recesses 308 so that surface of limiters 310 is flush with the surface of ring 302.

In some embodiments of the invention, pessary 300 includes flexible materials that partially cover arms 306 and/or limiters 310 which may be replaced in between uses of pessary 300, thereby increasing ease of maintaining hygiene of pessary 300.

In other embodiments, pessary 300 is supplied with a replaceable tubular cover that installs around ring 302 and/or limiters 310 which may be replaced in between uses of pessary 300.

Exemplary Materials and Dimensions

The materials used in ring 302 may optionally comprise soft and/or flexible materials that increase user comfort; for example a rubber material, a polyurethane, a thermoplastic elastomer, a cardboard material, or a polymer. Pessary 300 may include an optional soft coating to enhance user comfort, for example a low shore silicone.

In some optional embodiments of the invention, ring 302 includes indents 320 that act as a resilient living hinge. Indents by a manufacturer of pessary 300 can be varied in depth, for example to facilitate easier opening of ring 302.

Optionally, ring 302 includes an internal flexible support frame 304 (FIG. 1A) comprising, for example: a metal, a nylon material, polypropylene and/or polyethylene. The inclusion of internal support frame 304 may allow ring 302 to be manufactured with softer cover materials that are less resilient.

With less resilient cover materials, support frame 304 is optionally configured to provide stiffness needed to maintain ring 302 in the compact configuration.

In some embodiments of the invention, compact ring 302 has a substantially planar configuration with a lateral dimension of between about 20 and 40 millimeters to facilitate easy and painless vaginal insertion.

Expanded ring 302 optionally attains a round shape (FIG. 1B) or alternatively, an oval shape or a rhomboid shape (FIG. 2C).

In some embodiments of the invention, expanded ring 302 may have an average diameter of between about 50 to 120 millimeters depending, for example on the desired final shape and size of the cavity of vagina 311.

The many possible shapes and sizes of ring 302 in the compact and expanded configurations are well known to those familiar with the art.

In general, pessary 300 differs substantially from other devices that insert into vagina 311. For example, as shown in FIG. 2D, expanded pessary 300 typically places the greatest pressure above the position of a bladder neck 115. Additionally, this pressure is directed against the lateral walls of vagina 311.

In distinct contrast, a urinary continence device is configured to place the greatest pressure on bladder neck 115, which is located along an anterior position of vagina 311.

In some alternative embodiments, ring 302 naturally maintains the laterally outward configuration. By pulling application string 318 in direction 321 (FIG. 2C), arms 306 pull ring 302 into the compact configuration. Maintaining tension on string 318 keeps ring 302 in the compact configuration, (FIG. 2A), allowing insertion and removal from vagina 311.

Releasing string 318 allows ring 302 to expand laterally outward while arms 306 extend (FIG. 2C). In such embodiments, hinge 314 may include an optional spring mechanism to aid in maintaining arms 306 folded and ring 302 compact.

In some embodiments of the invention, ring 302 may have alternative configurations, just one of the many alternative configurations now being presented.

Alternative Pessary Ring Configurations

Figures 3A, 3B, 3C:
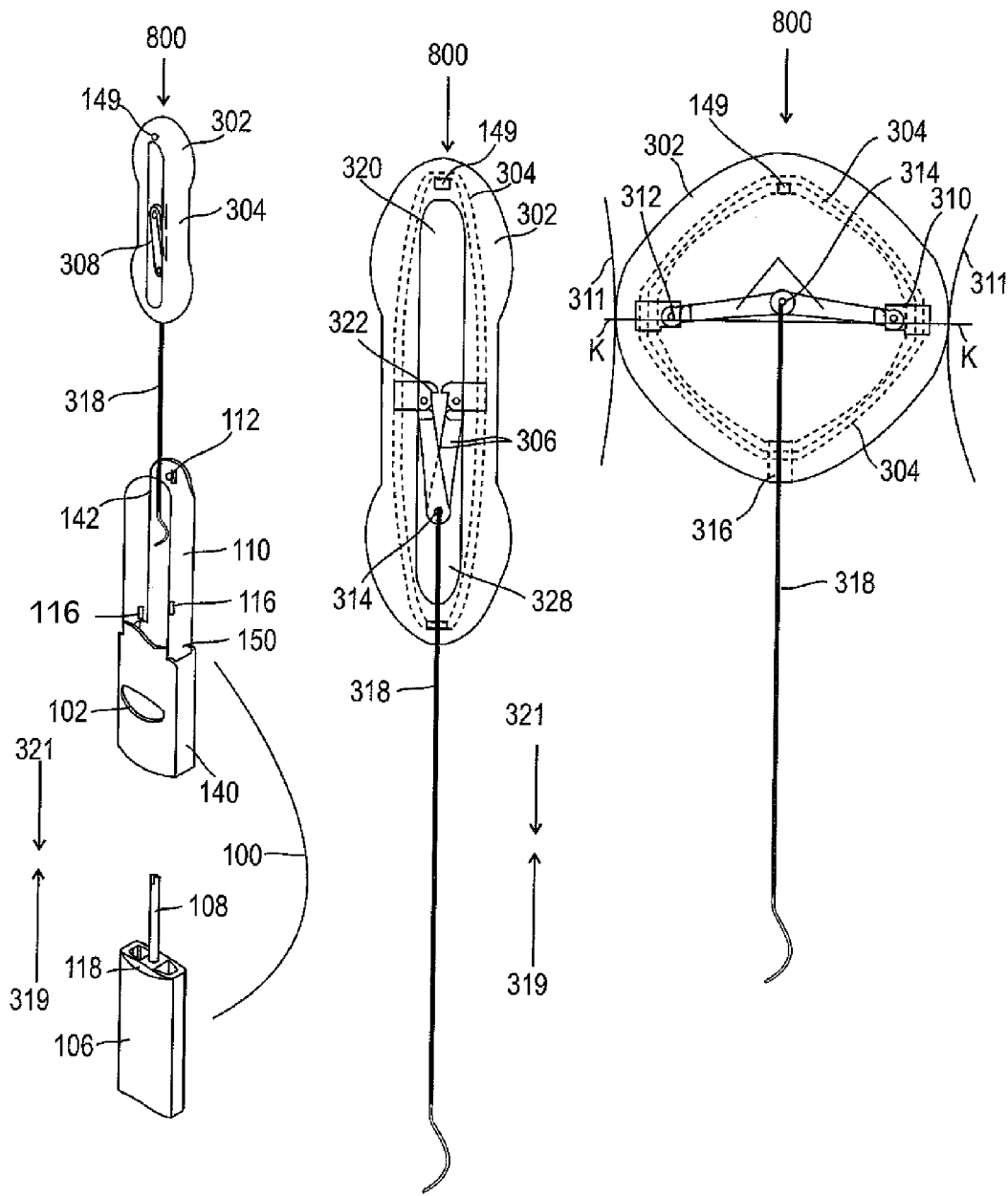

FIG. 3A shows an exploded view of a pessary assembly 800 in which ring 302 includes support frame 304 as described above, allowing for the use of softer cover materials around support frame 304, noted above.

Limiters 310 are attached directly to support frame 304 and emerge from slots through ring 302. In this configuration, arms 306 exert direct pressure on support frame 304 which governs the expansion of ring 302.

In some embodiments of the invention, pessary 300 is included with an applicator that is operated by a user to expand ring 302 within vagina 311. Just some examples of the many possible applicator embodiments are presented.

Exemplary Pessary Applicators

In some embodiments of the invention, an applicator 100 includes a housing 140 which has an ovoid cross sectional profile along the transverse plane; a profile configured to match the user anatomy, as vagina 311 is parted during insertion of pessary assembly 800.

As shown in FIG. 3A, housing 140 includes applicator arms 110 which include a first snap 142 and a second snap 112, respectively, which removably snap into receptacles 149 on either side of the upper portion of ring 302.

Figure 3D:
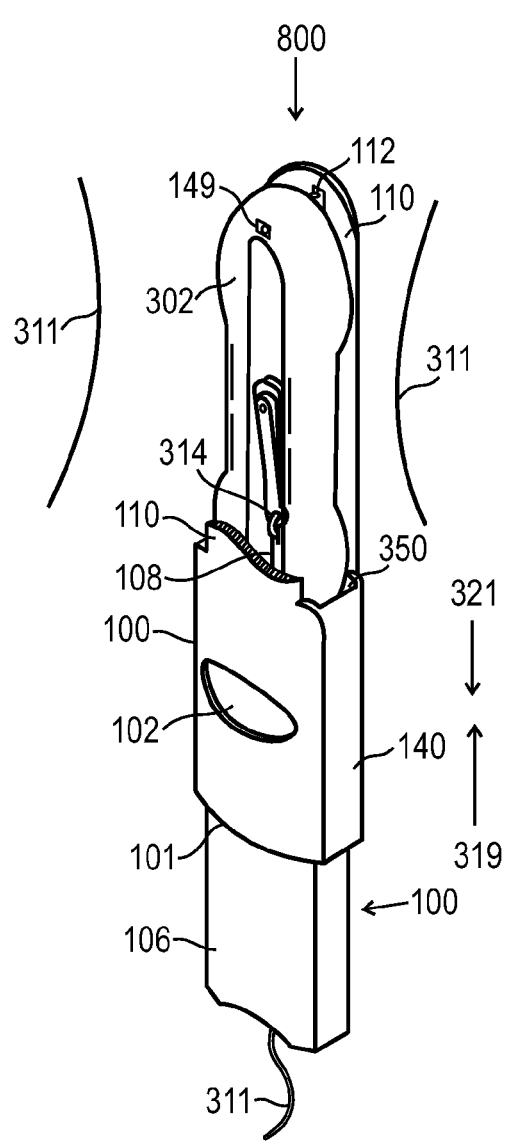

In the compact configuration, ring 302 is attached to applicator 100, as shown in FIGS. 3A and 3D. The bottom portion of ring 302 is set in housing 140, first snap 142 and second snap 112 snap into receptacles 149.

Figure 3E:
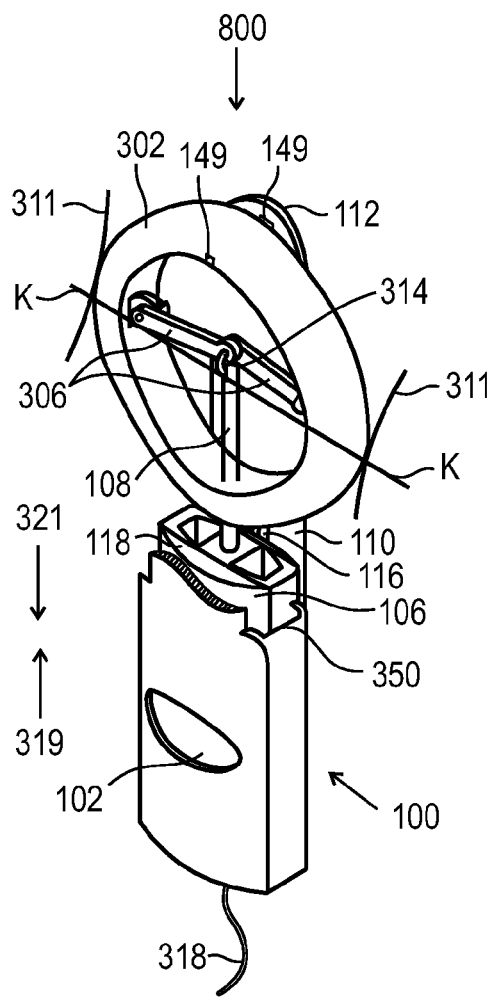
Figures 6A, 6B:
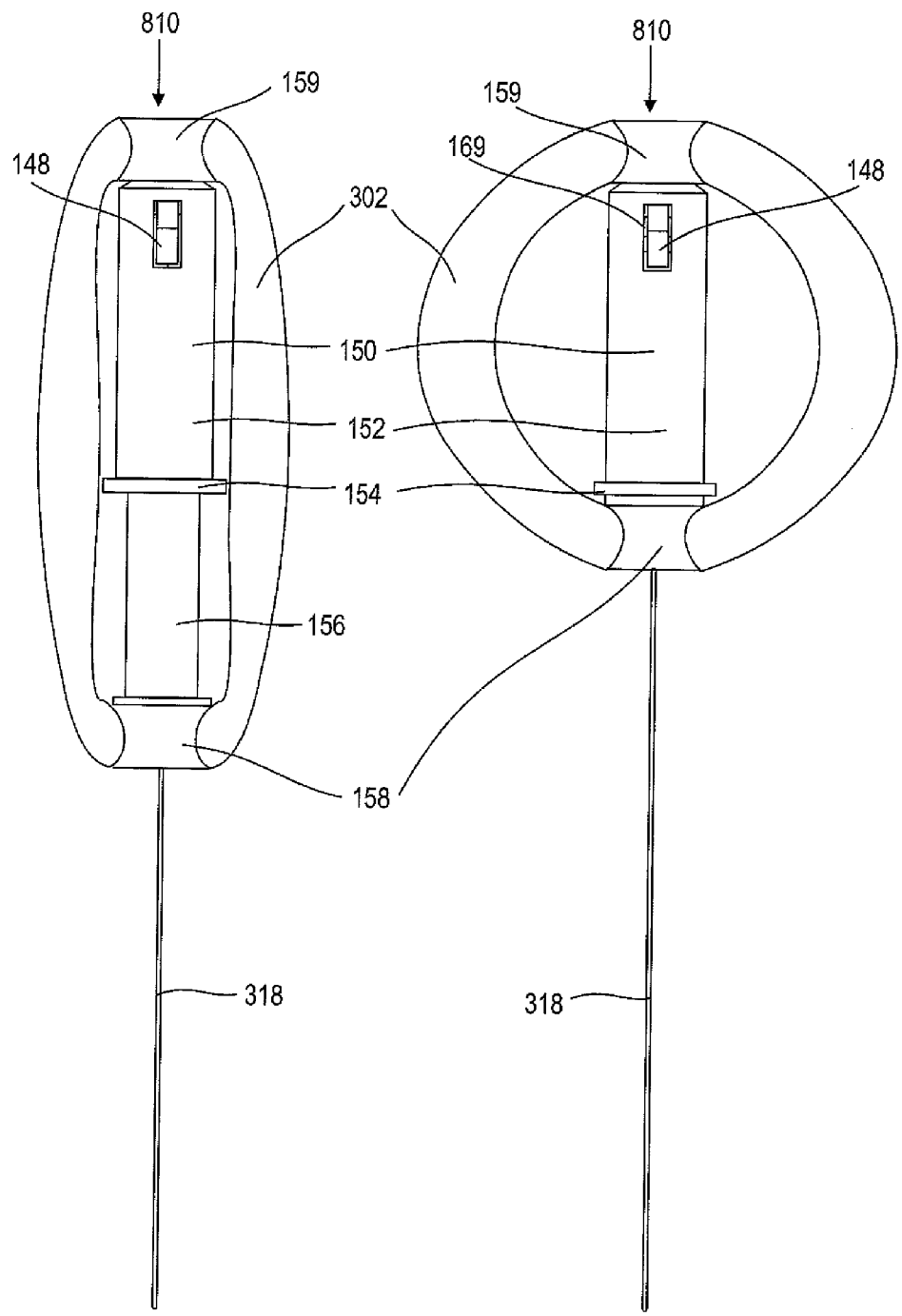
Figures 7A, 7B:
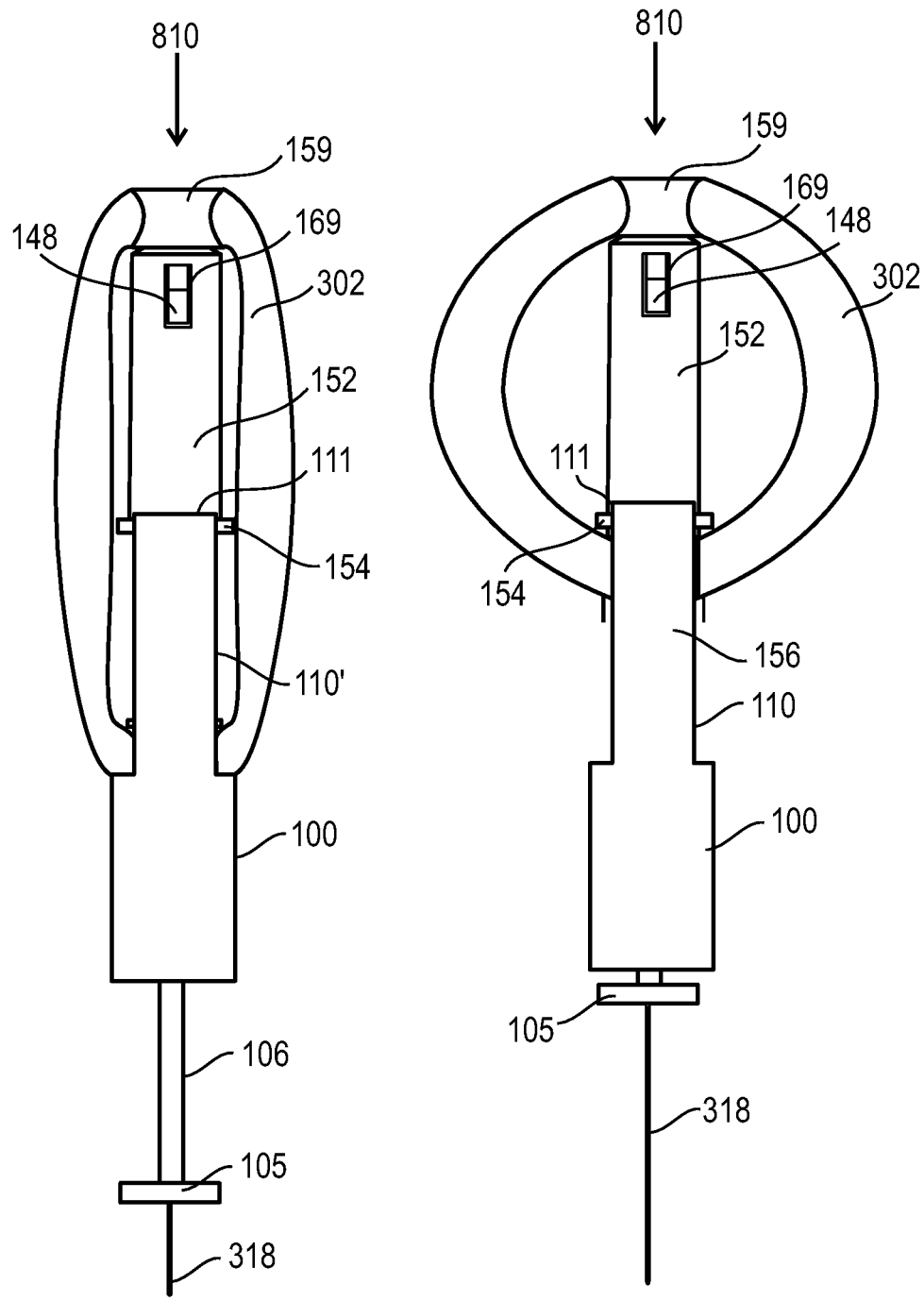

To expand ring 302, the first and third fingers are placed in convex recesses 102, on the front and back of housing 140, while the user's second finger pushes plunger 106 through housing 140 in direction 319. Movement of plunger 106 causes a hollow rod 108 to press arms 306 in direction 319, thereby extending arms 306 as shown in FIGS. 3D-3E.

Arms 306 extend until ring 302 attains the expanded shape shown in FIG. 3C and arms 306 form an angle having an apex above line K-K, as noted above. Following expansion of ring 302, applicator arms 110 are pushed outwardly, as a result of movement of an upper slope 118 of plunger 106 over inner projections 116 (FIGS. 4A-4C) on either side of applicator arms 110. As upper slope 118 passes inner projections 116, the walls of housing 140 bulge outward, and applicator arms 110 move apart, releasing ring 302.

Applicator 100 (FIG. 3A) is removed from ring 302 and out of vagina 311 leaving expanded ring in vagina 311 as shown in FIG. 3C.

Removal of ring 302 from the vagina occurs when string 318 is pulled in direction 319 so that arms 306 resume the position seen in FIG. 3B with ring 302 in the compact configuration.

In some embodiments of the invention the support mechanism may comprise sliding tubular components, the following description relating to just one of the many embodiments of sliding support mechanisms.

Sliding Pessary

FIGS. 5A-5D show embodiments of a sliding pessary 810 having a smaller diameter tube 156 that slides into a larger diameter tube 152.

Larger diameter tube 152 is attached at an upper connector portion 159 on ring 302, and smaller diameter tube 156 is connected to a lower connector portion 158 on ring 302.

As smaller diameter tube 156 slides into larger tube 152 in direction 321, ring 302 is caused to expand (FIG. 5B).

FIGS. 5C-5D show sliding pessary 810 assembled on applicator 100 with string 318 emerging from hollow tube 106 which is connected to plunger handle 105.

With ring 302 in the elongated, compact configuration (FIG. 5C), sliding pessary 810 is placed in the vagina. Plunger handle 105 is pressed in direction 319 so that the flat base presses against lower connector portion 158, causing smaller diameter tube 156 to telescope into larger diameter tube 152, resulting in the above-noted expansion of ring 302.

FIGS. 7A-9B show sliding pessary 810 loaded on applicator 100. The upper portion of applicator arm 110 has a projection 111 that faces inward. During expansion of ring 302 (FIGS. 8B and 9B), projection 111 is secured against a circumferential edge 154, thereby holding larger tube 152 in position as plunger handle 105 is pressed against smaller tube 156 to cause expansion of ring 302.

As used herein, inward projection may be alternatively referred to herein as a "medially facing" projection, and a motion that moves inward with respect to ring 302 may be referred to as a "medial motion".

Figure 8A:
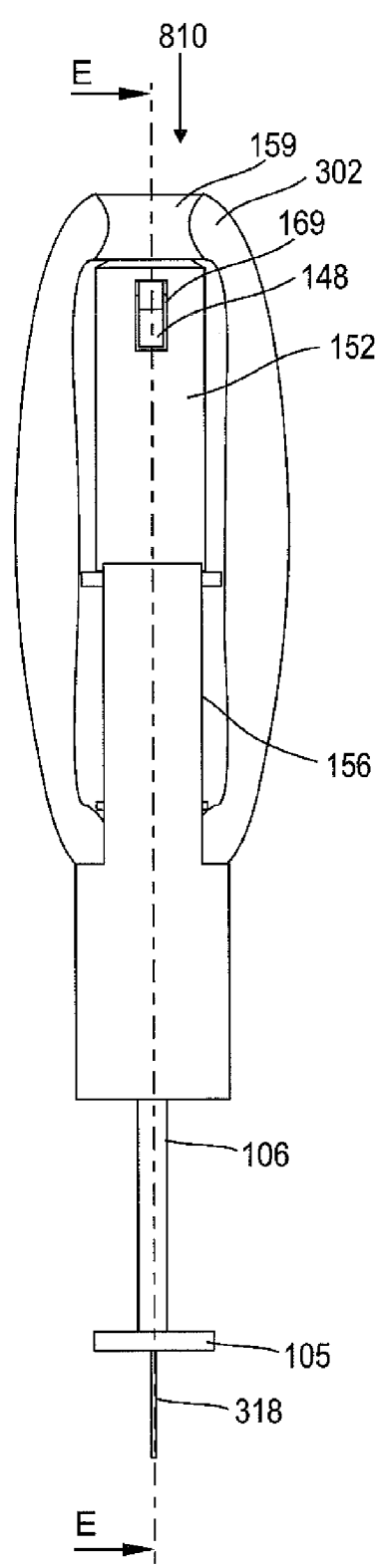
Figure 8B:
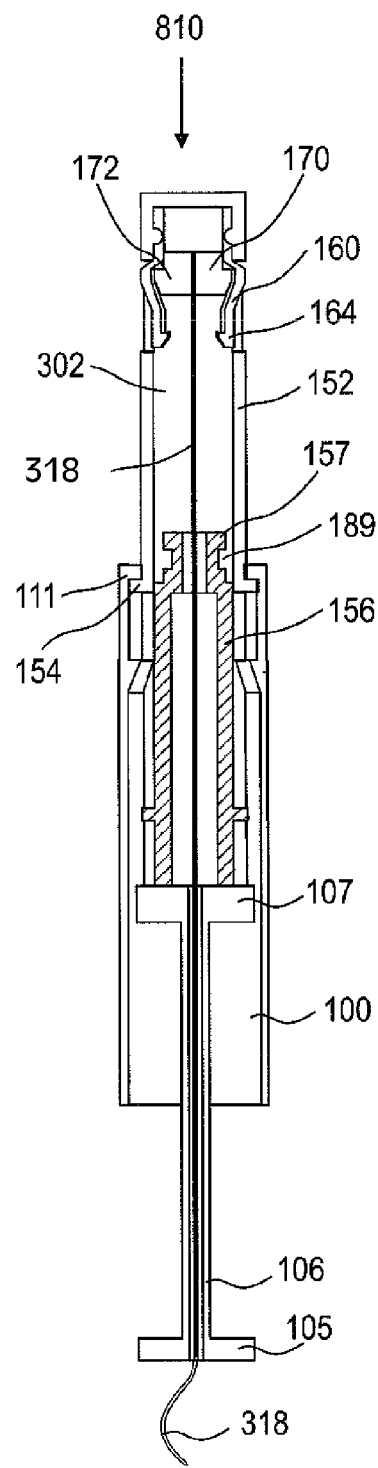

FIG. 8B shows a cut section of sliding pessary assembly 810 with ring 302 in applicator 100, prior to vaginal insertion.

Figure 9A:
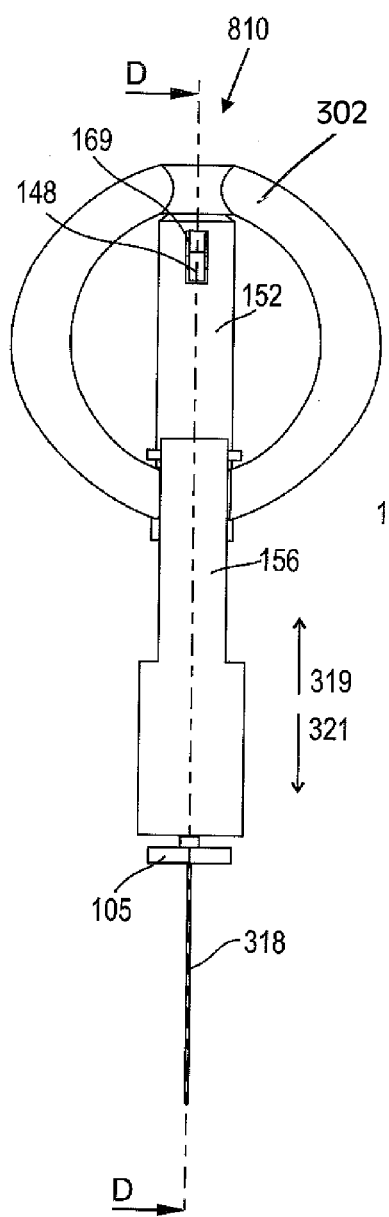
Figure 9B:
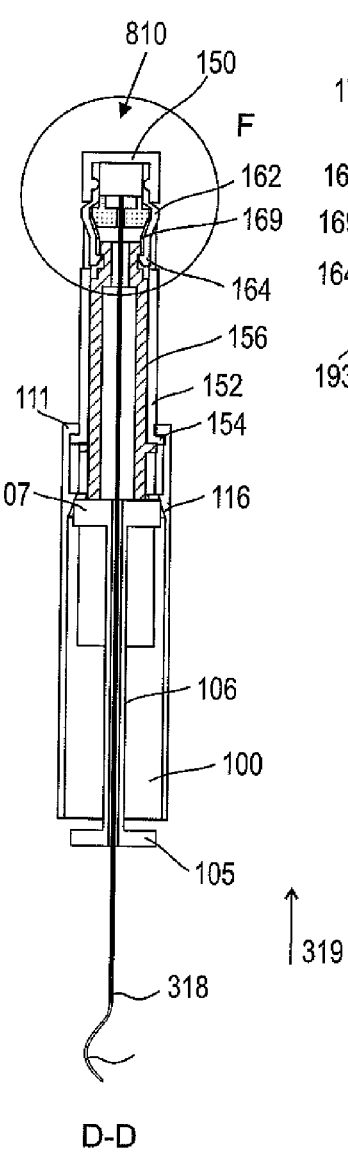
Figure 9C:
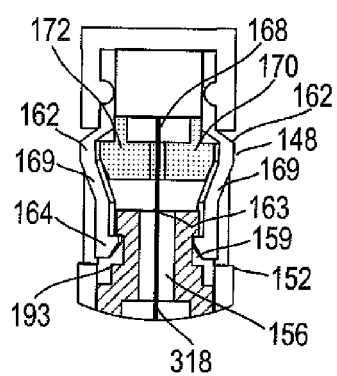

As shown in FIG. 9B, plunger handle 105 has been pressed in direction 319 to cause smaller tube 156 to move in direction 319 causing expansion of ring 302. As shown in detail in FIG. 9C, the upper portion of smaller diameter tube 156 has a round ring 163 and a recess 159.

Sliding pessary assembly 810 includes any one of a variety of locking mechanism embodiments that locks tubes 152 and 156 in the telescoped configuration; the following being just one example of the many possible locking mechanism embodiments.

Exemplary Locking Mechanism

As a flat section 107 pushes smaller tube 156 within larger tube 152, smaller tube 156 slides into a locking mechanism comprising tabs 169 having internally projecting prongs 164. A round ring 163 causes tabs 169 to splay outward until prongs 164 pass into recess 159.

Tabs 169 contract inward from apertures 148 as prongs 164 move inward into recess 159, and tubes 152 and 156 become locked in position with ring 302 in the expanded position (FIG. 9A).

In addition, as ring 302 reaches the maximal expansion, flat section 107 reaches sloped prongs 116 on the inner aspect of applicator arms 110. Movement of flat section 107 pushes both arms 110 outward so that protrusions 111 depart from rim 154; following which applicator 100 may be disengaged from sliding pessary 810.

Due to the dimensions of expanded ring 302, ring 302 remains within the vagina while applicator 100 is removed, and string 318 protrudes outside vagina 311 for removal of ring 302.

Optionally, apertures 148 and/or recess 159 may be of a sufficient size to allow some movement of prongs 164 so that larger tube 152 moves with respect to smaller tube 156. Movement of tubes 152 and 156 may allow, for example, oscillation within ring 302 that may contribute to user comfort for example when the walls of vagina 311 are less flexible, for example following prior surgical intervention.

Figures 10A, 10B, 10C:
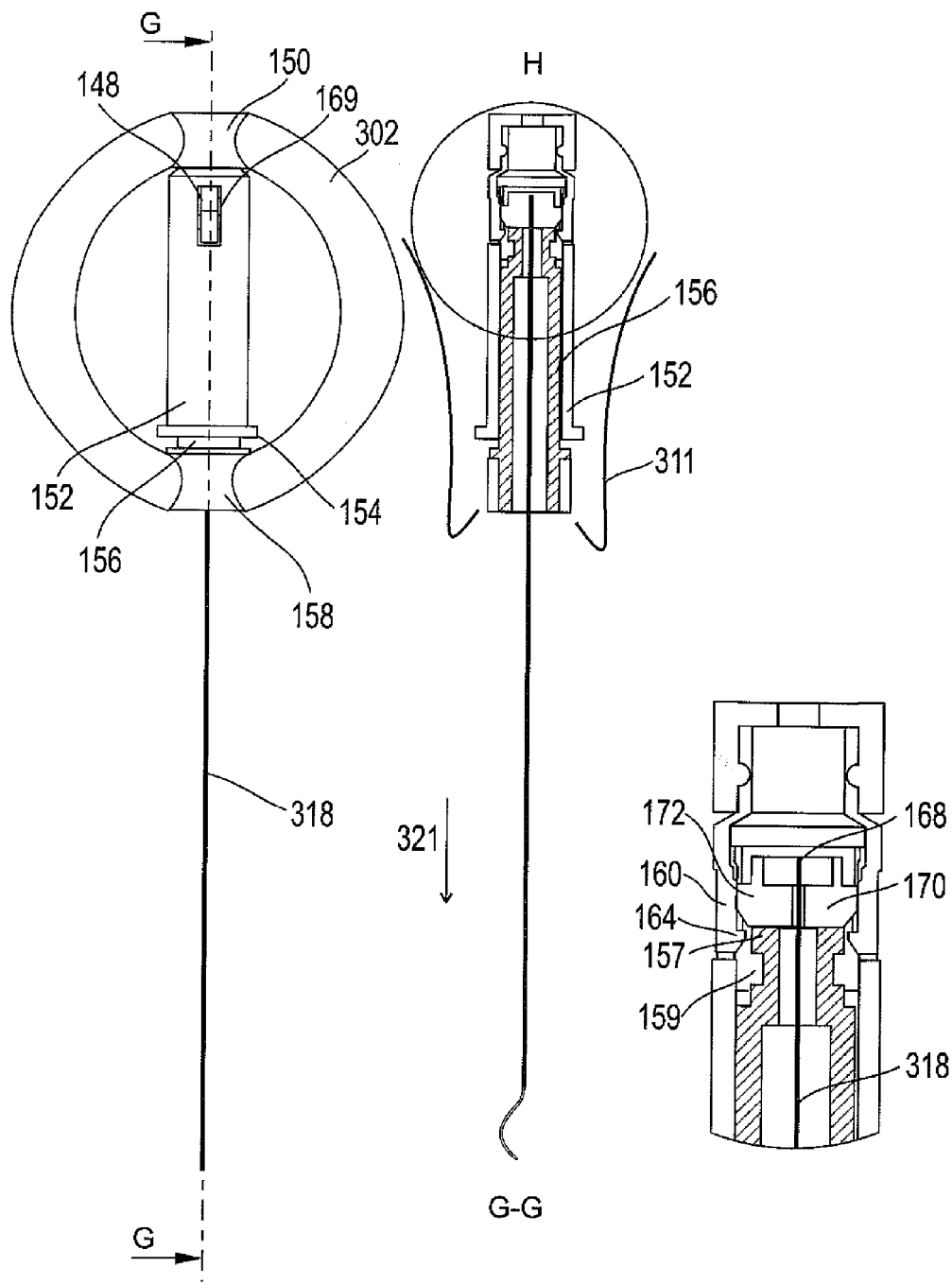

To remove sliding pessary 810 from the vagina, string 318 is pulled in direction 321 as shown in FIGS. 10A-C. An upper string portion 168 is attached to unlocking mechanism 170 which has a sloped edge 172.

When string 318 is pulled in direction 321, unlocking mechanism 170 moves in direction 321 with the wider portion of sloped edge 172 pushing aside tabs 160 and prongs 164, hence disengaging smaller tube 156 from larger tube 152.

Figures 11A, 11B, 11C:
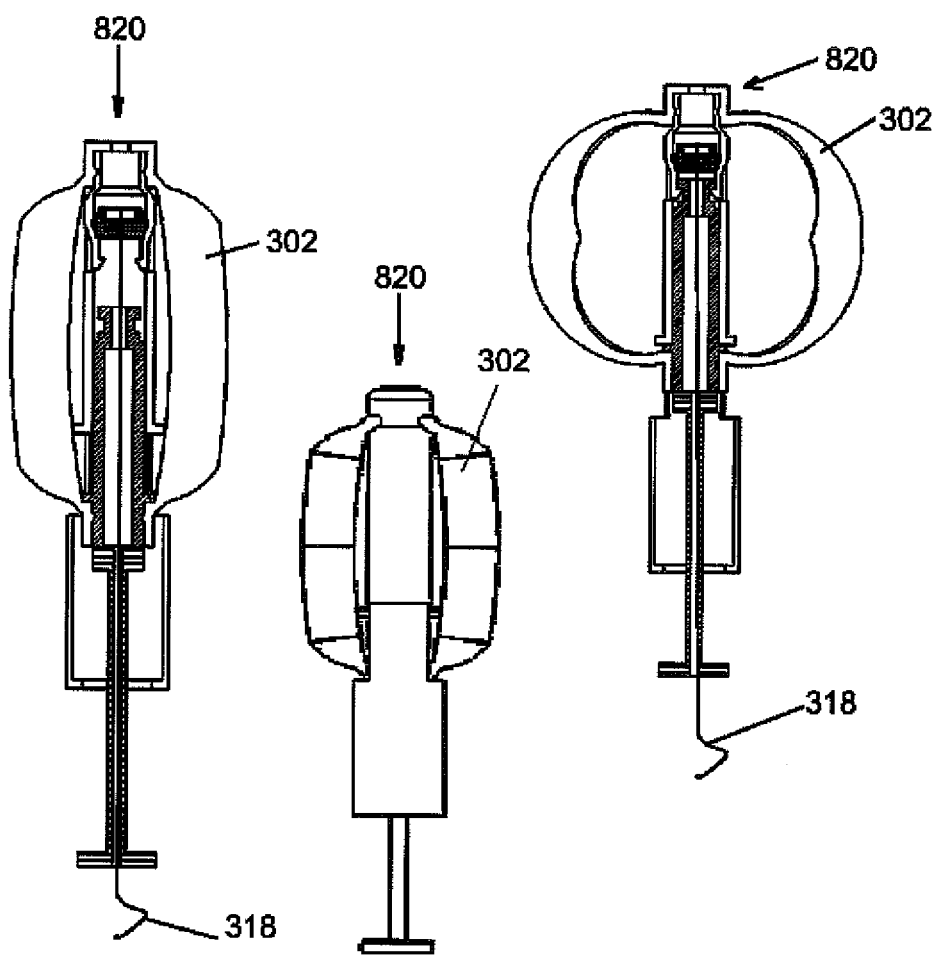
Figures 12A, 12B:
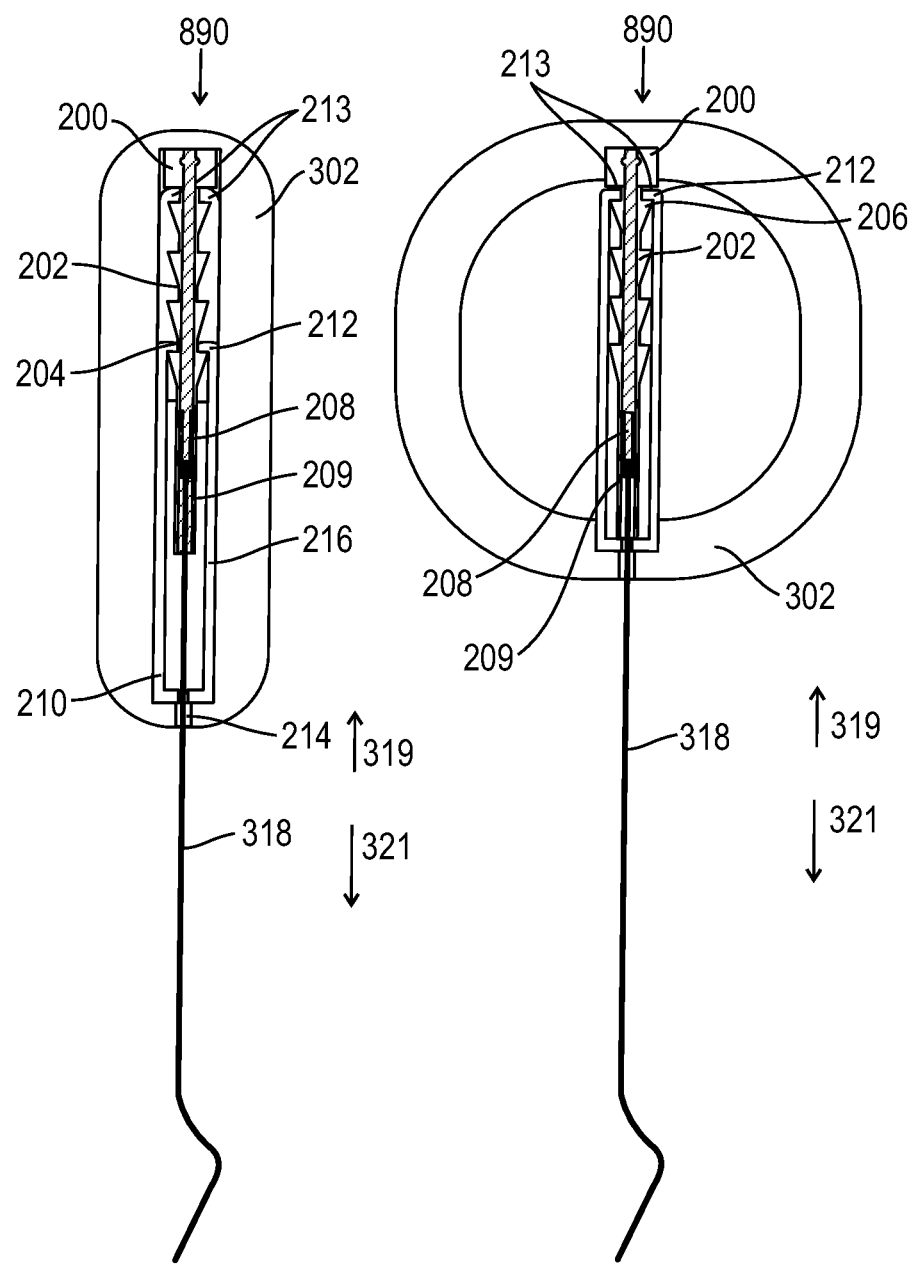
Figure 12C:
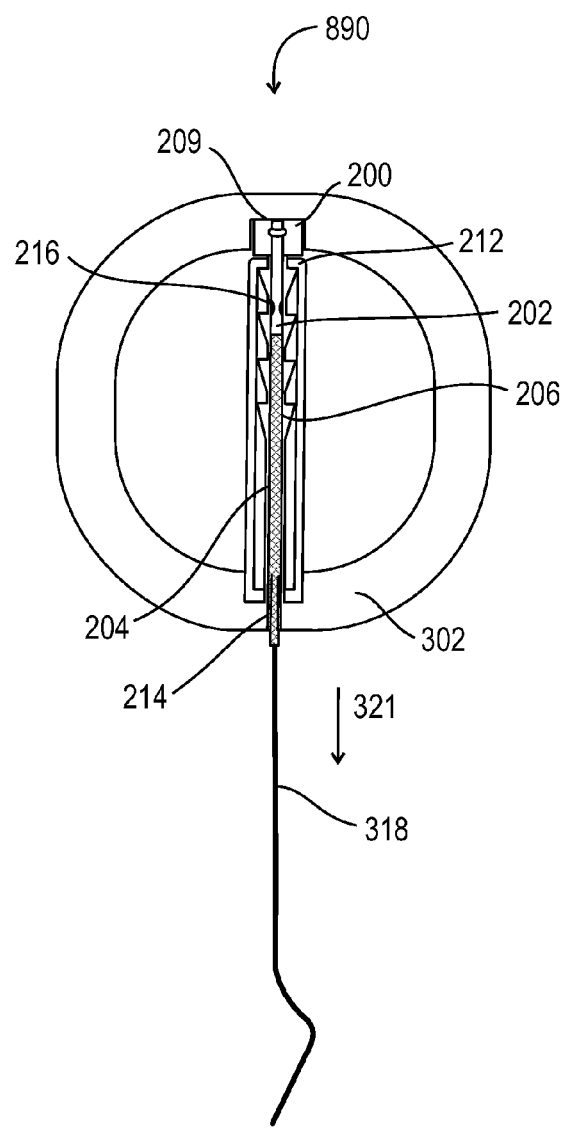
Figure 12D:
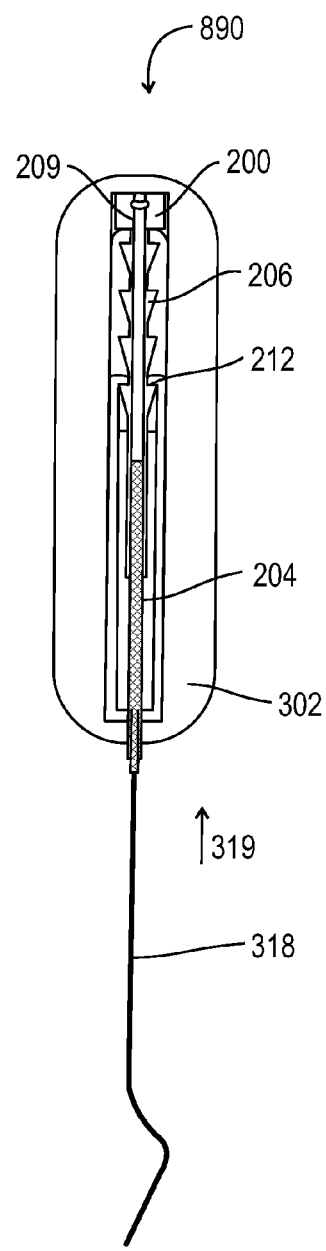
Figures 12E, 12F:
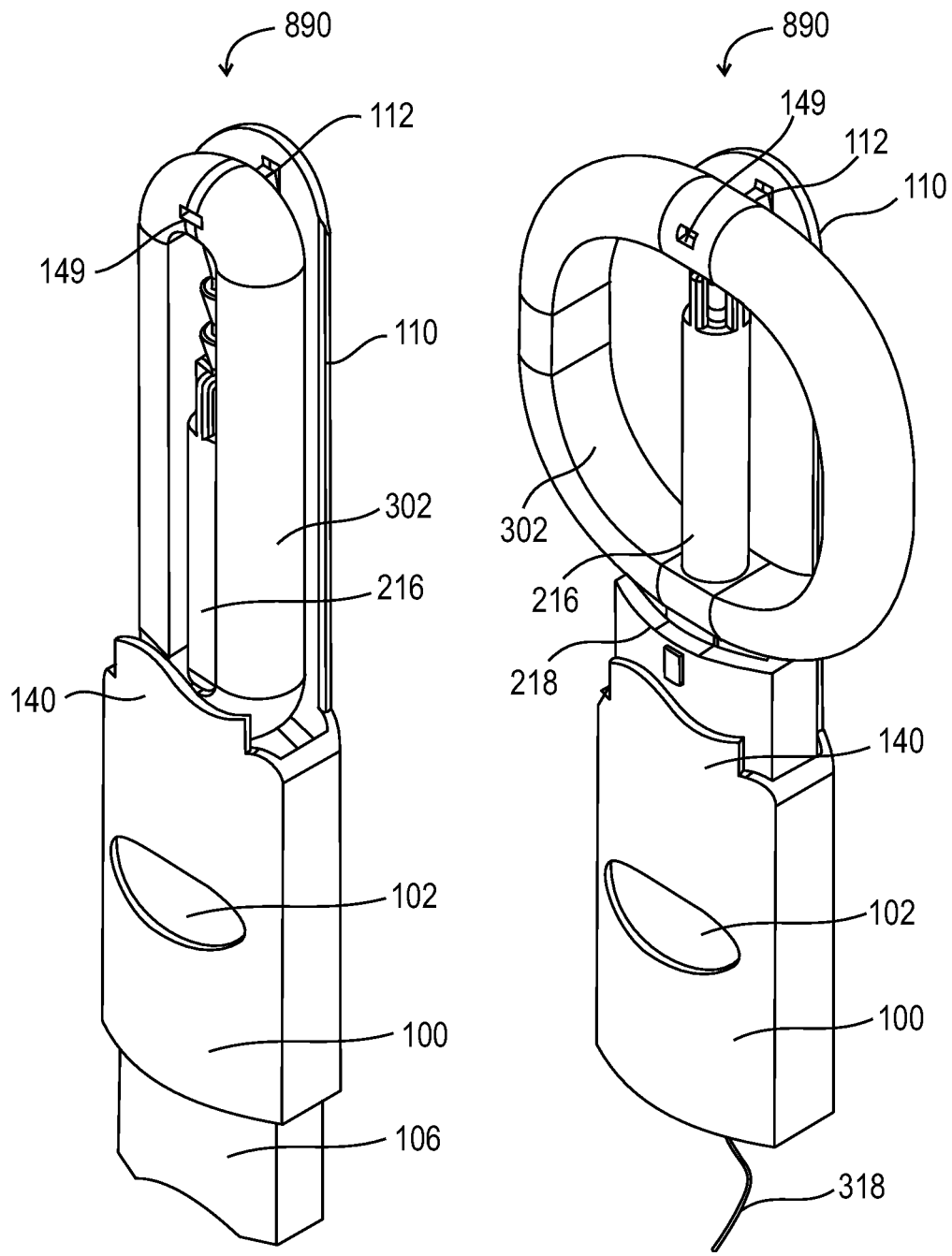
Figure 12G:
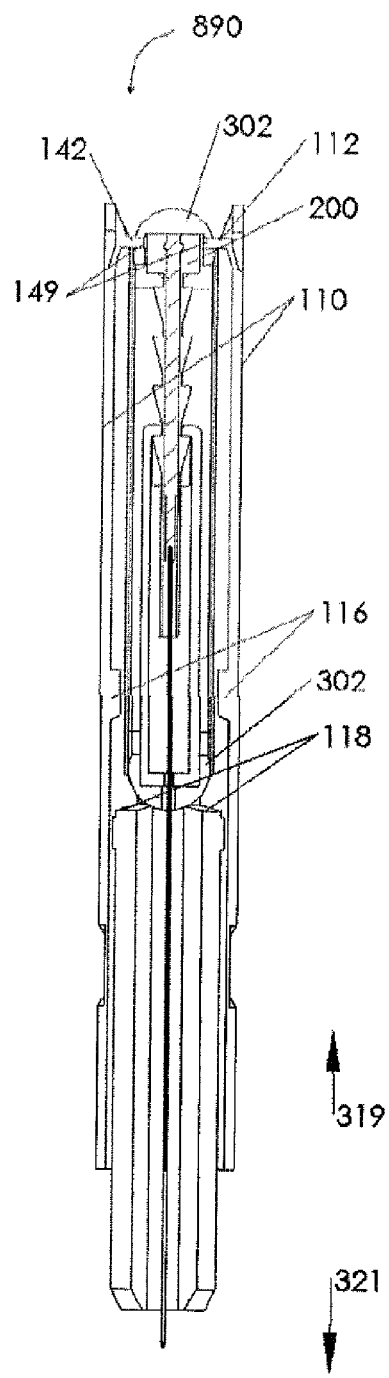
Figure 12H:
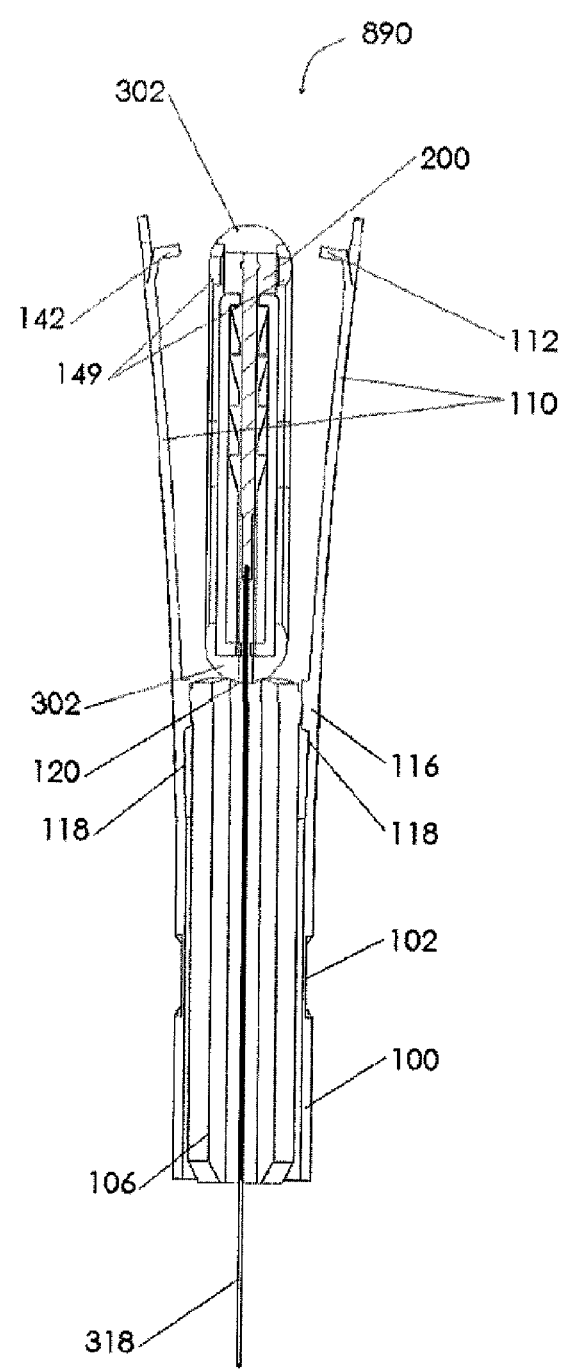

FIGS. 11A-11C show still another embodiment of a pessary assembly 820 in which expanded ring 302 forms an aperture having four curves forming a clover-leaf shaped aperture.

In some embodiments of the present invention, the support structure may include one or several ratchet mechanisms, the following description being directed toward just one such embodiment.

Ratchet Pessary

A ratchet pessary 890, shown in FIGS. 12A-12H, includes an anchor 200 within the upper portion of ring 302 and a flexible tube 202 extending downwardly therefrom. Flexible tube 202 has multiple ratchets 206 that project outward therefrom.

A ratchet lock mechanism 216 includes upper projections 212 that resiliently ratchet along ratchets 206 to expand ring 302. Upper projections 212 then enter upper openings 213 and maintain ring 302 in the expanded configuration.

Insertion of ratchet pessary 890 may take place using applicator 100 (FIGS. 12E-12H), which has a flat surface 120 (FIG. 12H) that presses the lower portion of ring 302 to cause outward expansion as the upper portion of ring 302 is held in place by projections 112.

Exemplary Removal of Ratchet Pessary

A cavity 209 (FIG. 12C-D) running through flexible tube 202 contains a spacer 204 which slides out of cavity 209. String 318 is connected to the distal end of spacer 204.

Pulling string 318 through tunnel 214 in direction 321 (FIG. 12C) pulls spacer 204 out of hollow tube 202. With spacer 204 removed, cavity 209 collapses and ratchets 206 implode and/or deform so that projections 212 will move freely in direction 321, unhindered by ratchets 206; thereby allowing ring 302 to return to a natural, unexpanded configuration.

In some embodiments of the invention, the pessary support element may comprise any one of several vacuum actuated support elements; the following being just one such pessary embodiment.

Vacuum Pessary

Shown in FIGS. 13A-13G is a vacuum pessary 895, in which smaller tube 356 is contained within larger tube 352 in an extended position (FIG. 13B), as noted above. To expand ring 302, smaller tube 356, configured as a piston, is moved in direction 319 into larger tube, forcing air out of a chamber 353 through a one way valve 350.

Figure 13A:
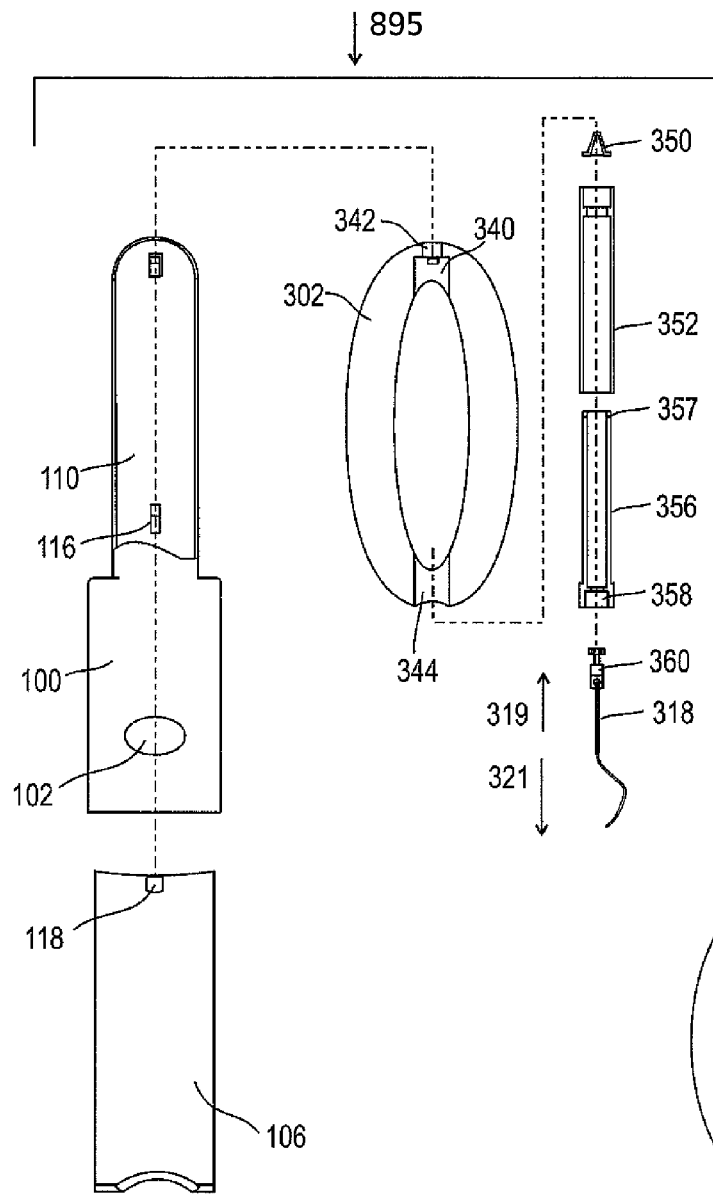
Figure 13B:
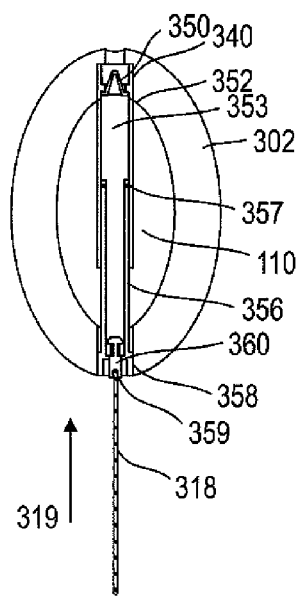
Figure 13C:
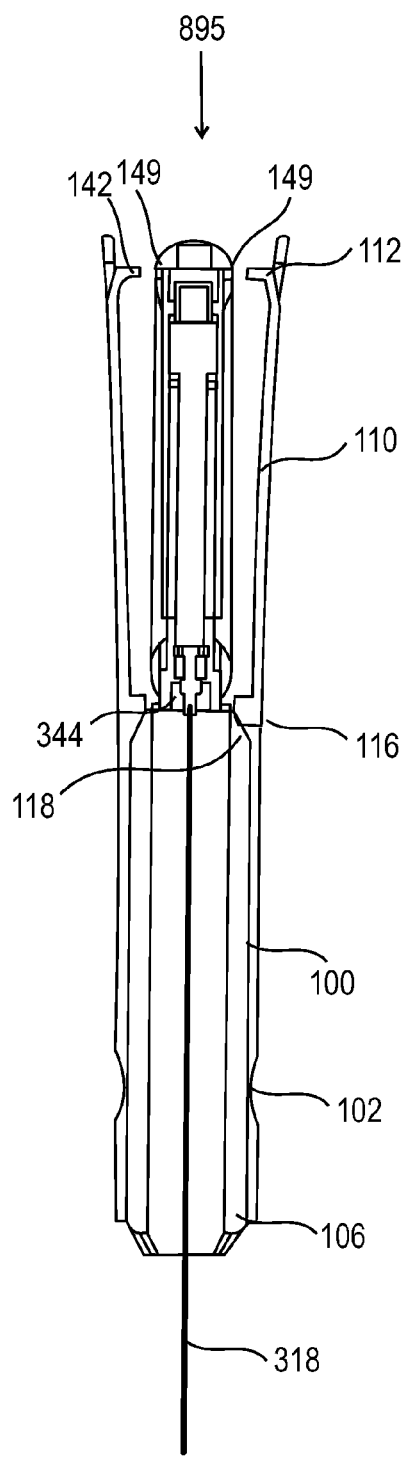
Figure 13D:
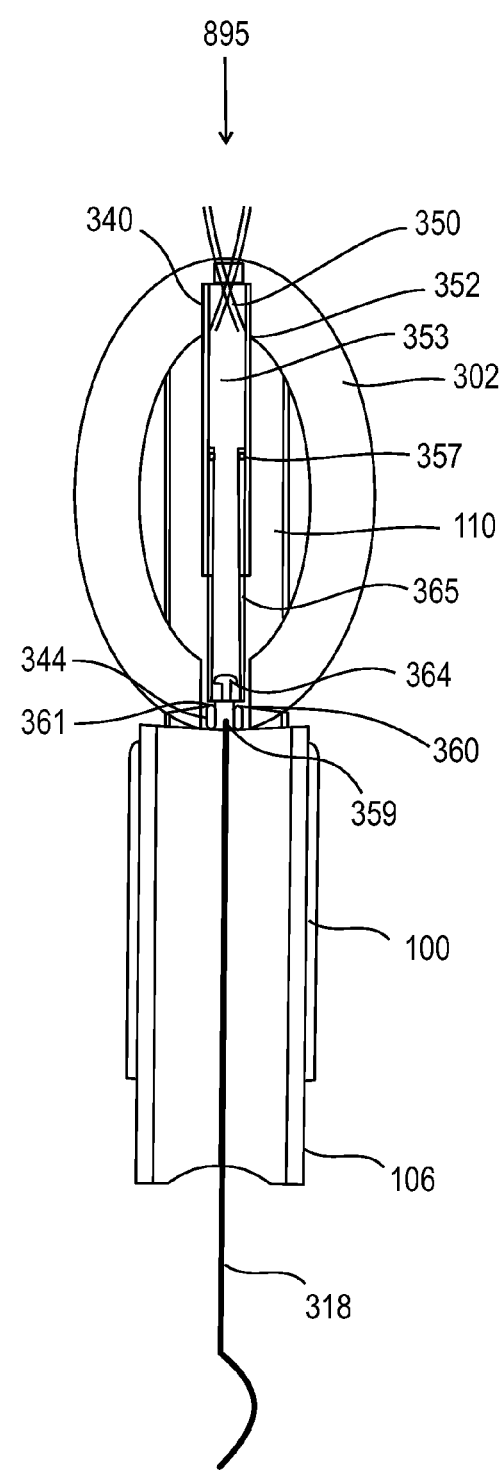

FIGS. 13C-13D show details of vacuum pessary 895 in which larger tube 352 is docked into a proximal docking slot 340 and smaller tube 356 is docked at docking slot 344.

An "O" ring 357 maintains a vacuum seal between tubes 352 and 356 so that vacuum pessary 895 maintains ring 302 in the expanded configuration until the user chooses to remove vacuum pessary 895.

Exemplary Removal of Vacuum Pessary

The lower end of smaller tube 356 has a vacuum release plug 360. To return ring 302 to the collapsed position, string 318, which is connected at point 359 to vacuum release plug 360, pulls plug 360 out of a plug receptacle 358 (FIG. 13A), thereby releasing the vacuum in vacuum chamber 353.

Figure 13E:
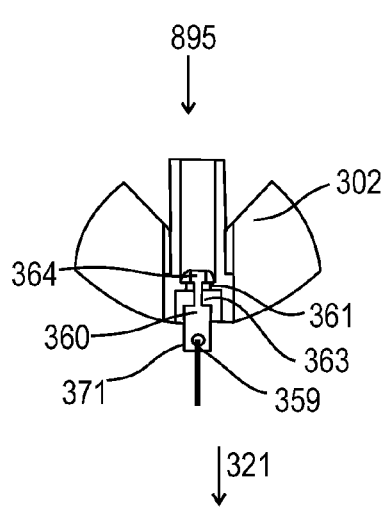
Figure 13G:
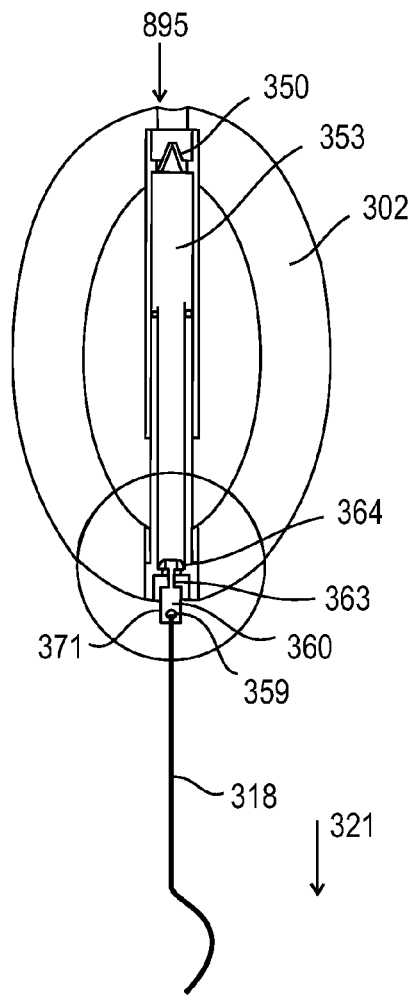
Figure 13F:
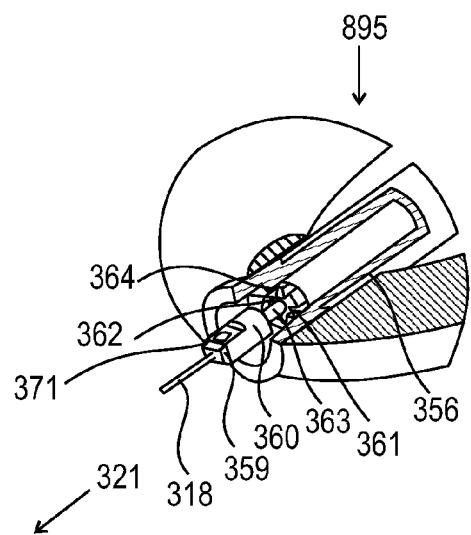

FIGS. 13E-F show details of vacuum release plug 360 including a narrow neck 363 connected to a disc 364 having air passages 362 therethrough. During vacuum maintenance, a plug body 371 is pressed into and forms a seal with a plug receptacle 361.

When plug 360 is pulled in direction 321, plug body 371 dislodges from plug receptacle 361 so that disk 364 is positioned at the end of plug receptacle 361, allowing air to flow into chamber 353 through air passages 362.

Disk 364 cannot be fully dislodged from plug receptacle 361, so further pulling of string 318 will pull vacuum pessary 895 out of the vagina.

In some embodiments of the invention, the supports that maintain ring 302 in the expanded position are integral to ring 302 and do not span across the center of ring 302. Just one of the many possible configurations of integrated supports is now presented.

Integrated Pessary

Shown in FIGS. 14A-14D is an integrated support pessary 910 in which first and second support locks 392 are located at support curves 301 and 303, respectively. As used herein the terms "integral" and "integrated" refer to support locks 392 that are located on or within ring 302 and/or do not span across the center of ring 302 in the expanded configuration.

Figure 14A:
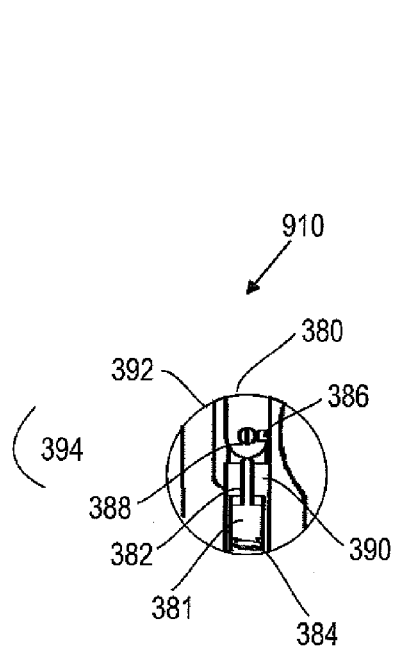
Figure 14B:
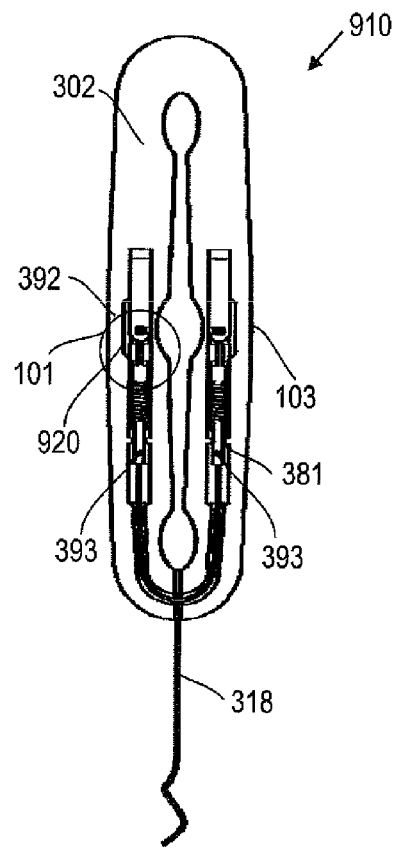
Figure 14C:
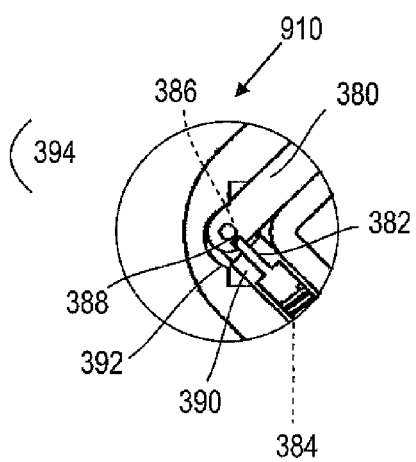

Support lock 392, shown in detail in FIGS. 14A and 14C, includes a moveable arm 380 which is rotatably connected to a pivot 388. To expand ring 302, arm 380 is rotated approximately 90 degrees in a clockwise direction 394 with respect to a pivot support 390.

Figure 14D:
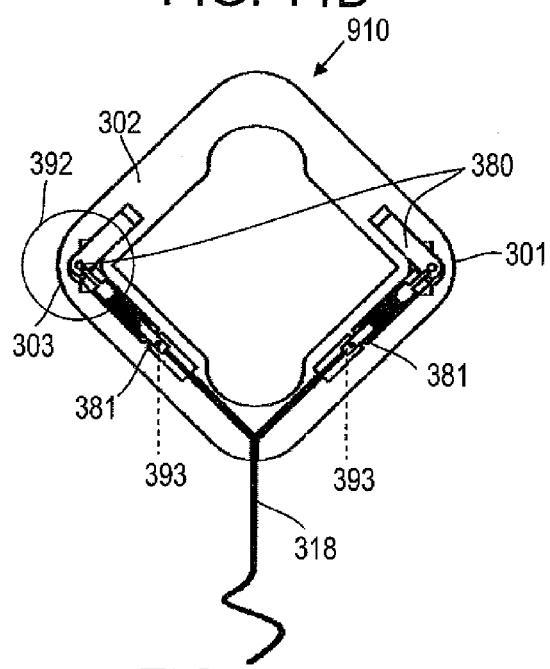

Rod 381 with prong 382 at its distal end, is pressed forward by a spring 384, so that prong 382 then enters into a slot 386, and locks arm 380 in position so that ring 302 is maintained in the expanded configuration (FIG. 14D).

While integrated support pessary 910 is shown with two support locks 392, thereby forming ring 302 into a rhomboid expanded configuration, integrated support pessary 910 may be configured with three, four or even six or more support locks 392 so that ring 302 may attain any one of many configurations, for example a hexagonal expanded shape.

Removal of Integrated Pessary

To collapse ring 302 in preparation for removal of integrated support pessary 910, string 318 is pulled. An end of string 318 connected at a point 393 to rod 381, causes spring 384 to compress, thereby pulling prong 382 out of slot 386.

With prong 382 disengaged from slot 386, ring 302 will return to a natural collapsed configuration.

An alternative embodiment of integrated support pessary 910 is shown in FIGS. 15A-15D in which a prong 400 has a point 402 while arm 380 includes a first stop 404 and a second stop 406.

Figure 15A:
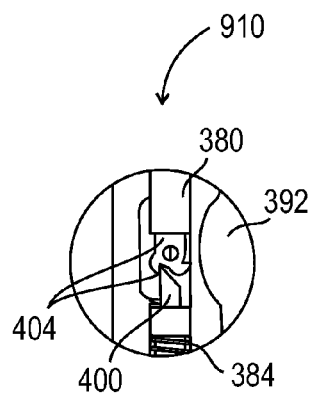
Figure 15B:
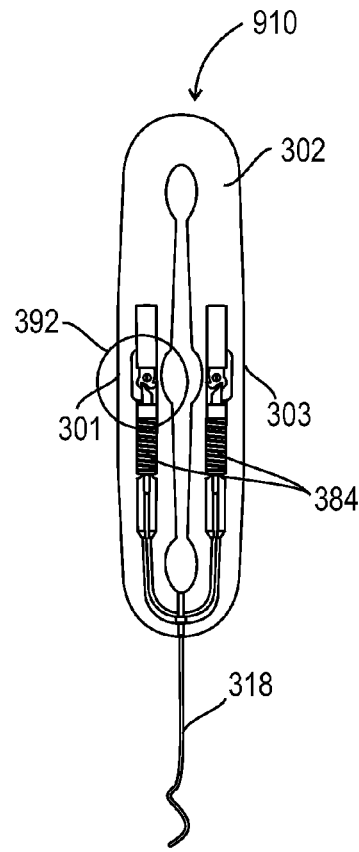
Figure 15C:
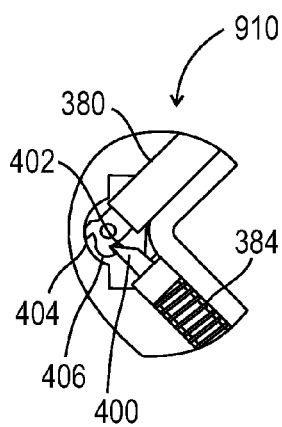
Figure 15D:
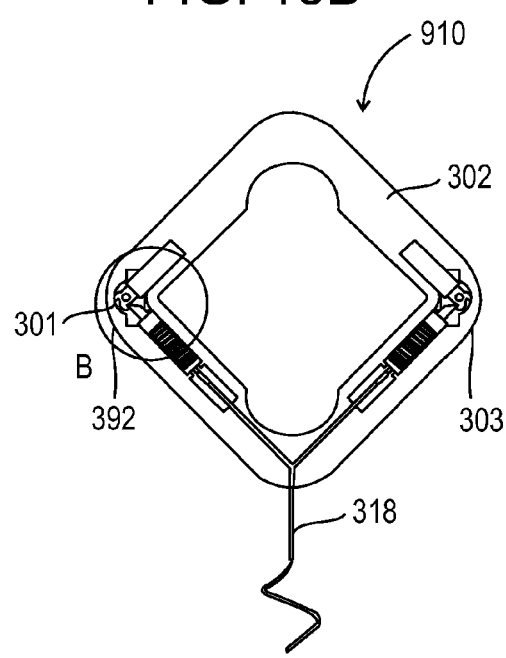

When ring 302 is in the unexpanded configuration, point 402 presses against first stop 404 (FIG. 15A). When ring 302 is in the expanded configuration, point 402 locks against second stop 406 (FIG. 15C).

In some embodiments of the invention, the support mechanism may have many alternative locking configurations; the following embodiment presenting just one such embodiment.

Alternative Lock Pessary

FIGS. 20A-20B show an alternative lock pessary 940 with ring 302 in the collapsed configuration and prongs 157 projecting through lower openings 177. Alternative lock pessary 940 is deployed by compressing ring 302 while a bullet projection 59 maintains alignment as tubes 152 and 156 telescope.

Upon attaining full expansion of ring 302, prongs 157 align with, and lock into, apertures 148, thereby locking tubes 156 and 152 in the telescoped configuration (FIG. 20C).

To collapse ring 302, string 318 is pulled, causing a springy rectangle 259, alternatively diamond shaped spring 259, to elongate so that prongs 157 are released from apertures 148 (FIGS. 20D-20E). Ring 302 will then return to its natural collapsed configuration.

In some embodiments of the invention, a pessary support may have a support structure having two different positions when ring 302 is in the compact configuration; the following presenting just one such embodiment.

Dual Compact Position Pessary

FIGS. 21A-21F show a dual compact position pessary 830 having an "H" shaped spring 151 (FIG. 21F), including upper prongs 123 and lower prongs 155. Juxtaposed on H spring 151 is a slide bar 153 that slides in direction 321 prior to compaction of ring 302 (FIG. 21C).

Slide bar 153 includes a wedge 199 on an upper end, and string 318 attached to a lower end.

As shown in FIG. 21A, ring 302 is in a compact configuration with tubes 252 and 256 extended, and upper prongs 123 are engaged with aperture 148 in inner tube 252.

With ring 302 in the compact pre-deployed configuration, H spring 151 is substantially in the middle of ring 302 along the longitudinal axis of ring 302; constituting a first disengaged position of H spring 151. In the compact "pre-deployed" configuration, lower prongs 155 engage neither tube 252 nor 256.

Ring 302 is then compressed, causing outer tube 256 to move in direction 319, past upper prongs 123 until lower prongs 155 engage lower apertures 196 which are in the lower end of outer tube 256. Upper ends of the H spring remain in apertures 148; thereby maintaining the ring in the expanded position with "H"-shaped spring 151 in the lower portion of outer tube 256.

Exemplary Removal of Dual Compact Position Pessary

To remove dual compact position pessary 830, string 318 is pulled in direction 321 as shown in FIG. 21C. Slide bar 153 moves in direction 321 so that wedge 199 moves in direction 321 and disengages from between upper prongs 123.

Continued pulling in direction 321 causes "H"-shaped spring 151 to move in direction 321 so that a lower edge of upper prongs 123 presses against a lower edge of aperture 148, causing upper prongs 123 to bend medially and disengage from apertures 148, in the absence of wedge 199.

As shown in FIG. 21D, continued pulling on string 318 in direction 319, and/or the natural resiliency of ring 302, causes inner tube 252 to move upward in direction 321 with respect to outer tube 256, thereby allowing tubes 252 and 256 to extend until maximally extended as shown in FIG. 21E.

"H"-shaped spring 151 occupies a second disengaged position in the lower portion of outer tube 256, while inner tube 252 has retracted in upward direction 319.

There are some embodiments of alternative locking mechanisms comprising rotatable locking mechanisms that disengage to allow collapse of ring 302, the following embodiment being just one such example.

Disengageable Lock Pessary

FIGS. 22A-G show a disengageable lock pessary 840 in which a locking mechanism 277, shown in detail in FIG. 22G, includes a semi-circular piece 175 that rotates in a direction 179 around a wheel 171.

Semi-circular piece 175 includes an inner track 824, alternatively referred to as a trough, having an engaging portion 826 that includes a narrow transverse dimension that engages wheel 171 when wheel 171 is disposed in engaging portion 826.

Inner track 824 additionally includes a release portion 822 having a wide transverse dimension that releases wheel 171 when wheel 171 is disposed in release portion 822.

As shown in FIG. 22A, semi-circular piece 175 is an extension of small diameter tube 156 which slides in direction 319 into larger diameter tube 152. Wheel 171 is connected to ring 302, optionally via a connection 147.

To deploy disengageable lock pessary 840, ring 302 is compressed until attaining a configuration shown in FIG. 22B in which prong 157 optionally engages aperture 148 and maintains the telescoped expanded configuration.

To collapse disengageable lock pessary 840, as shown in FIGS. 22D-22E, string 318, attached at a point 819 to semi-circular piece 175, is pulled in direction 321 and causes semi-circular piece 175 to rotate in direction 179.

When wheel 171 aligns with a release portion 822, the natural resiliency of ring 302 causes disengagement between wheel 171 and semi-circular piece 175. As shown in FIG. 22F, large diameter tube 152 remains connected to small diameter tube 156 via prong 157 in aperture 148. Large diameter tube 152 along with semi-circular piece 175 retract upward in direction 319 while wheel 171 moves downward in direction 321; and ring 302 reverts to the compact configuration.

A flip lever pessary, presented below, comprises still another embodiment of many possible alternative rotatable locking mechanisms that disengage to allow collapse of ring 302.

Flip Lever Pessary

FIGS. 23A-23H show a flip lever pessary 880 including a wheel 180 having a lever 181. Wheel 180 is rotatably connected to large diameter (lower) tube 152.

Figure 23H:
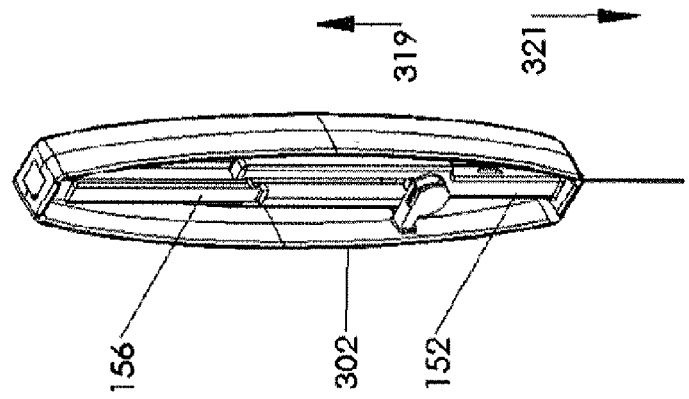
Figure 23G:
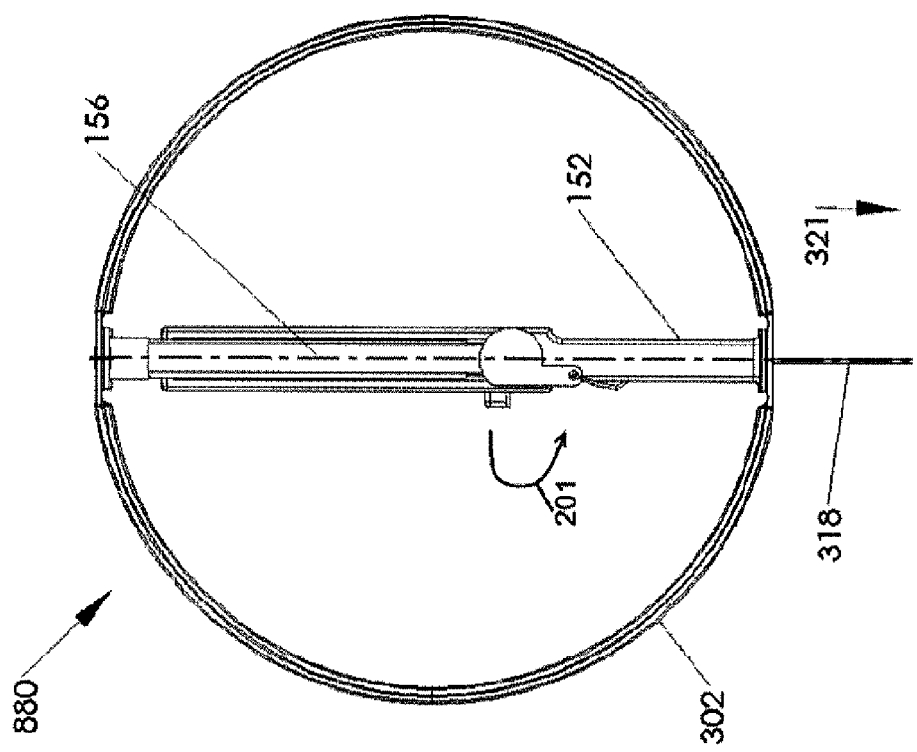
Figure 23F:
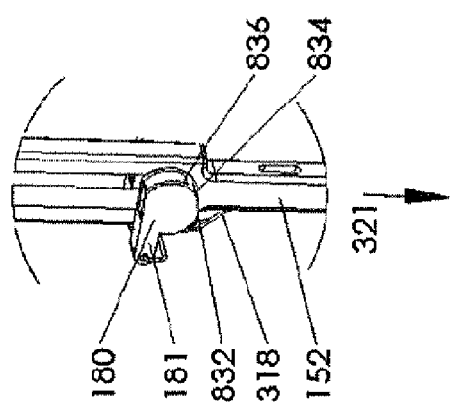

As shown in FIG. 23F, wheel 180 includes a curved inner facing rim 834 which has an engaging portion 836 with a narrow transverse dimension; and a release portion 832 with a wide transverse dimension.

As shown in FIG. 23F, curved periphery 834 is configured to be engaged with snap connectors 182 positioned at the end of small diameter tube 156.

To deploy flip lever pessary 880, shown in FIGS. 23C-E, ring 302 is compressed until inner facing rim 834 compresses and passes snap connectors 182 and enters inner tube recesses 184. Snap connectors 182 return to an uncompressed configuration to lock inner facing rim 834 in inner tube recesses 184; thereby locking ring 302 in the expanded position.

Exemplary Removal of Flip Lever Pessary

As shown in FIG. 23G, to remove flip lever pessary 880, string 318, attached to the end of lever 181, is pulled in direction 321 and causes wheel 180 to rotate in a direction 201 until release portion 832 becomes aligned with snap connectors 182.

As shown in FIG. 23H, when snap connectors 182 become aligned with release portion 822 the natural resiliency of ring 302 causes disengagement of wheel 180 from small diameter tube 156. Wheel 180 moves in direction 321, while small diameter tube 156 moves in direction 319, and ring 302 returns to a compact configuration.

Some embodiments of the invention may include alternative expanding portions to ring 302, for example an inflatable body; the following describing just one embodiment of an inflatable pessary.

Inflatable Pessary

Figures 16A, 16B:
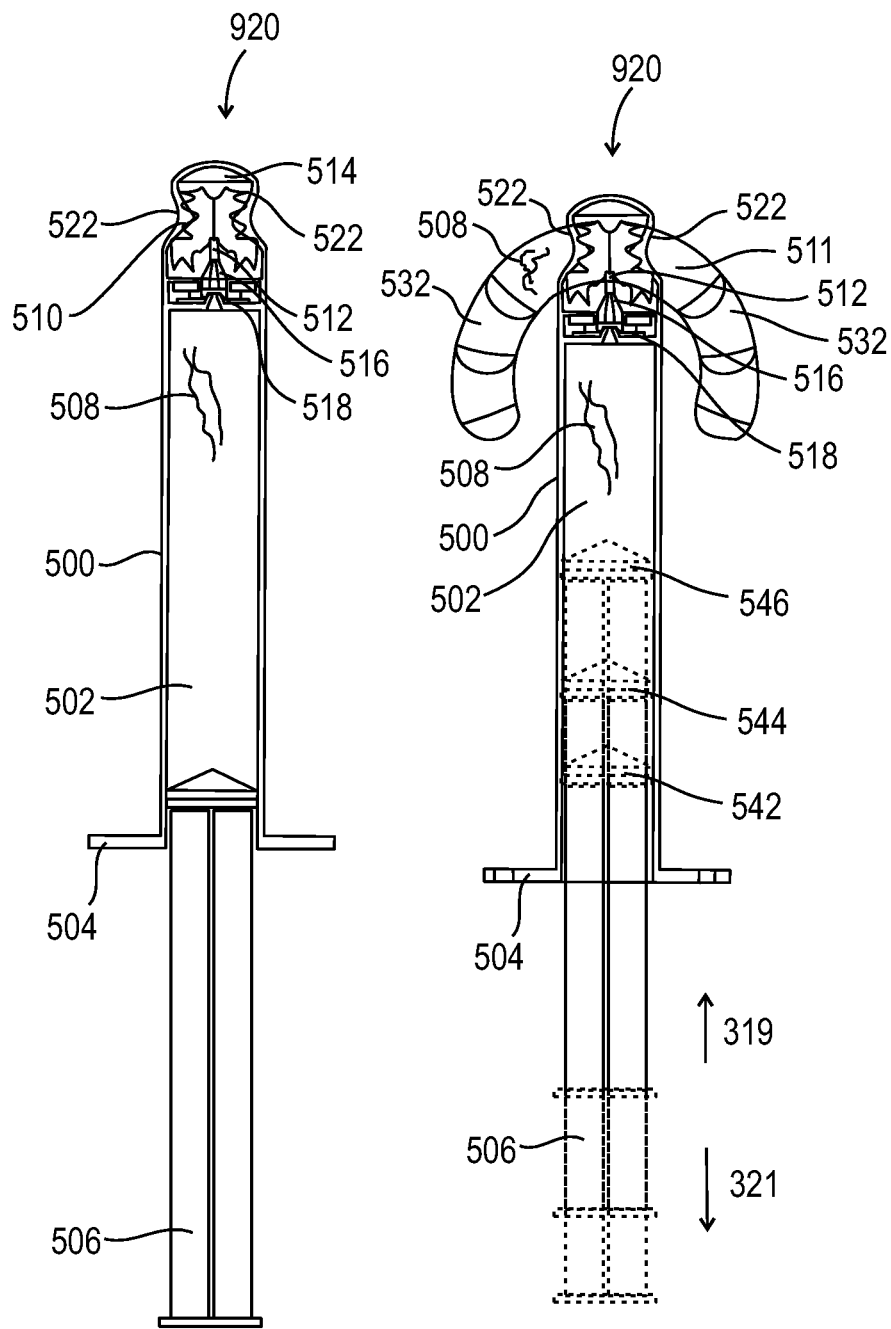

FIGS. 16A-16B show an inflatable pessary 920 having an inflatable body 511 that inflates with various fluids 508 stored in fluid chamber 502. Fluids may include a gas, for example air or nitrogen; or a liquid such as water. In some embodiments of the invention, in the unexpanded configuration, inflatable body 511 is substantially contained within a housing 514.

To expand inflatable body 511, rims 504 on fluid chamber 502 are held between the user's second and third fingers while the thumb presses a plunger 506.

In some embodiments of the invention, housing 514 is connected to fluid chamber 502 through a one way valve 516 that optionally controls the rate of fluid entry or exit from inflatable body 511. In this manner, one way valve 516 may protect the user from discomfort that may result from overly-rapid inflation.

Housing 514 is typically configured to allow portions of inflatable body 511 to expand external to housing 514 during and following expansion. For example, in the horseshoe-shaped inflatable body 511 shown in FIG. 16B, housing 514 includes side openings 522 that allow pessary arms 532 to exit housing 514 and expand.

Fluid chamber 502 is optionally connected to housing 514 with a quick release connection 518, for example a bayonet lock. Following inflation of inflatable body 511, quick release connection 518 is activated by the user and fluid chamber 502 is disconnected from housing 514 for disposal, or for future use according to some embodiments. Upon disconnection, one way valve 516 prevents deflation of body 511. Housing 514 typically remains together with expanded inflatable body 511 in the vagina while inflatable pessary 920 is in use.

In some embodiments of the invention, fluid chamber 502 may be a canister of compressed gas and supplied to the user while it is connected to housing 514. In such embodiments, fluid chamber 502 can be disposed of following deployment of inflatable pessary 920.

Exemplary Removing Inflatable Pessary

To deflate and remove inflatable pessary 920, as shown in FIGS. 17A-18B, string 318 is pulled with a short and rapid motion in direction 321, causing one way valve 516 to disengage from a supply channel 512.

Upon disengagement, a space 509 is created between one way valve 516 and supply channel 512, allowing fluid to be released, thereby deflating inflatable body 511. Upon deflating inflatable body 511 to a size that is easily removed from the vagina, string 318 is pulled with a long, steady pull in direction 321 to draw inflatable pessary 920 out of the vagina.

Inflatable Pessary Configurations

While inflatable body 511 in the expanded form is depicted as having a horseshoe shaped periphery, pessary arms 532 may attain any one of many peripheral shapes including an open "V" shape, or a circular or rhomboid shape in which the ends of pessary arms 532 are in close proximity or even contacting each other. The shape of inflatable body 511 may be chosen, for example, based upon which organ is causing the prolapse.

For example to fully stretch the vaginal walls in treating a herniated rectum, inflatable body 511 may be configured to form a substantially full circle or rhomboid; while for treating a prolapsed vaginal vault, arms 532 may be shorter, for example as shown in FIG. 16B.

Additionally, in some embodiments the user may be allowed to control the amount of pressure exerted by arms 532 against the walls of the vagina. For example, the user may push plunger 506 to a position 542 to expand inflatable body 511 so that arms 532 exert a minimal level of pressure. Upon determining that greater pressure is desirable to control organ prolapse, the user may optionally press plunger to a position 544 or a position 546 to achieve appropriate pressure.

In some embodiments of the invention, prior to deployment, fluid chamber 502 may contain a user-specific volume of fluid. The volume of fluid in fluid chamber 502 may be determined by the user or a caregiver based upon user comfort with respect to pressure exerted by arms 532 and/or optimal treatment of organ prolapse.

In embodiments where fluid 508 comprises water, fluid chamber 502 may be supplied to the user separately and unconnected to housing 514, in a dispenser having a syringe-like configuration. In such embodiments, the user may draw the appropriate volume of water into fluid chamber 502, for example from a water cartridge, prior to connecting fluid chamber 502 to housing 514.

In embodiments where fluid 508 comprises a compressed gas, fluid chamber 502 may have an inlet (not shown) through which the user fills fluid chamber 502 with an appropriate volume of gas from a separate compressed gas cartridge.

In some alternative embodiments of the invention, a pessary includes dual parallel arms that separate during expansion, the following being a description of just one such one embodiment.

Dual Arm Pessary

Figure 19A:
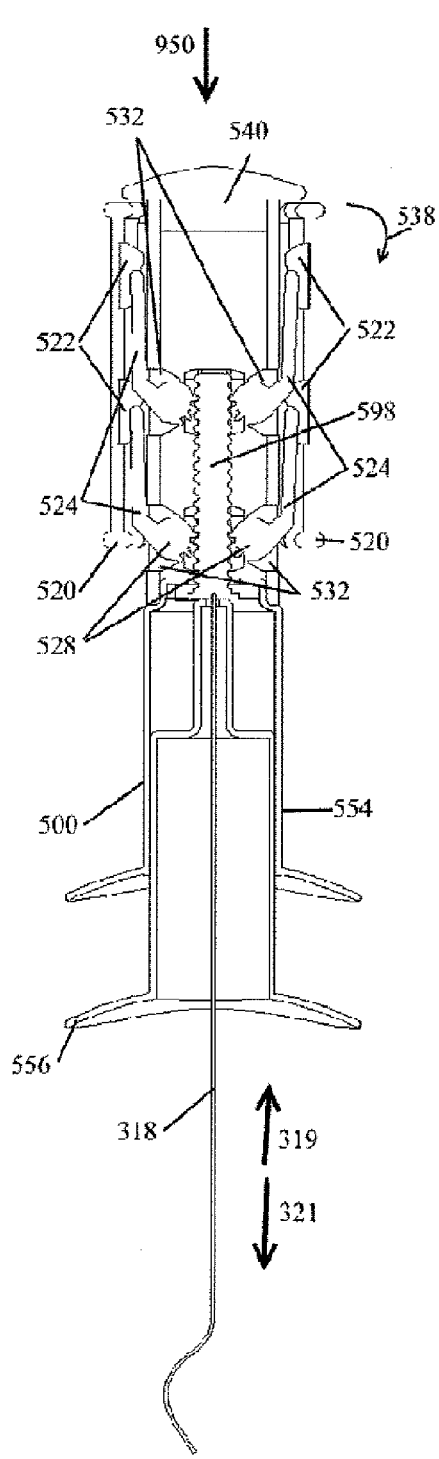
FIGS. 19A-19C show portions and operation of a pessary including dual elongate elements, according to some embodiments of the present invention.
Figure 19B:
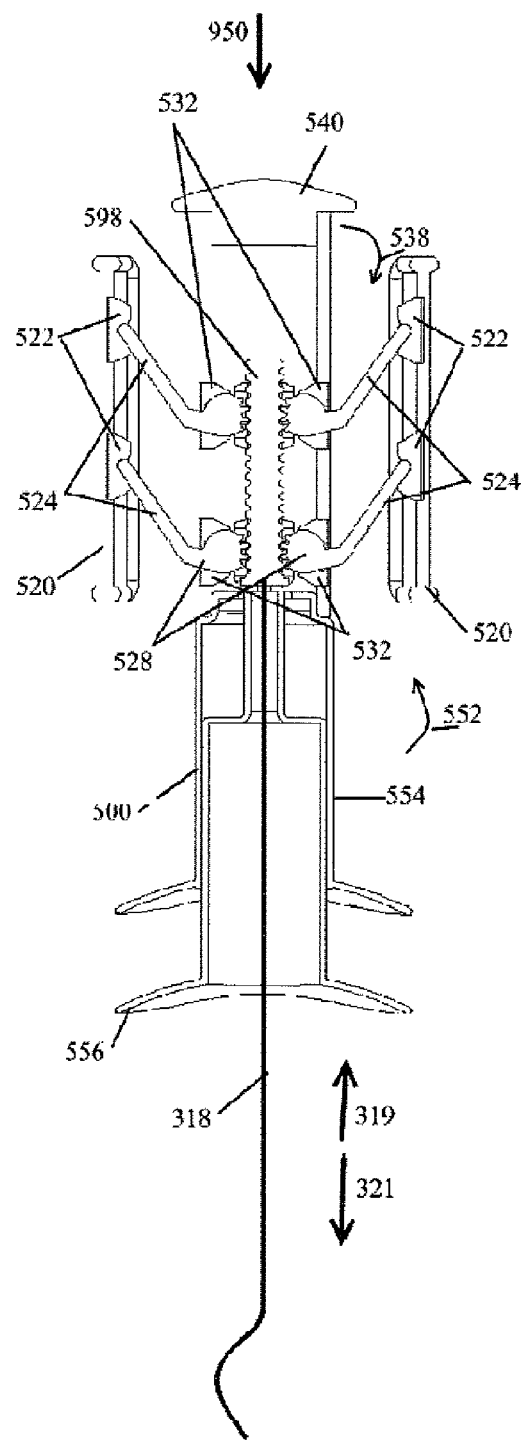
Figure 19C:
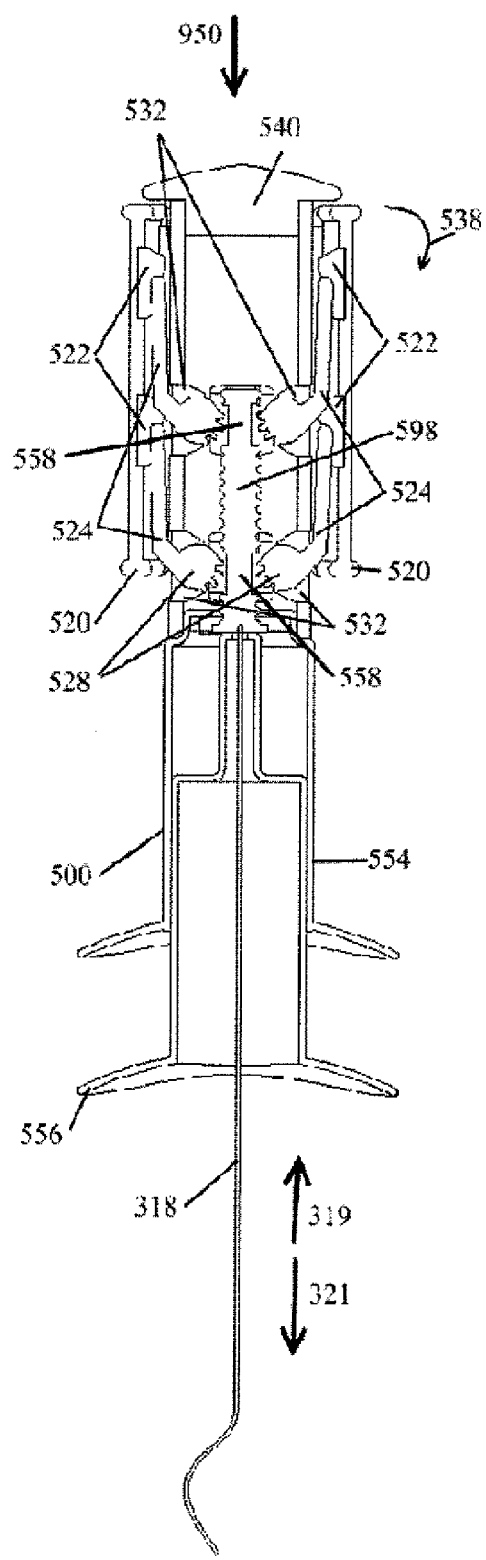

Shown in FIGS. 19A-19C is a dual arm pessary 950 comprising a housing 540 having openings 532. Arm supports 524 pass through openings 532 and optionally rotatably connect to connectors 522 on arms 520.

Within housing 540 is a rack 598, connected to string 318. The teeth on rack 598 engage, within housing 540, with the teeth on pinions 528 on arm supports 524.

Exemplary Use of Dual Arm Pessary

In some embodiments of the invention, prior to deployment, dual arm pessary 950 is connected to an applicator 500 having an applicator housing 554 containing an applicator plunger 556. By pressing applicator plunger 556, rack 598 moves in direction 319 causing arm supports 524 to rotate in a downward direction 538 with respect to housing 540; and arms 520 move outward from housing 540.

In some embodiments of the invention, the outer surfaces of arms 520 are separated by a distance of 25 to 45 millimeters in the unexpanded configuration, and by a distance of 50-120 millimeters in the expanded configuration.

Optionally, applicator 500 is connected to pessary 950 with a quick disconnection mechanism as described above and, following deployment, applicator 500 is easily disconnected from dual arm pessary 950. Following deployment, applicator 500 is disconnected from dual arm pessary 950 and disposed of or cleaned for reuse.

For removal, dual arm pessary 950 is stabilized in position inside the vagina and string 318 is pulled in direction 321. In response to the pull on string 318, rack 598 moves in direction 321, causing arm supports 524 to rotate in an upward direction 552 so that arms 520 move toward housing 540.

Dual Arm Pessary Embodiments

In some embodiments of the invention, applicator 500 may be disassembled and cleaned for reuse so that dual arm pessary 950 may be repeatedly deployed.

In other embodiments, dual arm pessary 950 is configured for a single use. For example, as shown in FIG. 19C, rack 598 may include cutout areas 558 so that once collapsed, the teeth pinions 528 cannot be reengaged with rack 598 and dual arm pessary 950 must be discarded.

Dual arm pessary 950 may be supplied in a variety of configurations to treat, for example, different vaginal sizes and/or different prolapsed organs.

For example, to treat prolapse in a relatively small and wide vagina, arms 520 may be relatively short and wide. To treat prolapse in a relatively large and narrow vagina, arms 520 may be relatively long and narrow.

Alternatively, dual arm pessary 950 may be configured with two, three, or four or more sets of arms 520 with each set of dual arms 520 having, for example, a different final distance from housing 540; for example, each set configured for treating a different prolapsed organ in users suffering from multiple organ prolapse.

Exemplary Space Filling Pessary

Figure 24A:
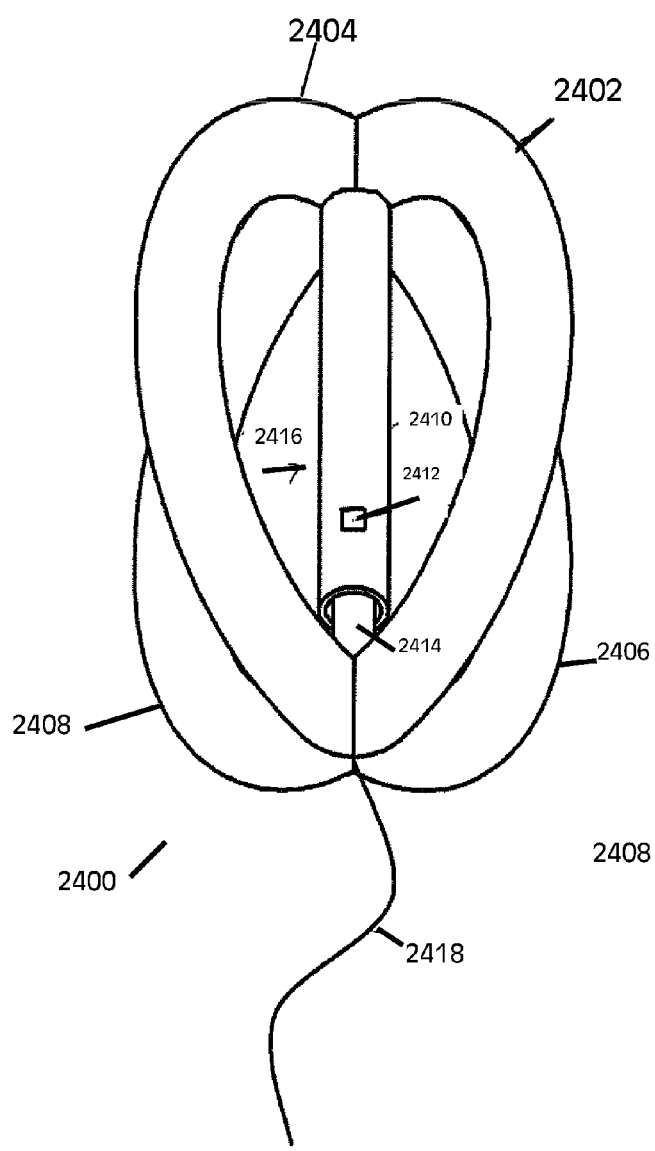
FIGS. 24A and 24B show a volumetric embodiment of the invention.
Figure 24B:
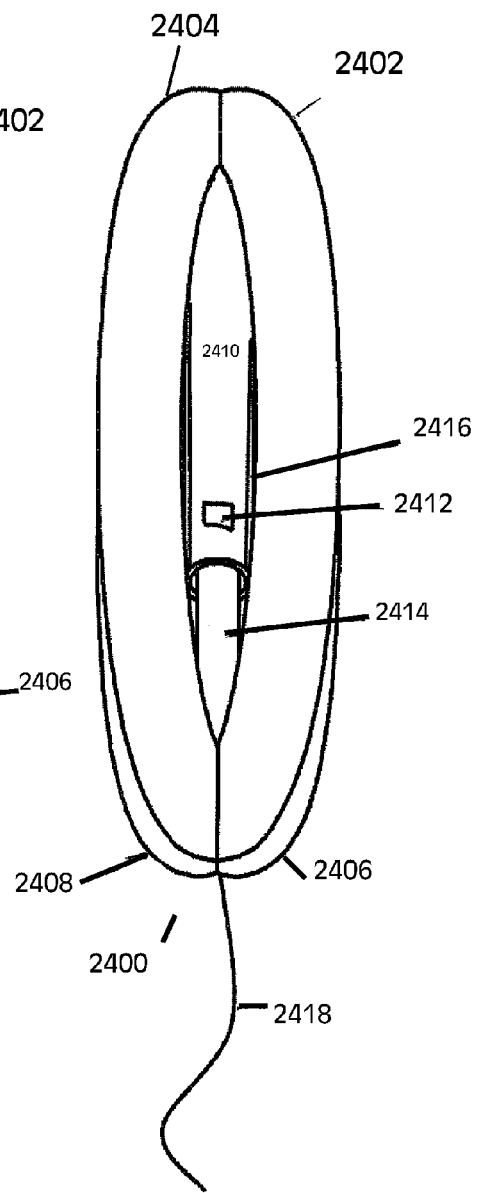

FIGS. 24A and 24B show an example of a pessary which is not planar. It is noted that in any of the above embodiments, the basic shape (e.g., ring) need not be flat, for example, the sides of the ring may curve up or down, the sides of the ring (where they contact the vaginal wall) may be thicker than the leading edge of the ring and/or the pessary may curve along its main axis (e.g., the vaginal axis). Some of these shapes fit in a plane, albeit curved, for example with a ratio of thickness to width of less than 1:3.

FIGS. 24A and 24B show a pessary 2400 in which the pessary is space filling. In the embodiment shown, a plurality of arc sections 2402, 2404, 2406 and 2408 define a generally spherical, rectangular or ovoid shape when expanded (FIG. 24A). When in a compressed state (FIG. 24b), all trans-axial dimensions of the pessary are small, to facilitate delivery and/or fitting into an applicator.

In an exemplary embodiment of the invention, the basic structure of pessary 2400 is that of multiple intersecting rings, each formed of two of arcs 2402, 2404, 2406 and 2408. Optionally, two actual rings are used, optionally one with a diameter greater than the other. Other number of arcs may be used as well, for example, 5 and/or arcs that do not share flat planes as pairs.

Optionally, the pessary directly supports one or more prolapsed organs additionally or alternatively to stretching the vaginal wall in multiple directions as some of the above embodiments.

In an alternative embodiment, a plurality of stacked (e.g., with their planes parallel to each other) rings (or other shapes) are provided, to provide space filling.

In the embodiment show, a single state changing mechanism 2416 is used for multiple orthogonal expansion directions. Any of the state change mechanism described above may be used. In the example shown, an optional string 2418 can be used to selectively lock or unlock (in one or more positions) an outside tube 2410 to an inside telescoping element 2414, optionally via a lock 2412 (e.g., a window in which one of two or more elastic protrusions of element 2414 can exit and engage).

In an alternative embodiment, each arc or pair of arcs has a separate state changing mechanism, for example, as shown above for state changing mechanism that are wholly enclosed in the rings.

Optionally, the pessary is covered by a cover and/or includes a membrane between at least some of the arcs, so as to be more space filling. Optionally, however, the pessary includes large passages for vaginal secretions therepast (including therethrough).

General

It is expected that during the life of a patent maturing from this application many relevant pessary configurations will be developed and the scope of the term pessary is intended to include all such new technologies a priori. As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral fractional or integral within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A vaginal pessary sized and shaped for alleviating organ prolapse, comprising:
    (a) a space filling body extending in at least two orthogonal directions not along the vaginal axis including at least two rib sections adapted to, at least in one state, extend along a vaginal axis and apply force to facing vaginal walls along axial extents thereof, wherein said body is adapted to be in at least two states:
        (i) a compressed state in which said body is sized for insertion into said vagina; and
        (ii) an expanded state in which said body is sized and stiff enough for providing organ prolapse alleviation and in which state said ribs extend along a vaginal axis and apply force to facing vaginal walls; and
    (b) a locking, two-stepped, state changing mechanism integral to said pessary and configured to change a configuration of said body from one state to the other state, which mechanism does not use fluid flow to cause state change and wherein the state changing mechanism comprises a lock element on an outside tube and two or more elastic protrusions on an inside telescoping element pre-configured to move into said lock element to establish a locked condition when the inside telescoping element is advanced sufficiently inside the outside tube;

wherein said pessary is stable in shape and size in both states.

2. A pessary according to claim 1, wherein said body in said expanded state alleviates organ prolapse by directly supporting a prolapsed organ.

3. A pessary according to claim 1, wherein said body is substantially rigid in said expanded state.

4. A pessary according to claim 1, wherein said state changing mechanism locks said pessary in at least one of said two states.

5. A pessary according to claim 1, wherein said body comprises a plurality of orthogonal planar shapes.

6. A pessary according to claim 5, wherein said plurality of orthogonal planar shapes change state together by way of a single state changing mechanism.

7. A pessary according to claim 1, wherein said state changing mechanism is at least mostly enclosed by said body.

8. A pessary according to claim 1, wherein the body is comprised of a plurality of arc sections which define a generally spherical, rectangular or ovoid shape when in the expanded state.

9. A pessary according to claim 1, wherein the body is configured with multiple intersecting rings.

10. A pessary according to claim 9, wherein the intersecting rings are not the same diameter.

11. A pessary according to claim 1, further comprising a cover substantially covering the body.

12. A pessary according to claim 11, wherein the cover includes a membrane between at least some of the rib sections.

13. A pessary according to claim 1, wherein the body allows flow of vaginal secretions therepast.

14. A pessary according to claim 1, comprising a control coupled to the state-changing element and configured to activate a state change when said control is pulled when inside a body.

15. A pessary according to claim 1, wherein the pessary is functionally rotationally symmetric around the vaginal axis.

16. A pessary according to claim 1, mounted on an applicator.

17. A pessary according to claim 1, wherein the rib sections are odd in number.

18. A pessary system comprising:
(a) a shape changing pessary according to claim 1 adapted to alleviate organ prolapse when deployed in a vagina; and
(b) an applicator adapted for holding the pessary while in a form suitable for insertion into a vagina.

19. A pessary system according to claim 18, wherein the applicator is configured to actively change a shape of the pessary after insertion thereof into a vagina.

* * * * *